US006693086B1

(12) United States Patent
Dow et al.

(10) Patent No.: US 6,693,086 B1
(45) Date of Patent: Feb. 17, 2004

(54) SYSTEMIC IMMUNE ACTIVATION METHOD USING NUCLEIC ACID-LIPID COMPLEXES

(75) Inventors: Steven W. Dow, Littleton, CO (US); Robyn E. Elmslie, Littleton, CO (US); Jürgen Karl Johannes Schwarze, Denver, CO (US)

(73) Assignee: National Jewish Medical and Research Center, Denver, CO (US)

( * ) Notice: Subject to any disclaimer, the term of this patent is extended or adjusted under 35 U.S.C. 154(b) by 0 days.

(21) Appl. No.: 09/104,759

(22) Filed: Jun. 25, 1998

(51) Int. Cl.$^7$ .................. A61K 48/00; A61K 9/127; C12N 15/63; C12N 15/87; C07H 21/04
(52) U.S. Cl. ............... 514/44; 424/450; 435/320.1; 435/455; 536/23.1
(58) Field of Search .............. 514/44; 435/320.1, 435/455; 536/23.1; 424/450

(56) References Cited

U.S. PATENT DOCUMENTS

| 5,399,346 | A | * | 3/1995 | Anderson et al. ......... 424/93.21 |
| 5,580,859 | A | | 12/1996 | Felgner et al. ............... 514/44 |
| 5,589,466 | A | | 12/1996 | Felgner et al. ............... 514/44 |
| 5,593,972 | A | | 1/1997 | Weiner et al. ............... 514/44 |
| 5,641,662 | A | | 6/1997 | Debs et al. ............... 435/172.1 |
| 5,643,578 | A | | 7/1997 | Robinson et al. ......... 424/210.1 |
| 5,676,954 | A | | 10/1997 | Brigham ..................... 424/450 |
| 5,679,647 | A | | 10/1997 | Carson et al. ............... 514/44 |
| 5,693,622 | A | | 12/1997 | Wolff et al. ................. 514/44 |
| 5,703,055 | A | | 12/1997 | Felgner et al. ............... 514/44 |
| 5,703,057 | A | | 12/1997 | Johnston et al. ............. 514/44 |
| 5,827,703 | A | | 10/1998 | Debs et al. ............... 435/172.3 |
| 5,830,878 | A | * | 11/1998 | Gorman et al. ............... 514/44 |
| 6,121,247 | A | * | 9/2000 | Huang et al. ................. 514/44 |
| 6,224,901 | B1 | * | 5/2001 | Li et al. ..................... 424/450 |

FOREIGN PATENT DOCUMENTS

| EP | 0 819 758 A2 | 1/1998 |
| WO | WO93/25673 | 12/1993 |
| WO | WO94/04196 | 3/1994 |

OTHER PUBLICATIONS

Leitner et al., DNA and RNA–based vaccines: principles, progress and prospects, 1999, Elsevier Science, vol. 18 (2000) 765–777.*
Verma et al., Gene Therapy–promises, problems and prospects, Nature: Vol 389, Sep. 18, 1997.*
Orkin, et al., Report and Recommendations of the panel to assess the NIH investment in research on gene therapy, Dec. 7, 1995.*
Carson et al., Cationic lipids inhibit intradermal genetic vaccination, 1994, Vaccines 94, pp. 71–75.*
Ballas, 1996, *The Journal of Immunology*, 157:1840–1845.
Freimark et al., 1998, *The Journal of Immunology*, 160:4580–4586.
Gao, "Cationic Lipid–Based Gene Delivery: An Update," Chapter 6, pp. 99–112 (undated).
Krieg, 1996, *Trends in Microbiology*, 4(2):73–77.
Lesoon–Wood et al., 1995, *Human Gene Therapy*, 6:395–405.
Li et al., 1996, *The Journal of Immunology*, 157:3216–3219.
Liu et al., 1997, *Nature Biotechnology*, 15:167–173.
McLean et al., 1997, *Am. J. Physiol.*, 273:H387–H404.
Pisetsky, 1996, *The Journal of Immunology*, 156:421–423.
Pisetsky et al., 1996, *Immunity*, 5:303–310.
Rodman et al, "Delivery of Genes Through the Lung Circulation," Chapter 9, pp. 181–191 (undated.
Roman, et al., 1997, *Nature Medicine*, 3(8):849–854.
Rosenberg et al., 1985, *J. Exp. Med.*, 161:1169–1188.
Sato, et al., 1996, *Science*, 273:352–354.
Scheule et al., 1997, *Human Gene Therapy*, 8:689–707.
Stacey et al., 1996, *The Journal of Immunology*, 157:2116–2122.
Sun, et al., 1996, *Immunity*, 4:555–564.
Templeton et al., 1997, *Nature Biotechnology*, 15:647–652.
Yamamoto, et al., 1994, *Microbiol. Immunol.*, 38(10):831–836.
Gregoriadis et al., *FEBS Letters*, 402(2–3):107–110 (1997).
Naitoh et al., *Proc. Ann. Meet. Am. Assoc. Cancer. Res.*, 39:355 (1998) Abstract #2421.
Okamoto et al., *Proc. Annu. Meet. Am. Assoc. Cancer Res.*, 38 (1997) Abstract #78.

* cited by examiner

*Primary Examiner*—Anne M. Wehbé
(74) *Attorney, Agent, or Firm*—Steven C. Petersen; Hogan & Hartson LLP

(57) ABSTRACT

This invention relates to a method for systemic immune activation which is effective for eliciting both a systemic, non-antigen specific immune response and a strong antigen-specific immune response in a mammal. The method is particularly effective for protecting a mammal from a disease including cancer, a disease associated with allergic inflammation, or an infectious disease. Also disclosed are therapeutic compositions useful in such a method.

18 Claims, 30 Drawing Sheets

SYSTEMIC IMMUNE ACTIVATION METHOD USING NUCLEIC ACID-LIPID COMPLEXES

FIELD OF THE INVENTION

The present invention relates to a composition and method to elicit an immune response in a mammal using a genetic immunization strategy. More particularly, the present invention includes compositions and methods for eliciting systemic, non-specific (i.e., non-antigen-specific) immune responses in a mammal as well as antigen-specific immune responses, both of which are useful in immunization protocols.

BACKGROUND OF THE INVENTION

Vaccines are widely used to prevent disease and to treat established diseases (therapeutic vaccines). There remains, however, an urgent need to develop safe and effective vaccines and adjuvants for a variety of diseases, including those due to infection by pathogenic agents, cancers and other disorders amenable to treatment by elicitation of an immune response.

Three major types of disease in mammals which are amenable to elicitation and/or modulation of an immune response include infectious diseases, allergic inflammatory diseases and cancer, although the present invention is not limited to treatment of these disease types. Infectious diseases are caused by infectious agents (i.e., infectious disease pathogens), examples of which include viruses, bacteria, parasites, yeast and other fungi. In allergic inflammatory diseases, allergens cause the release of inflammatory mediators that recruit cells involved in inflammation in allergic or sensitized animals, the presence of which can lead to tissue damage and sometimes death. Cancer can result from an inherited inability to repair DNA, to prevent DNA damage or to prevent propagation of cells with damaged DNA, and/or from a biochemical dysfunction or genetic mutation which leads to uncontrolled cell proliferation and DNA synthesis.

Traditional reagents that are used in an attempt to protect a mammal from such diseases include reagents that destroy infectious agents or the cells involved in deregulated biological functions, or that modify the activity of such cells. Such reagents, however, can result in unwanted side effects. For example, anti-viral drugs that disrupt the replication of viral DNA also often disrupt DNA replication in normal cells in the treated patient. The use of anti-inflammatory and symptomatic relief reagents in allergic inflammation is a serious problem because of their side effects or their failure to attack the underlying cause of an inflammatory response. Other treatments with chemotherapeutic reagents to destroy cancer cells typically leads to side effects, such as bleeding, vomiting, diarrhea, ulcers, hair loss and increased susceptibility to secondary cancers and infections.

An alternative method of disease treatment includes modulating the immune system of a patient to assist the patient's natural defense mechanisms. Traditional reagents and methods used to attempt to regulate an immune response in a patient also result in unwanted side effects and have limited effectiveness. For example, immunopharmacological reagents used to treat cancer (e.g., interleukins) are short-lived in the circulation of a patient and are ineffective except in large doses. Due to the medical importance of immune regulation and the inadequacies of existing immunopharmacological reagents, reagents and methods to regulate specific parts of the immune system have been the subject of study for many years.

Vaccines can be used not only to prevent disease, but can also be used to treat established diseases (i.e., therapeutic vaccines). A number of tumor antigens which are recognized by T lymphocytes of the immune system have been recently identified and are being considered as potential vaccine candidates. Conventional vaccines generally consist of either (1) purified antigens administered with an adjuvant, or (2) an attenuated form of a pathogen that can be administered to a patient to generate an immune response, but not cause serious disease or illness.

Genetic vaccines, by contrast, contain a DNA sequence that encodes an antigen(s) against which the immune response is to be generated. For genetic vaccines to generate an antigen-specific immune response, the gene of interest must be expressed in the mammalian host. Gene expression has been accomplished by use of viral vectors (e.g., adenovirus, poxvirus) that express the foreign gene of interest in the vaccinated patient and induce an immune response against the encoded protein. Alternatively, plasmid DNA encoding a foreign gene has been used to induce an immune response. The primary routes of administration of these so-called "naked" DNA vaccines are intramuscular or percutaneous. It is generally accepted that viral vector systems induce better immune responses than naked DNA systems, probably because the viral delivery systems induce more inflammation and immune activation than naked DNA vaccines. The propensity of viral vaccines to induce non-specific immune responses, primarily as a result of viral component recognition by the complement cascade, also represents a potential drawback, however, since such immune responses often prevent readministration of the vaccine.

Therefore, there is need to provide better vaccines which can produce an immune response which is safe, antigen-specific and effective to prevent and/or treat diseases amenable to treatment by elicitation of an immune response, such as infectious disease, allergy and cancer.

SUMMARY

One embodiment of the present invention generally relates to a method to elicit a systemic, non-antigen-specific immune response in a mammal. The method includes the step of administering to the mammal a therapeutic composition by a route of administration selected from intravenous and intraperitoneal administration. The therapeutic composition includes: (a) a liposome delivery vehicle; and, (b) an isolated nucleic acid molecule that is not operatively linked to a transcription control sequence. In another embodiment, the route of administration is intravenous. In further embodiments of the method, the isolated nucleic acid molecule comprises a non-coding sequence. In one embodiment, the isolated nucleic acid molecule does not comprise a bacterial nucleic acid sequence.

Accordingly, another embodiment of the present invention is a composition for eliciting a systemic, non-antigen-specific immune response in a mammal. Such a composition includes (a) a liposome delivery vehicle; and (b) an isolated nucleic acid molecule that is not operatively linked to a transcription control sequence. In one embodiment, the nucleic acid molecule does not include a bacterial nucleic acid sequence.

Another embodiment of the present invention relates to a composition for eliciting a systemic, non-antigen-specific immune response in a mammal which comprises (a) a liposome delivery vehicle and (b) an isolated non-coding nucleic acid sequence.

A composition of the present invention can further comprise a pharmaceutically acceptable excipient. A pharmaceutically acceptable excipient can include, for example a non-ionic diluent, and more preferably, 5 percent dextrose in water (D5W).

The above-mentioned method and compositions of the present invention have the advantages of eliciting a systemic, non-antigen specific immune response in a mammal, and more particularly, of eliciting a systemic, anti-viral immune response in a mammal. Additionally, the method and composition of the present invention can elicit a systemic, anti-tumor immune response in a mammal. Such an anti-tumor immune response can result in the reduction of a tumor in the mammal. The method and composition of the present invention can also elicit a systemic, protective immune response against allergic inflammation in a mammal. The systemic, non-antigen-specific immune response elicited by the method and composition of the present invention result in an increase in effector cell activity, and particularly, natural killer (NK) cell activity in the mammal, and additionally can result in increased production of IFNγ in the mammal.

Yet another embodiment of the present invention relates to a method to elicit an immunogen-specific immune response and a systemic, non-specific immune response in a mammal. The method includes administering to the mammal a therapeutic composition by a route of administration selected from intravenous and intraperitoneal. The therapeutic composition comprises: (a) a liposome delivery vehicle; and, (b) a recombinant nucleic acid molecule comprising an isolated nucleic acid sequence encoding an immunogen, wherein the nucleic acid sequence is operatively linked to a transcription control sequence. Particularly suitable transcription control sequences include Rous sarcoma virus (RSV) control sequences, cytomegalovirus (CMV) control sequences, adenovirus control sequences and Simian virus (SV-40) control sequences. This method of the present invention has the particular advantage of eliciting both a systemic, non-immunogen-specific immune response in a mammal, as well as an immunogen-specific immune response that have a potent therapeutic effect in the mammal. In one embodiment, the route of administration is intravenous. In other preferred embodiments, the immunogen is a tumor antigen, an infectious disease pathogen antigen or an allergen.

When the mammal has cancer, this immunogen is preferably a tumor antigen. In one embodiment of this method, the therapeutic composition can include a plurality of recombinant nucleic acid molecules, each of the recombinant nucleic acid molecules comprising a cDNA sequence amplified from total RNA isolated from an autologous tumor sample, each of the cDNA sequences encoding a tumor antigen or a fragment thereof and being operatively linked to a transcription control sequence. In another embodiment, the therapeutic composition comprises a plurality of recombinant nucleic acid molecules, each of the recombinant nucleic acid molecules comprising a cDNA sequence amplified from total RNA isolated from a plurality of allogeneic tumor samples of the same histological tumor type, each of the cDNA sequences encoding a tumor antigen or a fragment thereof and being operatively linked to a transcription control sequence.

The methods and compositions of the present invention are particularly useful for treating a cancer which includes melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. The compositions and methods of the present invention are especially useful for treating primary lung cancer or pulmonary metastatic cancer.

Accordingly, a tumor antigen useful in the present composition is preferably from a cancer selected from the group of melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof. The tumor antigen preferably is selected from the group of tumor antigens having epitopes that are recognized by T cells, tumor antigens having epitopes that are recognized by B cells, tumor antigens that are exclusively expressed by tumor cells, and/or tumor antigens that are expressed by tumor cells and by non-tumor cells.

When the immunogen is a tumor antigen which is expressed in the mammal, the method of the present invention produces a result selected from alleviation of the cancer, reduction of size of a tumor associated with the cancer, elimination of a tumor associated with the cancer, prevention of metastatic cancer, prevention of the cancer and stimulation of effector cell immunity against the cancer. When the tumor antigen is administered intravenously, the antigen is expressed in a pulmonary tissue of the mammal and prevents pulmonary metastatic cancer in the mammal.

When the immunogen is an infectious disease pathogen antigen, the methods and composition of the present invention are useful for mammals having an infectious disease, and particularly for mammals having a chronic infectious disease. Such immunogens can be from infectious disease pathogens which include bacteria, viruses, parasites and fungi. Such infectious disease pathogens include, for example, human immunodeficiency virus (HIV), *Mycobacterium tuberculosis*, herpesvirus, papillomavirus and Candida. The present method is particularly useful when the infectious disease pathogen is a virus, and more particularly, human immunodeficiency virus and feline immunodeficiency virus. In another embodiment, the present method is particularly useful when the infectious disease is tuberculosis. In this embodiment, the immunogen can be, for example, a *Mycobacterium tuberculosis* antigen, or more specifically, antigen 85.

Expression of the pathogen antigen in a tissue of the mammal produces a result selected from the group of alleviation of the disease, regression of established lesions associated with the disease, alleviation of symptoms of the disease, immunization against the disease and/or stimulation of effector cell immunity against the disease.

In one embodiment of this method, the therapeutic composition comprises a plurality of recombinant nucleic acid molecules, each of the recombinant nucleic acid molecules comprising a cDNA sequence amplified from total RNA isolated from an infectious disease pathogen, each of the cDNA sequences encoding an immunogen from the infectious disease pathogen or a fragment thereof and being operatively linked to a transcription control sequence.

When the mammal has a disease associated with allergic inflammation, the immunogen is an allergen. Suitable allergens include, plant pollens, drugs, foods, venoms, insect excretions, molds, animal fluids, animal hair and animal dander. This method is particularly useful when the mammal has a disease selected from allergic airway diseases, allergic rhinitis, allergic conjunctivitis, and food allergy. Expression of the allergen in a tissue of the mammal produces a result selected from the group consisting of alleviation of the disease, alleviation of symptoms of the disease, desensitization against the disease, and stimulation of a protective immune response against the disease.

In another embodiment of this method, the therapeutic composition comprises a plurality of recombinant nucleic acid molecules, each of the recombinant nucleic acid molecules comprising a cDNA sequence amplified from total RNA isolated from an allergen, each of the cDNA sequences encoding the allergen or a fragment thereof and being operatively linked to a transcription control sequence.

Yet another embodiment of the present invention relates to a method to elicit a systemic, non-specific immune response in a mammal, which includes administering to the mammal a therapeutic composition by a route of administration selected from intravenous and intraperitoneal, wherein the therapeutic composition comprises: (a) a liposome delivery vehicle; and, (b) a recombinant nucleic acid molecule comprising an isolated nucleic acid sequence encoding a cytokine, the nucleic acid sequence being operatively linked to a transcription control sequence. The method of the present invention is particularly useful for eliciting a systemic, anti-viral immune response or a systemic; an anti-tumor immune response; a systemic, protective immune response against allergic inflammation in the mammal; and/or for reduction of a tumor in the mammal. Additionally, the method increases production of IFNγ in the mammal and/or increases natural killer (NK) cell activity in the mammal. In one embodiment, the route of administration is intravenous. The cytokine can include hematopoietic growth factors, interleukins, interferons, immunoglobulin superfamily molecules, tumor necrosis factor family molecules and/or chemokines. In one embodiment, the cytokine is an interleukin, and in a more preferred embodiment, the interleukin is selected from the group of interleukin-2 (IL-2), interleukin-7 (IL-7), interleukin-12 (IL-12), interleukin-15 (IL-15), interleukin-18 (IL-18) or interferon-γ (IFNγ), and in an even more preferred embodiment, the interleukin is selected from the group of interleukin-2 (IL-2), interleukin-12 (IL-12), interleukin-18 (IL-18) or interferon-γ (IFNγ).

Another embodiment of the present invention relates to a method to elicit a tumor antigen-specific immune response and a systemic, non-specific immune response in a mammal that has cancer. The method includes administering to a mammal a therapeutic composition by a route of administration selected from intravenous and intraperitoneal administration. The therapeutic composition comprises: (a) a liposome delivery vehicle; and, (b) total RNA isolated from a tumor sample, the RNA encoding tumor antigens. In one embodiment, the route of administration is intravenous. In another embodiment, the RNA is enriched for poly-A RNA prior to administration to the mammal.

Yet another embodiment of the present invention relates to a method to elicit a pathogen-antigen-specific immune response and a systemic, non-specific immune response in a mammal that has an infectious disease. Such method includes administering to a mammal a therapeutic composition by a route of administration selected from intravenous and intraperitoneal administration, the therapeutic composition comprising: (a) a liposome delivery vehicle; and, (b) total RNA isolated from an infectious disease pathogen, the RNA encoding pathogen antigens. In another embodiment, the route of administration is intravenous.

Another embodiment of the present invention relates to a composition for systemic administration to a mammal to elicit an immunogen-specific immune response and a systemic, non-specific immune response. The composition includes (a) a liposome delivery vehicle; and (b) a recombinant nucleic acid molecule comprising an isolated nucleic acid sequence encoding an immunogen, the nucleic acid sequence being operatively linked to a transcription control sequence. The composition has a nucleic acid:lipid ratio of from about 1:1 to about 1:64.

In one embodiment, any of the above compositions of the present invention administered to a mammal by the present methods can include a recombinant nucleic acid molecule having a nucleic acid sequence encoding a cytokine. In this embodiment, the nucleic acid sequence encoding a cytokine is operatively linked to a transcription control sequence. In the compositions which include a nucleic acid sequence encoding an immunogen, the nucleic acid sequence encoding a cytokine can be in the same or separate recombinant nucleic acid molecule which contains the nucleic acid sequence encoding the immunogen. The nucleic acid sequence-encoding a cytokine and the nucleic acid sequence encoding an immunogen can be operatively linked to the same or different transcription control sequences. In preferred embodiments, the cytokine is selected from the group of hematopoietic growth factors, interleukins, interferons, immunoglobulin superfamily molecules, tumor necrosis factor family molecules and/or chemokines. In one embodiment, the cytokine is an interleukin, and in a more preferred embodiment, the interleukin is selected from the group of interleukin-2 (IL-2), interleukin-7 (IL-7), interleukin-12 (IL-12), interleukin-15 (IL-15), interleukin-18 (IL-18) or interferon-γ (IFNγ), and in an even more preferred embodiment, the interleukin is selected from the group of interleukin-2 (IL-2), interleukin-12 (IL-12), interleukin-18 (IL-18) or interferon-γ (IFNγ).

Liposome delivery vehicles suitable for use in any of the compositions and methods of the present invention can include any liposomes. Particularly preferred liposomes are cationic liposomes. Other preferred liposomes include multilamellar vesicle lipids and extruded lipids, with multilamellar vesicle lipids being more preferred. Liposome compositions can include, but are not limited to, pairs of lipids selected from DOTMA and cholesterol, DOTAP and cholesterol, DOTIM and cholesterol, and DDAB and cholesterol, with DOTAP and cholesterol being particularly preferred.

The compositions of the present invention administered by the present methods have a nucleic acid:lipid ratio of from about 1:1 to about 1:64. In some embodiments, the compositions have a nucleic acid:lipid ratio of from about 1:10 to about 1:40. Other suitable ratios are additionally set forth below.

The methods and compositions of the present invention are preferably used to elicit an immune response in a mammal, which includes humans, dogs, cats, mice, rats, sheep, cattle, horses or pigs, and more preferably, humans.

DETAILED DESCRIPTION OF THE INVENTION

Figure 1:
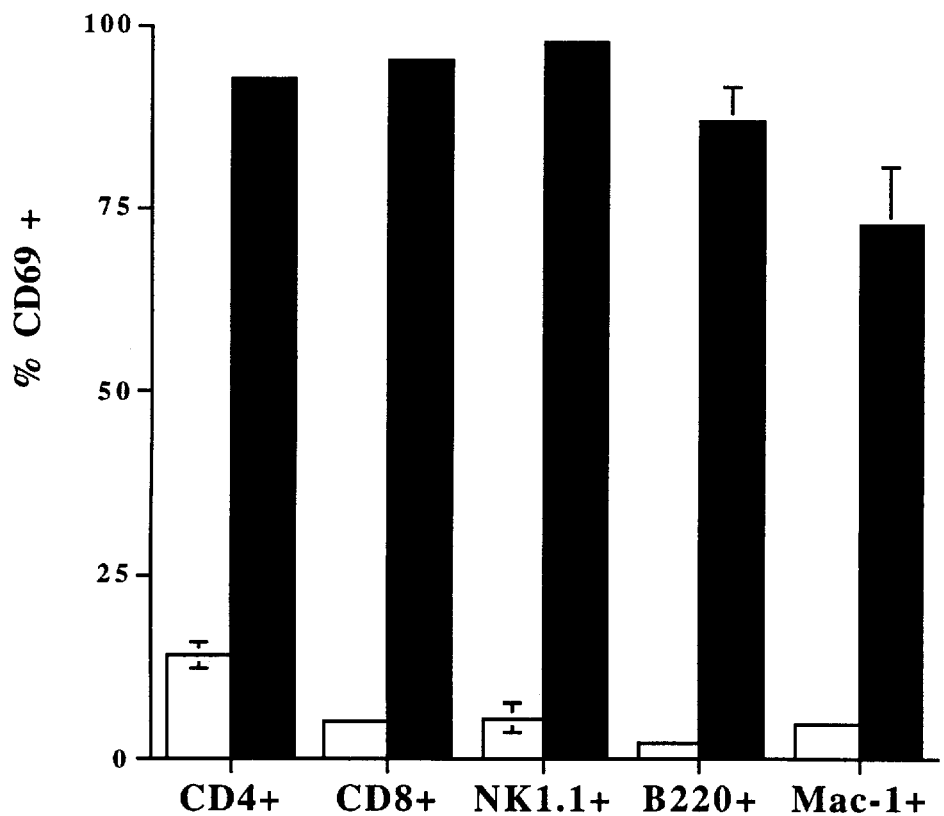
FIG. 1 is a bar graph illustrating that intravenous injection of CLDC induces marked activation of 5 different immune effector populations in vivo.

The present invention generally relates to a novel genetic immunization strategy and therapeutic compositions for eliciting an immune response in a mammal, and in particular, in a mammal that has a disease amenable to treatment by elicitation of an immune response. Diseases which are particularly amenable to treatment using the method of the present invention include cancer, allergic inflammation and infectious disease. In one embodiment, the method and composition of the present invention are particularly useful for the prevention and treatment of primary lung cancers, pulmonary metastatic diseases, allergic asthma and viral diseases. In another embodiment, the method and composition of the present invention are useful for treating chronic obstructive pulmonary diseases. In addition, elicitation of an immune response according to the method of the present invention can be useful for the development and implementation of immunological diagnostic and research tools and assays.

More particularly, the genetic immunization method of the present invention comprises the elicitation of an immune response in a mammal by intravenous or intraperitoneal administration (i.e., systemic administration) of a therapeutic composition which includes an isolated nucleic acid molecule complexed with a liposome delivery vehicle. The present inventors have made the surprising discovery that the combination of nucleic acids and liposomes is highly immunostimulatory in vivo when administered by intravenous or intraperitoneal injection. The potency of this immune response is far greater than the response induced by administration of either nucleic acids or liposomes alone (See Examples 1b, 1h and 2b), and is dependent upon the intravenous or intraperitoneal administration of the complex (See Examples 5 and 6b). Moreover, this effect is independent of whether or not a protein is encoded by or expressed by the nucleic acids (See Examples 1 and 2), and it is also independent of the source of the nucleic acids (e.g., mammalian, bacterial, insect, viral; see Examples 1g and 2c), the type of nucleic acids (e.g., DNA or RNA; see Examples 7a–b), and to some extent, the type of lipids used (See Example 1f). As such, the nucleic acid-lipid complexes of the present invention induce a strong, systemic, non-antigen-specific immune response when administered intravenously or intraperitoneally, which results in the activation of multiple different immune effector cells in vivo. The present inventors have additionally discovered that the immune response generated by such a nucleic acid-lipid complex administered by the present method has potent anti-tumor, anti-allergy and anti-viral properties (See Examples 1a–c, 1h–l, 2a–d, 8 and 9). Immune activation induced by such a therapeutic composition of the present invention is quantitatively more potent than that induced by either LPS (endotoxin) or poly I/C (a classical inducer of antiviral immune responses; see Examples 1c and 1i). Furthermore, the type of immune stimulation induced (e.g., as characterized by the pattern of cytokines induced) also differs qualitatively from that induced by LPS or poly I/C. Finally, this effect does not appear to be associated with the complement cascade problems that have been experienced using viral delivery systems.

These findings are surprising because, prior to the present invention, liposome delivery vehicles, which are often used in gene therapy protocols, were touted by many in the art as being relatively non-immunogenic, particularly as compared to viral vector delivery vehicles (e.g., adenovirus vectors), and have thus been considered safe and useful for delivering a gene to a site in a mammal while substantially avoiding an immune inflammatory response (See, for example, Liu et al., 1997, *Nature Biotechnology* 15:167–173, Stewart et al., 1992, *Hum. Gene Ther.* 3:267–275; Zhu et al., 1993, *Science* 261:209–211; Canonico et al., 1994, *J. Appl. Phys.* 77:415–419). This recognized relative non-immunogenicity of liposomes has motivated those of skill in the art to use liposomes to deliver genes with the confidence that the delivery vehicle is relatively innocuous in vivo. The present invention provides evidence which contradicts this principle.

The discovery of the present inventors is further surprising because, although it was previously recognized that administration of naked DNA (i.e., by intramuscular or percutaneous delivery), which comprises a bacterially derived vector ligated to a target gene, provides an adjuvant effect (i.e., due to the bacterially derived vector DNA), the nucleic acid:lipid complexes of the present invention are significantly more immunostimulatory than DNA administered alone (i.e., naked DNA) (See Examples section). This discovery by the present inventors is quite unexpected and thus represents a new frontier in genetic vaccine design. Previously described naked DNA vaccines are typically designed to use bacterial plasmid DNA, since a vast body of literature has reported that bacterial and some insect nucleic acids may be immunogenic (See, for example, Pisetsky et al., 1996, *Immunity*, 5:303–310; Pisetsky, 1996, *Journal of Immunology* 156:421–423; Yamamoto, et al., 1994, *Microbiol. Immunol.* 38(10):831–836; Roman, et al., 1997, *Nature Medicine*, 3(8):849–854; Krieg, 1996, *Trends in Microbiology*, 4(2):73–77; Sun, et al., 1996, *Immunity*, 4:555–564; Stacey et al., 1996, *The Journal of Immunology*, 157:2116–2122; Sato, et al., 1996, *Science*, 273:352–354; or Ballas, 1996, *The Journal of Immunology*, 157:1840–1845). Significantly, this literature has specifically excluded mammalian nucleic acids for use in naked DNA vaccines, asserting that mammalian nucleic acids are not immunogenic. Therefore, it is completely unpredicted by the art at the time of the present invention that nucleic acids from mammalian sources would have immunostimulatory properties, and it is even more unexpected that the effect of nucleic acids from any source complexed with lipids at very low doses would synergize to provide such a strong immunostimulatory effect demonstrated by the present inventors, particularly in comparison to lipids or nucleic acids alone.

In view of the present inventors' discoveries, previous investigators in the art may be misdirecting the use of liposome delivery vehicles for gene therapy when elicitation of an immune response is not desirable. Moreover, with regard to genetic immunization, which is the primary focus of the present invention, previous investigators have not taken advantage of the superior immunostimulatory effect of nucleic acid:lipid complexes in designing genetic vaccines. In fact, most of the disclosed specific genetic immunization strategies do not make use of liposome delivery and/or are administered by intramuscular, intradermal, oral or aerosol delivery routes, for the reasons discussed above.

The present inventors disclose herein that alternate, non-systemic routes of administration (i.e., other than intravenous or intraperitoneal) significantly decrease both the immunostimulatory effect and the therapeutic efficacy of the present composition in comparison with administration by the present method. Specifically, the present inventors have found that the efficacy of the genetic immunization method of the present invention is unattainable using previously described genetic immunization protocols wherein naked DNA is delivered intramuscularly or percutaneously, even when such protocols use 10 to 100 times more DNA than the present method (See Example 5 and 6b–c). The present inventors' discovery is surprising, because there was no suggestion in any genetic immunization disclosure that the particular genetic immunization protocol of the present invention would be considerably more efficacious than other possible protocols.

When the route of administration is intravenous, the primary site of immunization (i.e., elicitation of an;immune response) is the lung, which is a very active organ immunologically, containing large numbers of both effector cells (e.g., T cells, B cells, NK cells) and antigen presenting cells (e.g., macrophages, dendritic cells). Similarly, when the route of administration E is intraperitoneal, the primary sites of immunization are the spleen and liver, both of which are also immunologically active organs. Without being bound by theory, the present inventors believe that these organs are capable of mounting a robust, non-antigen-specific immune response both in the tissues and systemically, due to the mode of administration. Additionally, when the nucleic acid molecules of the nucleic acid:lipid complex encode and express an immunogen, these organs are further capable of expressing the immunogen and mounting a strong antigen-specific immune response against antigens that are encountered within the tissues. These activated immune cells are then capable of eliciting an immune response in other areas of the body in which the appropriate antigen is encountered. Administration of the nucleic acid:lipid complexes can be at any site in the mammal wherein systemic administration (i.e., intravenous or intraperitoneal administration) is possible, including to sites in which the target site for immune activation is not the first organ having a capillary bed proximal to the site of administration.

As discussed above, the use of genetic vaccines and gene therapy vehicles has generally been described in the art (See for example, U.S. Pat. No. 5,593,972, issued Jan. 14, 1997, to Weiner et al.; U.S. Pat. No. 5,580,859, issued Dec. 3, 1996, to Felgner et al.; U.S. Pat. No. 5,589,466, issued Dec. 31, 1996, to Felgner et al.; U.S. Pat. No. 5,641,662, issued Jun. 24, 1997, to Debs et al. and U.S. Pat. No. 5,676,954, issued Oct. 14, 1997, to Brigham). Such publications have broadly disclosed genetic vaccine and/or gene therapy protocols which include administration of nucleic acid molecules (e.g., DNA) encoding any of a variety of antigens and other proteins, which are administered to an animal by a variety of administration routes, and using a variety of delivery mechanisms. These disclosures have failed, however, to appreciate the surprising advantages and unexpected efficacy of the particular genetic immunization compositions and methods discovered by the present inventors. Indeed, in view of the above discussion, many of the methods and compositions for genetic immunization and/or gene therapy disclosed by the above publications are predicted to be inoperable, unsafe, and/or significantly less effective in vivo than the specific compositions and methods of the present invention. The present inventors' discoveries provide strong evidence that the development of both genetic vaccines designed to immunize an animal and gene therapy protocols designed to deliver a gene to a site in an animal should be reevaluated to avoid previously unknown safety and efficacy concerns.

Due to the unexpected immunostimulatory properties of the nucleic acid:lipid complexes administered by the present method, the genetic immunization method of the present invention is particularly useful in human treatments because traditional adjuvants can be avoided. This is a particular advantage of the present method, since some traditional adjuvants can be toxic (e.g., Freund's adjuvant and other bacterial cell wall components) and others are relatively ineffective (e.g., aluminum-based salts and calcium-based salts). Moreover, the only adjuvants currently approved for use in humans in the United States are the aluminum salts, aluminum hydroxide and aluminum phosphate, neither of which stimulates cell-mediated immunity. In addition, as will be shown in the Examples below, traditional naked DNA delivery, which has been touted as having an adjuvant effect, is far less effective than the present compositions at stimulating a non-antigen-specific immune response. Finally, unlike many protocols for administration of viral vector-based genetic vaccines, the present method can be used to repeatedly deliver the therapeutic composition described herein without consequences associated with some non-specific arms of the immune response, such as the complement cascade.

In further embodiments of the present invention, the present inventors have taken advantage of the non-antigen-specific immunostimulatory effect of the above-described method and have developed an even more powerful genetic immunization strategy in which a nucleic acid sequence in the above nucleic acid-lipid complex encodes an immunogen and/or a cytokine that is expressed in the tissues of the mammal (i.e., is operatively linked to a transcription control sequence; see Examples 4–9). The present inventors have also found that the combination of an antigen-specific immune response elicited by expression of an immunogen, in conjunction with the powerful, non-antigen specific immune response elicited by the nucleic acid:lipid complex results in a vaccine that has significantly greater in vivo efficacy than previously described genetic vaccines (See Examples 5, 6b–c, 9). This effect can be additionally enhanced by coadministration of a nucleic acid molecule encoding a cytokine such that the cytokine is expressed in the tissues (See Examples 4 and 7a).

Moreover, with regard to intravenous administration of the present composition, in cancer patients, the lung is the principal site to which metastatic tumors spread. The method of the present invention is particularly successful in mammals having cancer, because it induces a strong enough immune response to reduce or eliminate a primary tumor and to control any metastatic tumors that are already present, including large metastatic tumors. Therefore, the genetic immunization method and compositions of the present invention, unlike previously described genetic immunization methods, elicit both a systemic, non-antigen-specific immune response (similar to a conventional adjuvant) and, when the nucleic acid encodes a tumor antigen, a strong, antigen-specific, intrapulmonary (intravenous administration; see Examples 1e, 3 and 5) or splenic and/or hepatic (intraperitoneal administration; see Examples 1e and 11) immune response in a mammal which is effective to significantly reduce or eliminate established tumors in vivo.

One embodiment of the present invention is a method to elicit a systemic, non-antigen-specific immune response in a mammal immune response in a mammal. In this method, a therapeutic composition which includes: (a) a liposome delivery vehicle; and (b) an isolated nucleic acid molecule that is not operatively linked to a transcription control sequence, is administered by intravenous or intraperitoneal administration to a mammal. Administration of, such a composition by the method of the present invention results in the elicitation of a systemic, non-antigen-specific immune response in the mammal to which the composition is administered. As discussed above, this immune response additionally has strong, systemic, anti-tumor, anti-allergic inflammation (i.e., protective), and anti-viral properties. Such properties include the activation of NK cells (as measured by upregulation of NK cell markers, such as NK1.1, for example, or by production of IFNγ), production of Th1-type cytokines (e.g., IFNγ) and the non-antigen-specific recruitment and upregulation of activity in mononuclear cells and T lymphocytes.

Therapeutic compositions useful in the method of the present invention include compositions containing nucleic acids having any nucleic acid sequence, including coding (i.e. encoding at least a portion of a protein or peptide) and/or non-coding (i.e., not encoding any portion of a protein or peptide) sequences, and including DNA and/or RNA. In the above-described embodiment of the present invention, since expression of a protein encoded by the nucleic acid molecule is not required for elicitation of a systemic, non-antigen-specific immune response, the molecule is not necessarily operatively linked to a transcription control sequence. It is to be noted, however, that further advantages can be obtained (i.e., antigen-specific and enhanced immunity) by including in the composition a nucleic acid sequence (DNA or RNA) which encodes an immunogen and/or a cytokine.

In another embodiment of the present invention, the present method of eliciting an immune response can be modified to include the intravenous or intraperitoneal administration to a mammal of a therapeutic composition comprising: (a) a liposome delivery vehicle; and (b) a recombinant nucleic acid molecule comprising a nucleic acid sequence which encodes an immunogen. According to the present invention, the terms "immunogen" and "antigen" can be used interchangeably, although the term "antigen" is primarily used herein to describe a protein which elicits a humoral and/or cellular immune response (i.e., is antigenic), and the term "immunogen" is primarily used herein to describe a protein which elicits a humoral and/or cellular immune response in vivo, such that administration of the immunogen to a mammal mounts an immunogen-specific (antigen-specific) immune response against the same or similar proteins that are encountered within the tissues of the mammal. According to the present invention, an immunogen or an antigen can be any portion of a protein, naturally occurring or synthetically derived, which elicits a humoral and/or cellular immune response. As such, the size of an antigen or immunogen can be as small as about 5–12 amino acids and as large as a full length protein, including a multimer and fusion proteins. The terms, "immunogen" and "antigen", as used to describe the present invention, do not include a superantigen. A superantigen is defined herein as the art-recognized term. More particularly, a superantigen is a molecule within a family of proteins that binds to the extracellular portion of an MHC molecule (i.e., not in the peptide binding groove) to form and MHC:superantigen complex. The activity of a T cell can be modified when a TCR binds to an MHC:superantigen complex. Under certain circumstances, an MHC:superantigen complex can have a mitogenic role (i.e., the ability to stimulate the proliferation of T cells) or a suppressive role (i.e., deletion of T cell subsets).

In preferred embodiments, the immunogen is selected from the group of a tumor antigen, an allergen or an antigen of an infectious disease pathogen (i.e., a pathogen antigen). In this embodiment, the nucleic acid sequence is operatively linked to a transcription control sequence, such that the immunogen is expressed in a tissue of a mammal, thereby eliciting an immunogen-specific immune response in the mammal, in addition to the non-specific immune response discussed above.

In a further embodiment of the method of the present invention, the therapeutic composition to be administered to a mammal includes an isolated nucleic acid molecule encoding a cytokine (also referred to herein as a "cytokine-encoding nucleic acid molecule"), in which the nucleic acid molecule is operatively linked to one or more transcription control sequences. The result of administration of such a therapeutic composition to the mammal is that the nucleic acid molecule encoding the cytokine is expressed in the pulmonary tissues of the mammal, when administration is intravenous, and in the spleen and liver tissues of the mammal when administration is peritoneal. It is to be noted that the term "a" or "an" entity refers to one or more of that entity; for example, a cytokine refers to one or more cytokines. As such, the terms "a" (or "an"), "one or more" and "at least one" can be used interchangeably herein. The nucleic acid sequence encoding a cytokine can be on the same recombinant nucleic acid molecule as a nucleic acid sequence encoding an immunogen, or on a different recombinant nucleic acid molecule.

A composition useful in the method of the present invention, as discussed in detail below, comprises: (a) a liposome delivery vehicle; and (b) a nucleic acid molecule, such molecule including: (1) an isolated nucleic acid sequence that is not operatively linked to a transcription control sequence; (2) an isolated non-coding nucleic acid sequence; (3) an isolated recombinant nucleic acid molecule encoding an immunogen operatively linked to a transcription control sequence, wherein the nucleic acid:lipid complex has a ratio of from about 1:1 to about 1:64; and/or (4) an isolated recombinant nucleic acid molecule encoding a cytokine. In preferred embodiments, the nucleic acid:lipid complex has a ratio of from about 1:10 to 1:40. Various components of such a composition are described in detail below.

Elicitation of an immune response in a mammal can be an effective treatment for a wide variety of medical disorders, and in particular, for cancer, allergic inflammation and/or infectious disease. As used herein, the term "elicit" can be used interchangeably with the terms "activate", "stimulate", "generate" or "upregulate". According to the present invention, "eliciting an immune response" in a mammal refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a mammal from one which is harmful or ineffective to one which is beneficial or protective. For example, elicitation of a Th1-type response in a mammal that is undergoing a Th2-type response, or vice versa, may change the overall effect of the immune response from harmful to beneficial. Eliciting an immune response which alters the overall immune response in a mammal can be particularly effective in the treatment of allergic inflammation, mycobacterial infections, or parasitic infections. According to the present invention, a disease characterized by a Th2-type immune response (alternatively referred to as a Th2 immune response), can be characterized as a disease which is associated with the predominant activation of a subset of helper T lymphocytes known in the art as Th2-type T lymphocytes (or Th2 lymphocytes), as compared to the activation of Th1-type T lymphocytes (or Th1 lymphocytes). According to the present invention, Th2-type T lymphocytes can be characterized by their production of one or more cytokines, collectively known as Th2-type cytokines. As used herein, Th2-type cytokines include interleukin-4 (IL-4), interleukin-5 (IL-5), interleukin-6 (IL-6), interleukin-9 (IL-9), interleukin-10 (IL-10), interleukin-13 (IL-13) and interleukin-15 (IL-15). In contrast, Th1-type lymphocytes produce cytokines which include IL-2 and IFNγ. Alternatively, a Th2-type immune response can sometimes be characterized by the predominant production of antibody isotypes which include IgG1 (the approximate human equivalent of which is IgG4) and IgE, whereas a Th1-type immune response can sometimes be characterized by the production of an IgG2a or an IgG3 antibody isotype (the approximate human equivalent of which is IgG1, IgG2 or IgG3).

Preferably, the method of the present invention elicits an immune response against a tumor, an allergen or an infectious disease pathogen. In particular, eliciting an immune response in a mammal refers to regulating cell-mediated immunity (i.e., helper T cell (Th) activity, cytotoxic T lymphocyte (CTL) activity, NK cell activity) and/or humoral immunity (i.e., B cell/immunoglobulin activity), including Th1-type and/or Th2-type cellular and/or humoral activity. In a preferred embodiment, the method of the present invention increases or elicits effector cell immunity against a tumor, an allergen or an infectious disease pathogen. As used herein, effector cell immunity refers to increasing the number and/or the activity of effector cells in the mammal to which a composition is administered. In particular, T cell activity refers to increasing the number and/or the activity of T cells in the area of the tumor cell or pathogen. Similarly, NK cell activity refers to increasing the number and/or activity of NK cells. In the method of the present invention, effector cell immunity is elicited both systemically and in the area of the mammal in which the therapeutic composition is primarily targeted (i.e., intrapulmonary for intravenous administration and in the spleen or liver for intraperitoneal administration, although the present composition is effective at other sites in the body as well). According to the present invention, an effector cell includes a helper T cell, a cytotoxic T cell, a B lymphocyte, a macrophage, a monocyte and/or a natural killer cell. For example, the method of the present invention can be performed to increase the number of effector cells in a mammal that are capable of killing a target cell or releasing cytokines when presented with antigens derived from a tumor cell, an allergen or a pathogen.

Figure 10A:
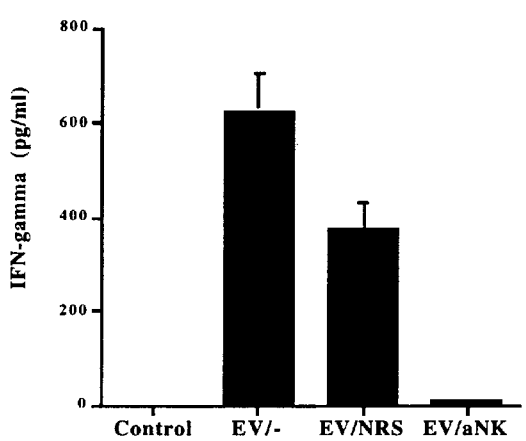
FIG. 10A is a bar graph showing that NK cells are the source of IFNγ production in splenocytes elicited by i.v. administration of CLDC injection.
Figure 10B:
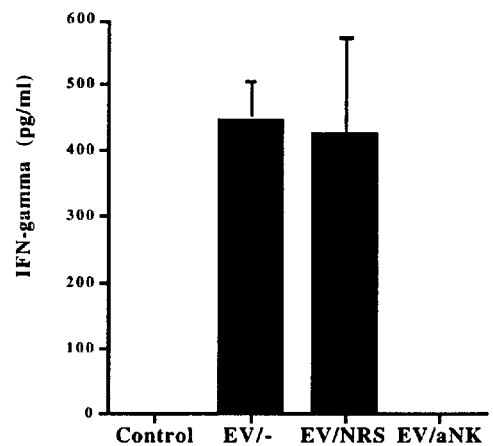
FIG. 10B is a bar graph showing that NK cells are the source of IFNγ production in lung mononuclear cells elicited by i.v. administration of CLDC injection.
Figure 11:
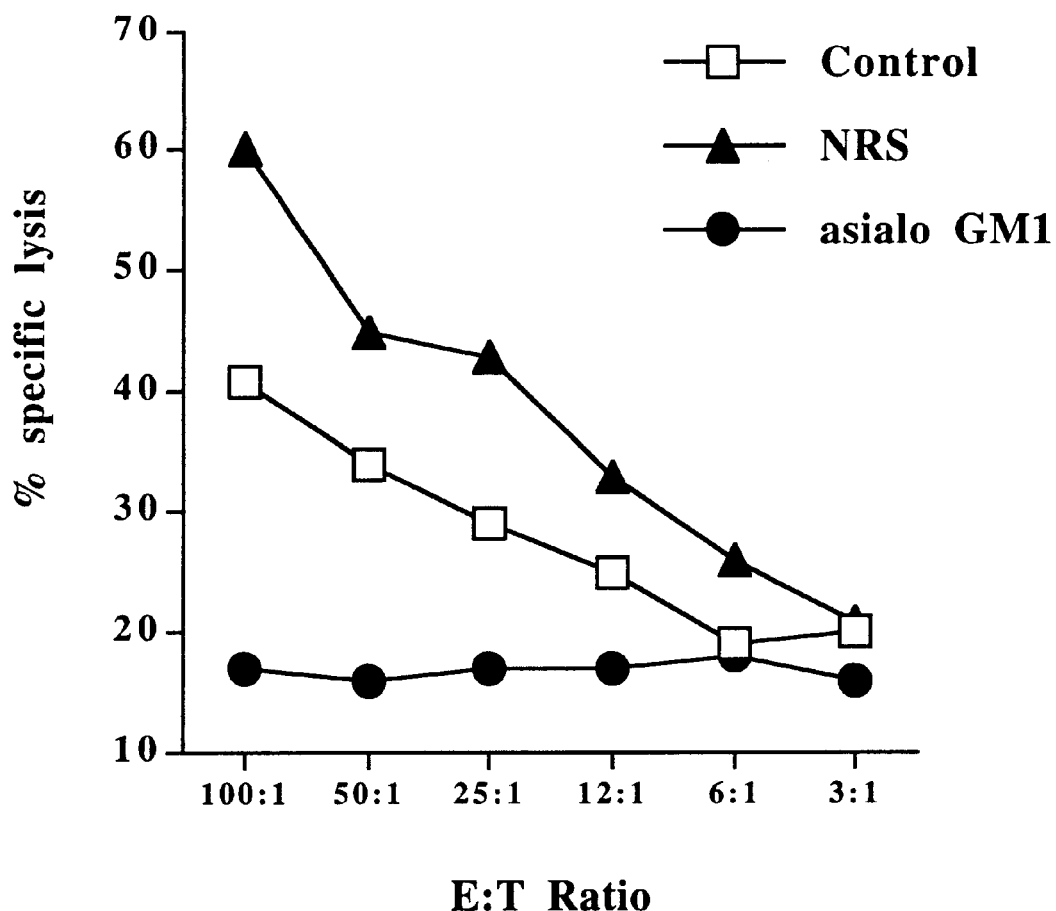
FIG. 11 is a line graph illustrating that administration of CLDC induces high levels of NK activity in splenocytes.

According to the present invention, elicitation of a non-antigen-specific immune response (i.e., a non-specific immune response) includes stimulation of non-specific immune cells, such as macrophages and neutrophils, as well as induction of cytokine production, particularly IFNγ production, and non-antigen-specific activation of effector cells such as NK cells, B lymphocytes and/or T lymphocytes. More specifically, the systemic, non-antigen-specific immune response elicited by the method and composition of the present invention result in an increase in natural killer (NK) cell function and number in the mammal, wherein an increase in NK function is defined as any detectable increase in the level of NK cell function compared to NK cell function in mammals not immunized with a composition of the present invention, or in mammals immunized with a composition of the present invention by a non-systemic (i.e., non-intravenous, non-intraperitoneal) route of administration, with the amount of nucleic acid delivered and the ratio of nucleic acid:lipid being equal. NK function (i.e., activity) can be measured by cytotoxicity assays against a suitable target cell. An example of a suitable target cell by which to measure NK cell cytotoxic activity is YAC-1. An example of an NK cell cytotoxicity assay is presented in Example 1 (FIG. 11). NK cell activation can be measured by determining an upregulation of NK1.1/CD69 on cells in various organs, including spleen, lymph node, lung and liver, by flow cytometric analysis (See Example 1, FIGS. 1 and 2). Additionally, the systemic, non-antigen-specific immune response elicited by the method and composition of the present invention can result in an increase in production of IFNγ by the NK cells in the mammal in various organs including spleen and lung, wherein an increase in IFNγ production is defined as any detectable increase in the level of IFNγ production compared to IFNγ production by NK cells in mammals not administered with a composition of the present invention, or in mammals administered with a composition of the present invention by a non-systemic route of administration, with the amount of nucleic acid delivered and the ratio of nucleic acid:lipid being equal. IFNγ production can be measured by a IFNγ ELISA (as is known in the art; Example 1, FIG. 10). Preferably, a composition of the present invention administered by the method of the present invention elicits at least about 100 pg/ml of IFNγ per $5\times10^6$ mononuclear cells from blood, spleen or lung, and more preferably, at least about 500 pg/ml of IFNγ, and more preferably at least about 1000 pg/ml of IFNγ, and even more preferably, at least about 5000 pg/ml of IFNγ, and even more preferably, at least about 10,000 pg/ml of IFNγ.

Accordingly, the method of the present invention preferably elicits an immune response in a mammal such that the mammal is protected from a disease that is amenable to elicitation of an immune response, including cancer, allergic inflammation and/or an infectious disease. As used herein, the phrase "protected from a disease" refers to reducing the symptoms of the disease; reducing the occurrence of the disease, and/or reducing the severity of the disease. Protecting a mammal can refer to the ability of a therapeutic composition of the present invention, when administered to a mammal, to prevent a disease from occurring and/or to cure or to alleviate disease symptoms, signs or causes. As such, to protect a mammal from a disease includes both preventing disease occurrence (prophylactic treatment) and treating a mammal that has a disease (therapeutic treatment). In particular, protecting a mammal from a disease is accomplished by eliciting an immune response in the mammal by inducing a beneficial or protective immune response which may, in some instances, additionally suppress (e.g., reduce, inhibit or block) an overactive or harmful immune response. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

More specifically, a therapeutic composition as described herein, when administered to a mammal by the method of the present invention, preferably produces a result which can include alleviation of the disease, elimination of the disease, reduction of a tumor or lesion associated with the disease, elimination of a tumor or lesion associated with the disease, prevention of a secondary disease resulting from the occurrence of a primary disease (e.g., metastatic cancer resulting from a primary cancer), prevention of the disease, and stimulation of effector cell immunity against the disease.

One component of the therapeutic composition used in the present method is a nucleic acid sequence, which can include coding and/or non-coding nucleic acid sequences, and both oligonucleotides (described below) and larger nucleic acid sequences. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. As used herein, a "coding" nucleic acid sequence refers to a nucleic acid sequence which encodes at least a portion of a peptide or protein (e.g. a portion of an open reading frame), and can more particularly refer to a nucleic acid sequence encoding a peptide or protein which is operatively linked to a transcription control sequence, so that the peptide or protein can be expressed. A "non-coding" nucleic acid sequence refers to a nucleic acid sequence which does not encode any portion of a peptide or protein. According to the present invention, "non-coding" nucleic acids can include regulatory regions of a transcription unit, such as a promoter region. The term, "empty vector" can be used interchangeably with the term "non-coding", and particularly refers to a nucleic acid sequence in the absence of a protein coding portion, such as a plasmid vector without a gene insert. The phrase "operatively linked" refers to linking a nucleic acid molecule to a transcription control sequence in a manner such that the molecule is able to be expressed when transfected (i.e., transformed, transduced or transfected) into a host cell. Therefore, a nucleic acid sequence that is "not operatively linked to a transcription control sequence" refers to any nucleic acid sequence, including both coding and non-coding nucleic acid sequences, which are not linked to a transcription control sequence in a manner such that the molecule is able to be expressed when transfected into a host cell. It is noted that this phrase does not preclude the presence of a transcription control sequence in the nucleic acid molecule.

In some embodiments of the present invention, a nucleic acid sequence included in a therapeutic composition of the present invention is incorporated into a recombinant nucleic acid molecule, and encodes an immunogen and/or a cytokine. As discussed in detail below, preferred immunogens include a tumor antigen, an allergen or an antigen from an infectious disease pathogen (i.e., a pathogen antigen). The phrase "recombinant molecule" primarily refers to a nucleic acid molecule or nucleic acid sequence operatively linked to a transcription control sequence, but can be used interchangeably with the phrase "nucleic acid molecule" which is administered to a mammal.

According to the present invention, an isolated, or biologically pure, nucleic acid molecule or nucleic acid sequence, is a nucleic acid molecule or sequence that has been removed from its natural milieu. As such, "isolated" and "biologically pure" do not necessarily reflect the extent to which the nucleic acid molecule has been purified. An isolated nucleic acid molecule useful in the present composition can include DNA, RNA, or derivatives of either DNA or RNA. An isolated nucleic acid molecule useful in the present composition can include oligonucleotides and larger sequences, including both nucleic acid molecules that encode a protein or a fragment thereof, and nucleic acid molecules that comprise regulatory regions, introns, or other non-coding DNA or RNA. Typically, an oligonucleotide has a nucleic acid sequence from about 1 to about 500 nucleotides, and more typically, is at least about 5 nucleotides in length. Immune activation by nucleic acid:lipid complexes of the present invention can be induced by eukaryotic as well as prokaryotic nucleic acids, indicating that there is some property of the nucleic acid:lipid complexes that is inherently immune activating, regardless of the source of the nucleic acids. Therefore, the nucleic acid molecule can be derived from any source, including mammalian, bacterial, insect, or viral sources, since the present inventors have discovered that the source of the nucleic acid does not have a significant effect on the ability to elicit an immune response by the nucleic acid-lipid complex. In one embodiment of the present invention, the nucleic acid molecule used in a therapeutic composition of the present invention is not a bacterial nucleic acid molecule.

An isolated immunogen-encoding (e.g., a tumor antigen-, allergen-, or pathogen antigen-) or cytokine-encoding nucleic acid molecule can be obtained from its natural source, either as an entire (i.e., complete) gene or a portion thereof capable of encoding: a tumor antigen protein having a B cell and/or T cell epitope, an allergen having a B cell and/or T cell epitope, a pathogen antigen having a B cell and/or a T cell epitope, or a cytokine protein capable of binding to a complementary cytokine receptor. A nucleic acid molecule can also be produced using recombinant DNA technology (e.g., polymerase chain reaction (PCR) amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an immunogen or a cytokine useful in the method of the present invention.

A nucleic acid molecule homologue can be produced using a number of methods known to those skilled in the art (see, for example, Sambrook et al., *Molecular Cloning: A Laboratory Manual*, Cold Spring Harbor Labs Press, 1989), which is incorporated herein by reference in its entirety. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., tumor antigen, allergen or pathogen antigen immunogenicity, or cytokine activity, as appropriate). Techniques to screen for immunogenicity, such as tumor antigen, allergen or pathogen antigen immunogenicity, or cytokine activity, are known to those of skill in the art and include a variety of in vitro and in vivo assays.

As heretofore disclosed, immunogen or cytokine proteins of the present invention include, but are not limited to, proteins encoded by nucleic acid molecules having full-length immunogen or cytokine coding regions; proteins encoded by nucleic acid molecules having partial immunogen regions which contain at least one T cell epitope and/or at least one B cell epitope; proteins encoded by nucleic acid molecules having cytokine coding regions capable of binding to a complementary cytokine receptor; fusion proteins; and chimeric proteins comprising combinations of different immunogens and/or cytokines.

One embodiment of the present invention is an isolated nucleic acid molecule that encodes at least a portion of a full-length immunogen, including a tumor antigen, allergen or pathogen antigen, or a homologue of such immunogens. As used herein, "at least a portion of an immunogen" refers to a portion of an immunogen protein containing a T cell and/or a B cell epitope. In one embodiment, an immunogen-encoding nucleic acid molecule includes an entire coding region of such an immunogen. As used herein, a homologue of an immunogen is a protein having an amino acid sequence that is sufficiently similar to a natural immunogen amino acid sequence (i.e., a naturally occurring, endogenous, or wild-type immunogen) that a nucleic acid sequence encoding the homologue encodes a protein capable of eliciting an immune response against the natural immunogen.

A tumor antigen-encoding nucleic acid molecule of the present invention encodes an antigen that can include tumor antigens having epitopes that are recognized by T cells, tumor antigens having epitopes that are recognized by B cells, tumor antigens that are exclusively expressed by tumor cells, and tumor antigens that are expressed by tumor cells and by non-tumor cells. Preferably, tumor antigens useful in the present. method have at least one T cell and/or B cell epitope. Therefore, expression of the tumor antigen in a tissue of a mammal elicits a tumor antigen-specific immune response against the tumor in the tissue of the mammal. As discussed above, the present inventors have found that administration of the nucleic acid:lipid complex of the present invention elicits a strong, systemic, non-antigen-specific, anti-tumor response in vivo, and this effect enhances the antigen-specific immune response to a tumor antigen expressed by the nucleic acid molecule.

In a preferred embodiment, a nucleic acid molecule of the present invention encodes a tumor antigen from a cancer selected from the group of melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof.

According to the present invention, a pathogen antigen-encoding nucleic acid molecule of the present invention encodes an antigen from an infectious disease pathogen that can include pathogen antigens having epitopes that are recognized by T cells, pathogen antigens having epitopes that are recognized by B cells, pathogen antigens that are exclusively expressed by pathogens, and pathogen antigens that are expressed by pathogens and by other cells. Preferably, pathogen antigens useful in the present method have at least one T cell and/or B cell epitope and are exclusively expressed by pathogens (i.e., and not by the endogenous tissues of the infected mammal). Therefore, expression of the pathogen antigen in a tissue of a mammal elicits an antigen-specific immune response against the pathogen in the tissues of the mammal as well as systemically.

According to the present invention, a pathogen antigen includes an antigen that is expressed by a bacterium, a virus, a parasite or a fungus. Preferred pathogen antigens for use in the method of the present invention include antigens which cause a chronic infectious disease in a mammal. Particularly preferred pathogen antigens for use in the present method are immunogens from immunodeficiency virus (HIV), *Mycobacterium tuberculosis*, herpesvirus, papillomavirus and Candida.

In one embodiment, a pathogen antigen for use in the method or composition of the present invention includes an antigen from a pathogen associated with an infectious pulmonary disease, such as tuberculosis. In a more preferred embodiment, such a pathogen antigen includes an antigen from *Mycobacterium tuberculosis*, and even more preferably, is *Mycobacterium tuberculosis* antigen 85.

In another embodiment of the present invention, a pathogen antigen for use in the method or composition of the present invention includes an immunogen from a virus. As discussed above, the present inventors have found that the composition and method of the present invention are particularly useful in the treatment of and protection against viral infections. Specifically, the nucleic acid:lipid complex administered by the method of the present invention elicits a strong, systemic, non-antigen-specific, anti-viral response in vivo, regardless of whether or not the nucleic acid encodes or expresses an immunogen. When the nucleic acid sequence does encode a viral antigen that is operatively linked to a transcription control sequence such that the viral antigen is expressed in a tissue of a mammal, the present composition further elicits a strong, viral antigen-specific immune response in addition to the above-described systemic immune response. In a preferred embodiment, the immunogen is from a virus selected from the group of human immunodeficiency virus and feline immunodeficiency virus.

Another embodiment of the present invention includes an allergen-encoding nucleic acid molecule that encodes at least a portion of a full-length allergen or a homologue of the allergen protein, and includes allergens having epitopes that are recognized by T cells, allergens having epitopes that are recognized by B cells, and allergens that are a sensitizing agent in diseases associated with allergic inflammation. Preferred allergens to use in the therapeutic composition of the present invention include plant pollens, drugs, foods, venoms, insect excretions, molds, animal fluids, animal hair and animal dander.

Another embodiment of the present invention includes a cytokine-encoding nucleic acid molecule that encodes at least a portion of a full-length cytokine or a homologue of the cytokine protein. As used herein, "at least a portion of a cytokine" refers to a portion of a cytokine protein having cytokine activity and being capable of binding to a cytokine receptor. Preferably, a cytokine-encoding nucleic acid molecule includes an entire coding region of a cytokine. As used herein, a homologue of a cytokine is a protein having an amino acid sequence that is sufficiently similar to a natural cytokine amino acid sequence so as to have cytokine activity (i.e. activity associated with naturally occurring, or wild-type cytokines). In accordance with the present invention, a cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell.

A cytokine-encoding nucleic acid molecule of the present invention encodes a cytokine that is capable of affecting the biological function of a cell, including, but not limited to, a lymphocyte, a muscle cell, a hematopoietic precursor cell, a mast cell, a natural killer cell, a macrophage, a monocyte, an epithelial cell, an endothelial cell, a dendritic cell, a mesenchymal cell, a Langerhans cell, cells found in granulomas and tumor cells of any cellular origin, and more preferably a mesenchymal cell, an epithelial cell, an endothelial cell, a muscle cell, a macrophage, a monocyte, a T cell and a dendritic cell.

A preferred cytokine nucleic acid molecule of the present invention encodes a hematopoietic growth factor, an interleukin, an interferon, an immunoglobulin superfamily molecule, a tumor necrosis factor family molecule and/or a chemokine (i.e., a protein that regulates the migration and activation of cells, particularly phagocytic cells). A more preferred cytokine nucleic acid molecule of the present invention encodes an interleukin. An even more preferred cytokine nucleic acid molecule useful in the method of the present invention encodes interleukin-2 (IL-2), interleukin-7 (IL-7), interleukin-12 (IL-12), interleukin-15 (IL-15), interleukin-18 (IL-18), and/or interferon-γ (IFNγ). A most preferred cytokine nucleic acid molecule useful in the method of the present invention encodes interleukin-2 (IL-2), interleukin-12 (IL-12), interleukin-18 (IL-18) and/or interferon-γ (IFNγ).

As will be apparent to one of skill in the art, the present invention is intended to apply to cytokines derived from all types of mammals. A preferred mammal from which to derive cytokines includes a mouse, a human and a domestic pet (e.g., dog, cat). A more preferred mammal from which to derive cytokines includes a dog and a human. An even more preferred mammal from which to derive cytokines is a human.

According to the present invention, a cytokine-encoding nucleic acid molecule of the present invention is preferably derived from the same species of mammal as the mammal to be treated. For example, a cytokine-encoding nucleic acid molecule derived from a canine (i.e., dog) nucleic acid molecule is preferably used to treat a disease in a canine.

The present invention includes a nucleic acid molecule of the present invention operatively linked to one or more transcription control sequences to form a recombinant molecule. As discussed above, the phrase "operatively linked" refers to linking a nucleic acid molecule to a transcription control sequence in a manner such that the molecule is able to be expressed when transfected (i.e., transformed, transduced or transfected) into a host cell. Preferably, a nucleic acid molecule used in a composition of the present invention is operatively linked to a transcription control sequence which allows for transient expression of the molecule in the recipient mammal. To avoid adverse affects of prolonged immune activation (e.g., shock, excessive inflammation, immune tolerance), it is a preferred embodiment of the present invention that an immunogen or cytokine encoded by a nucleic acid molecule be expressed in the immunized mammal for about 72 hours to about 1 month, and preferably, from about 1 week to about 1 month, and more preferably, from about 2 weeks to about 1 month. Expression of a longer period of time than 1 month is not desired in instances where undesirable effects associated with prolonged immune activation occur. However, if such effects do not occur for a particular composition or can be avoided or controlled, then extended expression is acceptable. In one embodiment, transient expression can be achieved by selection of suitable transcription control sequences, for example. Transcription control sequences which are suitable for transient gene expression are discussed below.

Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful in the method of the present invention. A variety of such transcription control sequences are known to those skilled in the art. Preferred transcription control sequences include those which function in mammalian, bacteria, insect cells, and preferably in mammalian cells. More preferred transcription control sequences include, but are not limited to, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus and other poxviruses, herpesvirus, and adenovirus transcription control sequences, as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding an immunogen, including tumor antigen, an allergen, a pathogen antigen or a cytokine.

Particularly preferred transcription control sequences for use in the present invention include promoters which allow for transient expression of a nucleic acid molecule that is to be expressed, thereby allowing for expression of the protein encoded by the nucleic acid molecule to be terminated after a time sufficient to elicit an immune response. Adverse effects related to prolonged activation of the immune system can be avoided by selection of promoters and other transcription control factors which allow for transient expression of a nucleic acid molecule. This is yet another point of difference between the method of the present invention and previously described gene therapy/gene replacement protocols. Suitable promoters for use with nucleic acid molecules encoding immunogens and/or cytokines for use in the present invention include cytomegalovirus (CMV) promoter and other non-retroviral virus-based promoters such as RSV promoters, adenovirus promoters and Simian virus promoters. LTR, tissue-specific promoters, promoters from self-replication viruses and papillomavirus promoters, which may be quite desirable in gene therapy/gene replacement protocols because they provide prolonged expression of a transgene, are not preferred transcription control sequences for use in the present invention.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed immunogen or cytokine protein to be secreted from the cell that produces the protein. Suitable signal segments include: (1) an immunogen signal segment (e.g., a tumor antigen, allergen or pathogen antigen signal segment); (2) a cytokine signal segment; (3) or any heterologous signal segment capable of directing the secretion of an immunogen and/or cytokine protein according to the present invention.

Preferred recombinant molecules of the present invention include a recombinant molecule containing a nucleic acid sequence encoding an immunogen, a recombinant molecule containing a nucleic acid sequence encoding a cytokine, or a recombinant molecule containing both a nucleic acid sequence encoding an immunogen and a nucleic acid sequence encoding a cytokine to form a chimeric recombinant molecule (i.e., the nucleic acid sequence encoding the immunogen and the nucleic acid sequence encoding the cytokine are in the same recombinant molecule). The nucleic acid molecules contained in such recombinant chimeric molecules are operatively linked to one or more transcription control sequences, in which each nucleic acid molecule contained in a chimeric recombinant molecule can be expressed using the same or different transcription control sequences.

One or more recombinant molecules of the present invention can be used to produce an encoded product (i.e., an immunogen protein or a cytokine protein) useful in the method of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any mammalian cell that can be transfected. Host cells can be either untransfected cells or cells that are already transformed with at least one nucleic acid molecule. Host cells according to the present invention can be any cell capable of producing an immunogen (e.g., tumor, allergen or pathogen) and/or a cytokine according to the present invention. A preferred host cell includes a mammalian lung cells, lymphocytes, muscle cells, hematopoietic precursor cells, mast cells, natural killer cells, macrophages, monocytes, epithelial cells, endothelial cells, dendritic cells, mesenchymal cells, Langerhans cells, cells found in granulomas and tumor cells of any cellular origin. An even more preferred host cell of the present invention includes mammalian mesenchymal cells, epithelial cells, endothelial cells, macrophages, monocytes, lung cells, muscle cells, T cells and dendritic cells.

According to the method of the present invention, a host cell is preferably transfected in vivo (i.e., in a mammal) as a result of intravenous or intraperitoneal administration to a mammal of a nucleic acid molecule complexed to a liposome delivery vehicle. Transfection of a nucleic acid molecule into a host cell according to the present invention can be accomplished by any method by which a nucleic acid molecule administered with a liposome delivery vehicle can be inserted into the cell in vivo, and includes lipofection.

It may be appreciated by one skilled in the art that use of recombinant DNA technologies can improve expression of transfected nucleic acid molecules by manipulating, for example, the duration of expression of the transgene (i.e., recombinant nucleic acid molecule), the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, increasing the duration of expression of the recombinant molecule, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein. Additionally, a nucleic acid molecule, and particularly a plasmid portion, including transcription control sequences, can be modified to make the nucleic acids more immunostimulatory, such as by the addition of CpG moieties to the nucleic acids.

One embodiment of the method of the present invention, when the mammal has cancer, a therapeutic composition to be intravenously administered to the mammal comprises a plurality of recombinant nucleic acid molecules, wherein each of the recombinant nucleic acid molecules comprises a cDNA sequence, each of the cDNA sequences encoding a tumor antigen or a fragment thereof (i.e., at least a portion of a tumor antigen as defined above, preferably a portion containing a T or B cell epitope). The cDNA sequences are amplified from total RNA that has been isolated from an autologous tumor sample. Each of the plurality of cDNA sequences is operatively linked to a transcription control sequence. Administration of such a therapeutic composition to a mammal that has cancer results in the expression of the cDNA sequences encoding the tumor antigens in the tissue of the mammal (pulmonary tissue by intravenous administration and spleen and liver by intraperitoneal administration). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the above-mentioned tissues of the mammal. According to this embodiment of the present invention, an autologous tumor sample is derived from the mammal to whom the therapeutic composition is to be administered. Therefore, the cDNA sequences in the therapeutic composition will encode tumor antigens present in the cancer against which an immune response is to be elicited. In this embodiment, it is not necessary to know which of the antigens in a given tumor sample is the most immunogenic (i.e., the best immunogens), since substantially all of the antigens expressed by the tumor sample are administered to the mammal. In addition, eliciting an immune response against multiple tumor antigens/immunogens is likely to have the benefit of enhancing the therapeutic efficacy of the immune response against the cancer.

In this embodiment of the method of the present invention, a plurality of recombinant nucleic acid molecules as described can also be referred to as a library of nucleic acid molecules, and more particularly, a cDNA library. Methods to produce cDNA libraries are well known in the art. Such methods are disclosed, for example, in Sambrook et al., supra. More particularly, in this embodiment, a therapeutic composition includes a plurality of recombinant cDNA molecules encoding tumor antigens, or fractions thereof, which represents the genes that are expressed by an autologous tumor sample. Such a plurality of recombinant nucleic acid molecules can be produced, for example by isolating total RNA from an autologous tumor sample, converting (i.e., amplifying) the RNA into a plurality of cDNA molecules, and then preparing a cDNA library by cloning the cDNA molecules into recombinant vectors to form a plurality of recombinant molecules. As used herein, total RNA refers to all of the RNA isolatable from a cellular sample using standard methods known in the art, and typically includes mRNA, hnRNA, tRNA and rRNA. Methods for isolating total RNA from a cellular sample, such as a tumor sample, are known in the art (See for example, Sambrook et al., supra). In a further embodiment, prior to amplification of cDNA from the total RNA, the RNA can be selected to isolate poly-A RNA (i.e., RNA comprising a poly-A tail at the 3' terminus, reflective of mRNA, the primary RNA transcript which encodes a protein expressed by a cell). In yet another embodiment, such a cDNA library can be "subtracted" against a cDNA library from a normal cellular sample in the mammal in order to remove nucleic acid molecules encoding antigens present in non-tumor cells (i.e., normal cells) of the mammal, thereby enriching the tumor-specific immune response and preventing deleterious immune responses. Methods for subtraction of a nucleic acid library are also known in the art (See Sambrook et al., supra).

In yet another embodiment of the present invention of the method to elicit an immune response in a mammal that has cancer, a therapeutic composition to be intravenously or intraperitoneally administered to a mammal comprises a plurality of recombinant nucleic acid molecules, wherein each of the recombinant nucleic acid molecules comprises a cDNA sequence, each of the cDNA sequences encoding a tumor antigen or a fragment thereof (i.e., at least a portion of a tumor antigen as defined above). In this embodiment, the cDNA sequences are amplified from total RNA that has been isolated from a plurality of allogeneic tumor samples of the same histological tumor type. Each of the plurality of cDNA sequences is operatively linked to a transcription control sequence. Administration of such a therapeutic composition to a mammal that has cancer results in the expression of the cDNA sequences encoding the tumor antigens in the tissue of the mammal (according to the route of administration, as previously discussed). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the tissues of the mammal.

In this embodiment of the present invention, a plurality of recombinant nucleic acid molecules comprising cDNA sequences encoding tumor antigens (i.e., a cDNA library) is prepared from the total RNA isolated from a plurality of allogeneic tumor samples of the same histological tumor type. According to the present invention, a plurality of allogeneic tumor samples are tumor samples of the same histological tumor type, isolated from two or more mammals of the same species who differ genetically at least within the major histocompatibility complex (MHC), and typically at other genetic loci. Therefore, the plurality of recombinant molecules encoding tumor antigens is representative of the substantially all of the tumor antigens present in any of the individuals from which the RNA was isolated. This embodiment of the method of the present invention provides a genetic vaccine which compensates for natural variations between individual patients in the expression of tumor antigens from tumors of the same histological tumor type. Therefore, administration of this therapeutic composition is effective to elicit an immune response against a variety of tumor antigens such that the same therapeutic composition can be administered to a variety of different individuals. Such a therapeutic composition delivered by the present method is particularly useful as a treatment, but may also be useful as a preventative (i.e., prophylactic) therapy. Methods to prepare such a cDNA library from a plurality of allogeneic tumor samples are the same as those described above for autologous tumor samples.

In yet another embodiment of the present invention of the method to elicit an immune response in a mammal, a therapeutic composition to be intravenously or intraperitoneally administered to a mammal comprises a plurality of recombinant nucleic acid molecules, wherein each of the recombinant nucleic acid molecules comprises a cDNA sequence, each of the cDNA sequences encoding an immunogen from an infectious disease pathogen or a fragment thereof (i.e., at least a portion of a pathogen antigen as defined above). In this embodiment, the cDNA sequences are amplified from total RNA that has been isolated from an infectious disease pathogen. Each of the plurality of cDNA sequences is operatively linked to a transcription control sequence. Administration of such a therapeutic composition to a mammal that has or might contract an infectious disease results in the expression of the cDNA sequences encoding the pathogen antigens in the tissue of the mammal (according to the route of administration, as previously discussed). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the tissues of the mammal.

In this embodiment of the present invention, the plurality of recombinant molecules encoding pathogen antigens is representative of the substantially all of the antigens present in the infectious disease pathogen from which the RNA was isolated. In this embodiment, it is not necessary to know which of the antigens in a given pathogen is the most immunogenic (i.e., the best immunogens), since substantially all of the antigens expressed by the pathogen are administered to the mammal. In addition, eliciting an immune response against multiple pathogen antigens/immunogens is likely to have the benefit of enhancing the therapeutic efficacy of the immune response against the infectious disease. Methods to prepare such a cDNA library from an infectious disease pathogen are the same as those described above for tumor samples.

In yet another embodiment of the present invention of the method to elicit an immune response in a mammal, a therapeutic composition to be intravenously or intraperitoneally administered to a mammal comprises a plurality of recombinant nucleic acid molecules, each of the recombinant nucleic acid molecules comprising a cDNA sequence amplified from total RNA isolated from at least one allergen. In this embodiment, the cDNA sequences are amplified from total RNA, or a fragment thereof, that has been isolated from at least one, and preferably, multiple, allergens. Each of the plurality of cDNA sequences is operatively linked to a transcription control sequence. Administration of such a therapeutic composition to a mammal that has or might contract a disease associated with allergic inflammation results in the expression of the cDNA sequences encoding the allergens in the tissue of the mammal (according to the route of administration, as previously discussed). In a further embodiment, such a therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in the expression of the nucleic acid sequence encoding the cytokine in the tissues of the mammal. In this embodiment of the present invention, the plurality of recombinant molecules encoding allergens is representative of the substantially all of the epitopes present in the allergen from which the RNA was isolated. Additionally, more than one allergen can be administered simultaneously.

Another embodiment of the present invention relates to a method to elicit a tumor antigen-specific immune response and a systemic, non-specific immune response in a mammal that has cancer, which includes the step of intravenously or intraperitoneally administering to the mammal a therapeutic composition which includes: (a) a liposome delivery vehicle; and (b) total RNA isolated from a tumor sample, wherein the RNA encodes tumor antigens or fragments thereof. Administration of such a therapeutic composition to the mammal results in the expression of the RNA encoding tumor antigens or fragments thereof in the tissue of the mammal. In a preferred embodiment, the RNA is enriched for poly-A RNA prior to administration of the therapeutic composition to the mammal, as described above. In a further embodiment, the therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in expression of the nucleic acid sequence encoding the cytokine in the tissue of the mammal.

In this embodiment of the present invention, total RNA or more preferably, poly-A enriched RNA, is isolated from a tumor sample as previously described (See Sambrook et al., supra), complexed with a liposome delivery vehicle and administered intravenously or intraperitoneally to a mammal that has cancer. The RNA encoding substantially all of the tumor antigens of the tumor sample is then expressed in the tissues of the mammal. Although RNA is normally degraded rapidly in serum by RNAses, the present inventors believe that RNA complexed to cationic lipids are protected from such RNAses until it reaches the tissues, where gene expression occurs. The advantage of administering RNA directly to a mammal according to this particular embodiment of the method of the present invention is that an immune response can be elicited against multiple tumor antigens directly in vivo, without requiring any substantial in vitro manipulations of the tumor tissues or host immune cells. Specific examples of this embodiment of the present invention are described in Examples 7a and 7b.

Another embodiment of the present invention relates to a method to elicit a pathogen antigen-specific immune response and a systemic, non-specific immune response in a mammal that has an infectious disease, which includes the step of intravenously or intraperitoneally administering to the mammal a therapeutic composition which includes: (a) a liposome delivery vehicle; and (b) total RNA isolated from an infectious disease pathogen, wherein the RNA encodes pathogen antigens or fragments thereof. Administration of such a therapeutic composition to the mammal results in the expression of the RNA encoding pathogen antigens or fragments thereof in the tissue of the mammal. In a preferred embodiment, the RNA is enriched for poly-A RNA prior to administration of the therapeutic composition to the mammal, as described above. In a further embodiment, the therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in expression of the nucleic acid sequence encoding the cytokine in the tissue of the mammal.

Another embodiment of the present invention relates to a method to elicit an allergen-specific immune response and a systemic, non-specific immune-response in a mammal that has a disease associated with allergic inflammation, which includes the step of intravenously or intraperitoneally administering to the mammal a therapeutic composition which includes: (a) a liposome delivery vehicle; and (b) total RNA isolated from an allergen, wherein the RNA encodes at least one allergen protein or a fragment thereof. Administration of such a therapeutic composition to the mammal results in the expression of the RNA encoding at least one allergen or a fragment thereof in the tissue of the mammal. In a preferred embodiment, the RNA is enriched for poly-A RNA prior to administration of the therapeutic composition to the mammal, as described above. In a further embodiment, the therapeutic composition comprises a recombinant nucleic acid molecule having a nucleic acid sequence encoding a cytokine, wherein the nucleic acid sequence is operatively linked to a transcription control sequence. Administration of such a therapeutic composition to a mammal results in expression of the nucleic acid sequence encoding the cytokine in the tissue of the mammal.

A therapeutic composition of the present invention includes a liposome delivery vehicle. According to the present invention, a liposome delivery vehicle comprises a lipid composition that is capable of preferentially delivering a therapeutic composition of the present invention to the pulmonary tissues in a mammal when administration is intravenous, and to the spleen and liver tissues of a mammal when administration is intraperitoneal. The phrase "preferentially delivering" means that although the liposome can deliver a nucleic acid molecule to sites other than the pulmonary or spleen and liver tissue of the mammal, these tissues are the primary site of delivery.

A liposome delivery vehicle of the present invention can be modified to target a particular site in a mammal, thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms, such as targeting by addition of exogenous targeting molecules to a liposome (i.e., antibodies) are not a necessary component of the liposome delivery vehicle of the present invention, since effective immune activation at immunologically active organs is already provided by the composition and route of delivery of the present compositions without the aid of additional targeting mechanisms. Additionally, for efficacy, the present invention does not require that a protein encoded by a given nucleic acid molecule be expressed within the target cell (e.g., tumor cell, pathogen, etc.). The compositions and method of the present invention are efficacious when the proteins are expressed in the vicinity of (i.e., adjacent to) the target site, including when the proteins are expressed by non-target cells.

A liposome delivery vehicle is preferably capable of remaining stable in a mammal for a sufficient amount of time to deliver a nucleic acid molecule of the present invention to a preferred site in the mammal. A liposome delivery vehicle of the present invention is preferably stable in the mammal into which it has been administered for at least about 30 minutes, more preferably for at least about 1 hour and even more preferably for at least about 24 hours.

A liposome delivery vehicle of the present invention comprises a lipid composition that is capable of fusing with the plasma membrane of the targeted cell to deliver a nucleic acid molecule into a cell. Preferably, when a nucleic acid:liposome complex of the present invention is administered intravenously, the transfection efficiency of a nucleic acid:liposome complex of the present invention is at least about 1 picogram (pg) of protein expressed per milligram (mg) of total tissue protein per microgram (pg) of nucleic acid delivered. More preferably, the transfection efficiency of a nucleic acid:liposome complex of the present invention is at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered. When the route of delivery of a nucleic acid:lipid complex of the present invention is intraperitoneal, the transfection efficiency of the complex can be as low as 1 fg of protein expressed per mg of total tissue protein per µg of nucleic acid delivered, with the above amounts being more preferred.

A preferred liposome delivery vehicle of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes commonly used in, for example, gene delivery methods known to those of skill in the art. Preferred liposome delivery vehicles comprise multilamellar vesicle (MLV) lipids and extruded lipids. Methods for preparation of MLV's are well known in the art and are described, for example, in the Examples section. According to the present invention, "extruded lipids" are lipids which are prepared similarly to MLV lipids, but which are subsequently extruded through filters of decreasing size, as described in Templeton et al., 1997, *Nature Biotech.*, 15:647–652, which is incorporated herein by reference in its entirety. Although small unilamellar vesicle (SUV) lipids can be used in the composition and method of the present invention, the present inventors have found that multilamellar vesicle lipids are significantly more immunostimulatory than SUVs when complexed with nucleic acids in vivo (See Example 2d). More preferred liposome delivery vehicles comprise liposomes having a polycationic lipid composition (i.e., cationic liposomes) and/or liposomes having a cholesterol backbone conjugated to polyethylene glycol. Preferred cationic liposome compositions include, but are not limited to DOTMA and cholesterol, DOTAP and cholesterol, DOTIM and cholesterol, and DDAB and cholesterol. A most preferred liposome composition for use as a delivery vehicle in the method of the present invention includes DOTAP and cholesterol.

Complexing a liposome with a nucleic acid molecule of the present invention can be achieved using methods standard in the art (see, for example, methods Section A described in the Examples). According to the present invention a cationic lipid:DNA complex is also referred to herein as a CLDC, and a cationic lipid:RNA complex is also referred to herein as CLRC. A suitable concentration of a nucleic acid molecule of the present invention to add to a liposome includes a concentration effective for delivering a sufficient amount of nucleic acid molecule into a mammal such that a systemic immune response is elicited. When the nucleic acid molecule encodes an immunogen or a cytokine, a suitable concentration of nucleic acid molecule to add to a liposome includes a concentration effective for delivering a sufficient amount of nucleic acid molecule into a cell such that the cell can produce sufficient immunogen and/or cytokine protein to regulate effector cell immunity in a desired manner. Preferably, from about 0.1 µg to about 10 µg of nucleic acid molecule of the present invention is combined with about 8 nmol liposomes, more preferably from about 0.5 µg to about 5 µg of nucleic acid molecule is combined with about 8 nmol liposomes, and even more preferably about 1.0 µg of nucleic acid molecule is combined with about 8 nmol liposomes. In one embodiment, the ratio of nucleic acids to lipids (µg nucleic acid:nmol lipids) in a composition of the present invention is preferably at least about 1:1 nucleic acid:lipid by weight (i.e., 1 µg nucleic acid:1 nmol lipid), and more preferably, at least about 1:5, and more preferably at least about 1:10, and even more preferably at least about 1:20. Ratios expressed herein are based on the amount of cationic lipid in the composition, and not on the total amount of lipid in the composition. In another embodiment, the ratio of nucleic acids to lipids in a composition of the present invention is preferably from about 1:1 to about 1:64 nucleic acid:lipid by weight; and more preferably, from about 1:5 to about 1:50 nucleic acid:lipid by weight; and even more preferably, from about 1:10 to about 1:40 nucleic acid:lipid by weight; and even more preferably, from about 1:15 to about 1:30 nucleic acid:lipid by weight. Another particularly preferred ratio of nucleic acid:lipid is from about 1:8 to 1:16, with 1:8 to 1:32 being more preferred. Typically, while non-systemic routes of nucleic acid administration (i.e., intramuscular, intratracheal, intradermal) would use a ratio of about 1:1 to about 1:3, systemic routes of administration according to the present invention can use much less nucleic acid as compared to lipid and achieve equivalent or better results than non-systemic routes. Moreover, compositions designed for gene therapy/gene replacement, even when administered by intravenous administration, typically use more nucleic acid (e.g., from 6:1 to 1:10, with 1:10 being the least amount of DNA used) as compared to the systemic immune activation composition and method of the present invention.

In another embodiment of the present invention, a therapeutic composition further comprises a pharmaceutically acceptable excipient. As used herein, a pharmaceutically acceptable excipient refers to any substance suitable for delivering a therapeutic composition useful in the method of the present invention to a suitable in vivo site. Preferred pharmaceutically acceptable excipients are capable of maintaining a nucleic acid molecule of the present invention in a form that, upon arrival of the nucleic acid molecule to a cell, the nucleic acid molecule is capable of entering the cell and being expressed by the cell if the nucleic acid molecule encodes a protein to be expressed. Suitable excipients of the present invention include excipients or formularies that transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with a preferred non-ionic buffer being 5% dextrose in water (DW5).

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Therapeutic compositions of the present invention can be sterilized by conventional methods and/or lyophilized.

According to the present invention, an effective administration protocol (i.e., administering a therapeutic composition in an effective manner) comprises suitable dose parameters and modes of administration that result in elicitation of an immune response in a mammal that has a disease, preferably so that the mammal is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of eliciting an immune response in a mammal with a disease when administered one or more times over a suitable time period. Doses can vary depending upon the disease being treated. In the treatment of cancer, a suitable single dose can be dependent upon whether the cancer being treated is a primary tumor or a metastatic form of cancer. Doses of a therapeutic composition of the present invention suitable for use with intravenous or intraperitoneal administration techniques can be used by one of skill in the art to determine appropriate single dose sizes for systemic administration based on the size of a mammal.

In a preferred embodiment, an appropriate single dose of a nucleic acid:liposome complex of the present invention is from about 0.1 $\mu$g to about 100 $\mu$g per kg body weight of the mammal to which the complex is being administered. In another embodiment, an appropriate single dose is from about 1 $\mu$g to about 10 $\mu$g per kg body weight. In another embodiment, an appropriate single dose of nucleic acid:lipid complex is at least about 0.1 $\mu$g of nucleic acid to the mammal, more preferably at least about 1 $\mu$g of nucleic acid, even more preferably at least about 10 $\mu$g of nucleic acid, even more preferably at least about 50 $\mu$g of nucleic acid, and even more preferably at least about 100 $\mu$g of nucleic acid to the mammal.

Preferably, when nucleic acid:liposome complex of the present invention contains a nucleic acid molecule which is to be expressed in the mammal, an appropriate single dose of a nucleic acid:liposome complex of the present invention results in at least about 1 pg of protein expressed per mg of total tissue protein per $\mu$g of nucleic acid delivered. More preferably, an appropriate single dose of a nucleic acid:liposome complex of the present invention is a dose which results in at least about 10 pg of protein expressed per mg of total tissue protein per $\mu$g of nucleic acid delivered; and even more preferably, at least about 50 pg of protein expressed per mg of total tissue protein per $\mu$g of nucleic acid delivered; and most preferably, at least about 100 pg of protein expressed per mg of total tissue protein per $\mu$g of nucleic acid delivered. When the route of delivery of a nucleic acid:lipid complex of the present invention is intraperitoneal, an appropriate single dose of a nucleic acid:liposome complex of the present invention is a dose which results in as low as 1 fg of protein expressed per mg of total tissue protein per $\mu$g of nucleic acid delivered, with the above amounts being more preferred.

A suitable single dose of a therapeutic composition of the present invention to elicit a systemic, non-antigen-specific immune response in a mammal is a sufficient amount of a nucleic acid molecule complexed to a liposome delivery vehicle, when administered intravenously or intraperitoneally, to elicit a cellular and/or humoral immune response in vivo in a mammal, as compared to a mammal which has not been administered with the therapeutic composition of the present invention (i.e., a control mammal). Preferred dosages of nucleic acid molecules to be included in a nucleic acid:lipid complex of the present invention have been discussed, above.

A suitable single dose of a therapeutic composition to elicit an immune response against a tumor is a sufficient amount of a tumor antigen-encoding recombinant molecule, alone or in combination with a cytokine-encoding recombinant molecule, to reduce, and preferably eliminate, the tumor following lipofection of the recombinant molecules into cells of the tissue of the mammal that has cancer.

According to the present invention, a single dose of a therapeutic composition useful to elicit an immune response against an infectious disease and/or against a lesion associated with such a disease, comprising a pathogen-encoding recombinant molecule combined with liposomes, alone or in combination with a cytokine-encoding recombinant molecule with liposomes, is substantially similar to those doses used to treat a tumor (as described in detail above). Similarly, a single dose of a therapeutic composition useful to elicit an immune response against an allergen, comprising an allergen-encoding recombinant molecule combined with liposomes, alone or in combination with a cytokine-encoding recombinant molecule with liposomes, is substantially similar to those doses used to treat a tumor.

It will be obvious to one of skill in the art that the number of doses administered to a mammal is dependent upon the extent of the disease and the response of an individual patient to the treatment. For example, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to treat a given disease.

It is to be noted that the method of the present invention further differs from previously described gene therapy/gene replacement protocols, because the time between administration and boosting of the nucleic acid:lipid complex is significantly longer than the typical administration protocol for gene therapy/gene replacement. For example, elicitation of an immune response using the compositions and methods of the present invention typically includes an initial administration of the therapeutic composition, followed by booster immunizations at 3–4 weeks after the initial administration, optionally followed by subsequent booster immunizations every 3–4 weeks after the first booster, as needed to treat a disease according to the present invention. In contrast, gene therapy/gene replacement protocols typically require more frequent administration of a nucleic acid in order to obtain sufficient gene expression to generate or replace the desired gene function (e.g., weekly administrations).

A preferred number of doses of a therapeutic composition comprising a tumor antigen-encoding recombinant molecule, alone or in combination with a cytokine-encoding recombinant molecule, complexed with a liposome delivery vehicle in order to elicit an immune response against a metastatic cancer, is from about 2 to about 10 administrations patient, more preferably from about 3 to about 8 administrations per patient, and even more preferably from about 3 to about 7 administrations per patient. Preferably, such administrations are given once every 3–4 weeks, as described above, until signs of remission appear, and then once a month until the disease is gone.

According to the present invention, the number of doses of a therapeutic composition to elicit an immune response against an infectious disease and/or a lesion associated with such disease, comprising a pathogen antigen-encoding recombinant molecule, alone or in combination with a cytokine-encoding recombinant molecule, complexed with a liposome delivery vehicle, is substantially similar to those number of doses used to treat a tumor (as described in detail above).

A therapeutic composition is administered to a mammal in a fashion to elicit a systemic, non-antigen-specific immune response in a mammal, and when the nucleic acid molecule in the composition encodes an immunogen, to enable expression of the administered recombinant molecule of the present invention into an immunogenic protein (in the case of the tumor, pathogen antigen or allergen) or immunoregulatory protein (in the case of the cytokine) in the mammal to be treated for disease. According to the method of the present invention, a therapeutic composition is administered by intravenous or intraperitoneal injection, and preferably, intravenously. Intravenous injections can be performed using methods standard in the art. According to the method of the present invention, administration of the nucleic acid:lipid complexes can be at any site in the mammal wherein systemic administration (i.e., intravenous or intraperitoneal administration) is possible, particularly when the liposome delivery vehicle comprises cationic liposomes. Administration at any site in a mammal will elicit a potent immune response when either intravenous or intraperitoneal administration is used, and particularly, when intravenous administration is used. Suitable sites for administration include sites in which the target site for immune activation is not restricted to the first organ having a capillary bed proximal to the site of administration (i.e., compositions can be administered at an administration site that is distal to the target immunization site). In other words, for example, intravenous administration of a composition of the present invention which is used to treat a kidney tumor in a mammal can be administered intravenously at any site in the mammal and will still elicit a strong anti-tumor immune response and be efficacious at reducing or eliminating the tumor, even though the kidney is not the first organ having a capillary bed proximal to the site of administration. When a specific anti-tumor effect is desired (i.e., reduction or elimination of a tumor) and the route of administration is intravenous, the site of administration again can be at any site by which a composition can be administered intravenously, regardless of the location of the tumor relative to the site of administration. For intraperitoneal administration with regard to anti-tumor efficacy (but not immune activation/immunization), it is preferable to use this mode of administration when the tumor is in the peritoneal cavity, or when the tumor is a small tumor. For immunization and immune activation, as discussed above, intraperitoneal administration is a suitable mode of administration, particularly in comparison to non-systemic routes, as demonstrated in the Examples section.

In the method of the present invention, therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, sheep, cattle, horses and pigs, with humans and dogs being particularly preferred, and humans being most preferred. While a therapeutic composition of the present invention is effective to elicit an immune response against a disease in inbred species of mammals, the composition is particularly useful for eliciting an immune response in outbred species of mammals.

As discussed above, a therapeutic composition of the present invention administered by the present method is useful for eliciting an immune response in a mammal having a variety of diseases, and particularly cancer, allergic inflammation and infectious diseases. A therapeutic composition of the present invention, when delivered intravenously or intraperitoneally, is advantageous for eliciting an immune response in a mammal that has cancer in that the composition overcomes the mechanisms by which cancer cells avoid immune elimination (i.e., by which cancer cells avoid the immune response effected by the mammal in response to the disease). Cancer cells can avoid immune elimination by, for example, being only slightly immunogenic, modulating cell surface antigens and inducing immune suppression. A suitable therapeutic composition for use in eliciting an immune response in a mammal that has cancer comprises a nucleic acid:lipid complex of the present invention, wherein the nucleic acid either is not operatively linked to a transcription control sequence, or more preferably, encodes a tumor antigen-encoding recombinant molecule operatively linked to a transcription control sequence, alone or in combination with a cytokine-encoding recombinant molecule (separately or together). A therapeutic composition of the present invention, elicits a systemic, non-specific immune response in the mammal and, upon entering targeted pulmonary or spleen and liver cells, leads to the production of tumor antigen (and, in particular embodiments, cytokine protein) that activate cytotoxic T cells, natural killer cells, T helper cells and macrophages. Such cellular activation overcomes the otherwise relative lack of immune response to cancer cells, leading to the destruction of such cells.

A therapeutic composition of the present invention which includes a nucleic acid molecule encoding a tumor antigen is useful for eliciting an immune response in a mammal that has cancer, including both tumors and metastatic forms of cancer. Treatment with the therapeutic composition overcomes the disadvantages of traditional treatments for metastatic cancers. For example, compositions of the present invention can target dispersed metastatic cancer cells that cannot be treated using surgical methods. In addition, administration of such compositions do not result in the harmful side effects caused by chemotherapy and radiation therapy, and can be administered repeatedly. Moreover, the compositions administered by the method of the present invention typically target the vesicles of tumors, so that expression of a tumor antigen or cytokine within the tumor cell itself is not necessary to provide efficacy against the tumor. Indeed, a general advantage of the present invention is that delivery of the composition itself elicits a powerful immune response and expression of the nucleic acid molecule at least in the vicinity of the target site (at or adjacent to the site) provides effective immune activation and efficacy against the target.

A therapeutic composition of the present invention which includes a nucleic acid molecule encoding a tumor antigen is preferably used to elicit an immune response in a mammal that has a cancer which includes, but is not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. Particularly preferred cancers to treat with a therapeutic composition of the present invention include primary lung cancers and pulmonary metastatic cancers. A therapeutic composition of the present invention is useful for eliciting an immune response in a mammal to treat tumors that can form in such cancers, including malignant and benign tumors. Preferably, expression of the tumor antigen in a pulmonary tissue of a mammal that has cancer (i.e., by intravenous delivery) produces a result selected from the group of alleviation of the cancer, reduction of a tumor associated with the cancer, elimination of a tumor associated with the cancer, prevention of metastatic cancer, prevention of the cancer and stimulation of effector cell immunity against the cancer.

A therapeutic composition of the present invention which includes a nucleic acid molecule encoding an immunogen from an infectious disease pathogen is advantageous for eliciting an immune response in a mammal that has infectious diseases responsive to an immune response. An infectious disease responsive to an immune response is a disease caused by a pathogen in which the elicitation of an immune response against the pathogen can result in a prophylactic or therapeutic effect as previously described herein. Such a method provides a long term, targeted therapy for primary lesions (e.g., granulomas) resulting from the propagation of a pathogen. As used herein, the term "lesion" refers to a lesion formed by infection of a mammal with a pathogen. A therapeutic composition for use in the elicitation of an immune response in a mammal that has an infectious disease comprises a pathogen antigen-encoding recombinant molecule, alone or in combination with a cytokine-encoding recombinant molecule of the present invention, combined with a liposome delivery vehicle. Similar to the mechanism described above for the treatment of cancer, eliciting an immune response in a mammal that has an infectious disease with immunogens from the infectious disease pathogens with or without cytokines can result in increased T cell, natural killer cell, and macrophage cell activity that overcome the relative lack of immune response to a lesion formed by a pathogen. Preferably, expression of the immunogen in a tissue of a mammal that has an infectious disease produces a result which includes alleviation of the disease, regression of established lesions associated with the disease, alleviation of symptoms of the disease, immunization against the disease and stimulation of effector cell immunity against the disease.

A therapeutic composition of the present invention is particularly useful for eliciting an immune response in a mammal that has an infectious diseases caused by pathogens including, but not limited to, bacteria (including intracellular bacteria which reside in host cells), viruses, parasites (including internal parasites), fungi (including pathogenic fungi) and endoparasites. Preferred infectious diseases to treat with a therapeutic composition of the present invention include chronic infectious diseases, and more preferably, pulmonary infectious diseases, such as tuberculosis. Particularly preferred infectious diseases to treat with a therapeutic composition of the present invention include human immunodeficiency virus (HIV), *Mycobacterium tuberculosis*, herpesvirus, papillomavirus and Candida.

In one embodiment, an infectious disease a therapeutic composition of the present invention is a viral disease, and preferably, is a viral disease caused by a virus which includes, human immunodeficiency virus, and feline immunodeficiency virus.

A therapeutic composition of the present invention which includes a nucleic acid molecule encoding an immunogen that is an allergen is advantageous for eliciting an immune response in a mammal that has a disease associated with allergic inflammation. A disease associated with allergic inflammation is a disease in which the elicitation of one type of immune response (e.g., a Th2-type immune response) against a sensitizing agent, such as an allergen, can result in the release of inflammatory mediators that recruit cells involved in inflammation in a mammal, the presence of which can lead to tissue damage and sometimes death. The method of the present invention, as described in detail in the Examples section, elicits a Th1-type response, which, without being bound by theory, the present inventors believe can have prophylactic or therapeutic effects such that allergic inflammation is alleviated or reduced. A therapeutic composition for use in the elicitation of an immune response in a mammal that has a disease associated with allergic inflammation comprises an allergen-encoding recombinant molecule, alone or in combination with a cytokine-encoding recombinant molecule, combined with a liposome delivery vehicle. Similar to the mechanism described above for the treatment of cancer, eliciting an immune response in a mammal that has a disease, associated with allergic inflammation with allergens with or without cytokines can result in increased Th1-type T cell, natural killer cell, and macrophage cell activity that overcome the harmful effects of a Th2-type immune response against the same allergen. Preferably, expression of the allergen in a tissue of a mammal that has a disease associated with allergic inflammation produces a result which includes alleviation of the disease, alleviation of symptoms of the disease, desensitization against the disease and stimulation a protective immune response against the disease.

Preferred diseases associated with allergic inflammation which are preferable to treat using the method and composition of the present invention include, allergic airway diseases, allergic rhinitis, allergic conjunctivitis and food allergy.

The following examples are provided for the purposes of illustration and are not intended to limit the scope of the present invention.

EXAMPLES

For the following Examples 1–7, the following experimental methods and materials were used.

A. Preparation of Cationic Lipid DNA Complexes (CLDC)

The cationic liposomes used in the following experiments (unless otherwise indicated) consisted of DOTAP (1,2 dioleoyl-3-trimethylammonium-propane) and cholesterol mixed in a 1:1 molar ratio, dried down in round bottom tubes, then rehydrated in 5% dextrose solution (D5W) by heating at 50° C. for 6 hours, as described previously (Solodin et al., 1995, *Biochemistry* 34:13537–13544, incorporated herein by reference in its entirety). Other lipids (e.g., DOTMA) were prepared similarly for some experiments as indicated. This procedure results in the formation of liposomes that consists of multilamellar vesicles (MLV), which the present inventors have found give optimal transfection efficiency as compared to small unilamellar vesicles (SUV). The production of MLVs and related "extruded lipids" is also described in Liu et al., 1997, *Nature Biotech.* 15:167–173; and Templeton et al., 1997, *Nature Biotech.* 15:647–652; both of which are incorporated herein by reference in their entirety. Plasmid DNA (pCR3.1, Invitrogen) was purified from *E. coli* as described previously, using modified alkaline lysis and polyethylene glycol precipitation (Liu et al., 1997, supra). DNA for injection was resuspended in distilled water. Eukaryotic DNA (salmon testis and calf thymus) was purchased from Sigma Chemical Company. For many of the experiments reported here, the plasmid DNA did not contain a gene insert (unless otherwise noted), and is thus referred to as "non-coding" or "empty vector" DNA.

The cationic lipid DNA complexes (CLDC) used in the experiments below were prepared by gently adding DNA to a solution of lipid in 5% dextrose solution (D5W) at room temperature, then gently pipetting up and down several times to assure proper mixing. The DNA:lipid ratio was 1:8 (1.0 µg DNA to 8 nmol lipid). The CLDC were used within 30–60 minutes of preparation. To prepare small unilamellar vesicles (SUV) used in some experiments (as indicated), the CLDC that were formed using MLV liposomes as described above were subjected to sonication for 5 minutes, as described previously (Liu et al., 1997, supra).

B. Gene Constructs

For antigen-specific immunization experiments, plasmid-based, eukaryotic expression vectors were utilized to express genes in vivo. Expression vectors.,(using pCR3.1, Invitrogen) for the cytokine cDNAs (IL-2, IFNγ, IL-12) were all constructed using PCR amplification of RNA prepared from normal mouse spleens as described, for example in Sambrook et al., supra. The β-gal expression construct was provided by Dr. Cori Gorman. For immunization with these gene constructs, CLDC containing the desired gene constructs were injected by tail vein (i.e., intravenous delivery) or intraperitoneally (as indicated) to deliver a total DNA amount of 5.0 to 10.0 ug DNA.

For RNA immunization experiments, tumor cells (either B 16 cells or CT-26 cells; see below) were grown in vitro, followed by extraction of the poly-A enriched RNA using standard procedures (Sambrook, supra). The RNA was resuspended in water and frozen prior to formation of complexes with liposomes. The same lipid:RNA ratios as described above for lipid:DNA complexes were used to prepare cationic lipid RNA complexes (CLRC).

When more than one gene was injected simultaneously into the same animal, the plasmid DNAs were first mixed and then added to liposomes to form CLDC.

C. In Vivo Evaluation of Immune Activation

Mice (3 per group, unless otherwise indicated) were injected intravenously or intraperitoneally, as indicated in the individual experiments, once with 100 ul of CLDC (prepared as described above) in D5W. Control mice were injected with 100 µl of D5W only. Three different strains of mice were evaluated in these experiments (C57Bl/6, BALB/c, ICR), but most of the data was generated using C57Bl/6 mice. The total amount of DNA injected was 10 ug per mouse, unless specified otherwise. At various time points post-injection (as indicated), the spleen and lung tissues were collected, mononuclear cell preparations were made, and the cells were assayed for expression of activation markers or cytokine release (see below).

D. In Vitro Evaluation of Immune Activation

Spleen cells obtained from normal (untreated mice) were incubated in modified Eagles cell culture medium with 10% FBS with either lipid alone, DNA alone, or cationic lipid DNA complexes (CLDC) to assess the effects on immune activation. The final DNA concentration in these experiments was 1.0 ug/ml medium. Cell activation was assessed by flow cytometry and cytokine release was quantitated by ELISA (see below).

E. Flow Cytometry

Upregulation of the early activation marker, CD69, which is upregulated on activated T cells, B cells, macrophages and NK cells, was used to assess early immune cell activation. Single cell suspensions were prepared from spleens of mice by $NH_4Cl$ lysis procedure (Sambrook, supra), and lung mononuclear cells were prepared from lung tissues by collagenase digestion. Briefly, lung tissues were digested in 0.02% collagenase at 37° C. for one hour. Lung mononuclear cells were purified from the digested tissue by Ficoll gradient, centrifugation. For each experiment, spleen and lung cells were prepared from 3 animals per treatment group, unless noted otherwise. Cells were analyzed using a Becton-Dickinson FACSCalibur flow cytometer, with analysis gates set by first gating on spleen lymphocytes. Between 10,000 and 30,000 gated events were analyzed for each cell type. For analysis of cell activation, 3-color flow cytometric analysis was done, using anti-CD69 phycoerythrin (Pharmingen, San Diego, Calif.) to quantitate the number of CD69 positive cells. Cells were also dual-labeled to evaluate T cells (anti-αβTCR antibody (biotin H57.597; Pharmingen) plus antibodies to either CD4 (FITC RM4-5; Pharmingen) or CD8 (FITC 53–6.7; Pharmingen). B cells were dual-labeled with anti-B220 (Pharmingen) and anti-$IA^b$ (FITC 3F12.35; provided by Dr. John Freed, National Jewish) or anti-$IA^d$ (FITC 14.44); NK cells were dual-labeled using anti NK 1.1 (biotin PK136; Pharmingen) and anti CD3 (FITC 2C11); macrophages were evaluated using anti-CR3 (biotin Mac-1; Pharmingen) and FITC anti-$IA^b$ or anti-$IA^d$. The percentage of double positive cells expressing CD69 was determined for each cell type, and the mean (±SD) CD69+ cells plotted.

F. Cytotoxicity Assay

A standard 4-hour $^{51}$Cr-release assay was used to quantitate cytotoxic activity present in freshly isolated lung and spleen mononuclear cells, using YAC-1 cells as targets. Briefly, effector cells from lung or spleen were added in decreasing concentrations to duplicate wells of a Linbro plate, to which was then added $5 \times 10^3$ target cells that had been previously labeled for 1 hour with $^{51}$Cr. The plates were, incubated at 37° C. for 4 hours, then supernatants from each well were harvested and the amount of radioactive $^{51}$Cr present was determined by automated gamma counter. The percentage specific lysis was calculated as follows:

$$\frac{\text{(observed }^{51}Cr\text{ release)} - \text{(spontaneous }^{51}Cr\text{ release)}}{\text{(maximum }^{51}Cr\text{ release)} - \text{(spontaneous }^{51}Cr\text{ release)}} \times 100$$

G. NK Cell Depletion in Vivo

Mice were depleted of NK cells in vivo by a single intraperitoneal (i.p.) injection of 50 ul rabbit anti-asialoGM1 antiserum (Wako BioProducts, Richmond, Va.). Control animals were injected with 50 ul non-immune rabbit serum. In other experiments, mice were depleted of NK cells by i.p. injection of a monoclonal antibody to NK cells (PK-136), and control mice were injected with an irrelevant, isotype-matched antibody. It was confirmed that these treatments eliminated detectable NK cells in spleen and lung (as determined by flow cytometry) and also eliminated cytotoxic activity in spleen cells (data not shown).

H. Cytokine Assays

Cytokine release was measured in spleen cell supernatants after either in vivo or in vitro stimulation. For assay of cytokine release after in vivo stimulation, spleen or lung mononuclear cells were prepared from mice either 6 or 24 hours after i.v. injection, then cultured at a concentration of $5 \times 10^6$ cells/ml for an additional 18 hours before supernatants were harvested. For in vitro stimulation of cytokine release, spleen cells were incubated in vitro with DNA, lipid, or DNA plus lipid at a final DNA concentration of 1.0 ug DNA per ml for 18 hours, at which time the supernatants were harvested for cytokine assay. Interferon-gamma (IFNγ) was assayed using a sandwich ELISA as is known in the art.

I. Tumor Challenge Experiments

The B16 (clone F10) cells were obtained from Dr. Isiah Fidler (M D Anderson, Houston, Tex.); MCA-205 cells were provided by Dr Jack Routes (National Jewish); CT-26 cells were provided by Dr. Nicholas Restifo (National Cancer Institute); 4T1 cells were provided by Dr. Susan Rosenberg). All cell lines were maintained at 37° C. in Modified Eagles medium supplemented with essential and non-essential amino acids, penicillin and glutamine, and 5% fetal bovine serum, and were treated periodically with ciprofloxacin (10 ug/ml) to maintain mycoplasma-free conditions. The β-gal transfected CT-26 tumor cell line (known as CL-25) was also provided by Dr. Nicholas Restifo.

To establish experimental pulmonary metastases, mice (4 per treatment group) were injected once via the lateral-tail vein with $2.5 \times 10^5$ tumor cells. Treatment with DNA-lipid complexes was initiated 3 days after tumor injection, and was repeated once on day 10 after tumor injection; control mice were injected i.v. with D5W alone. Mice were sacrificed on day 17 to 20 after tumor injection, and the number of tumor nodules per lung was determined by insufflating lungs with India ink solution and manually counting total nodules per lung under a tumor dissecting microscope (Wexter et al., 1966, *J. Natl. Cancer Inst.* 36:641–645, incorporated herein by reference in its entirety).

Example 1

The following experiments a–l and FIGS. 1–12 show that systemically administered cationic liposome DNA complexes (CLDC) formed with non-coding DNA (empty vector) elicit potent immune responses in vivo.

Figure 2A:
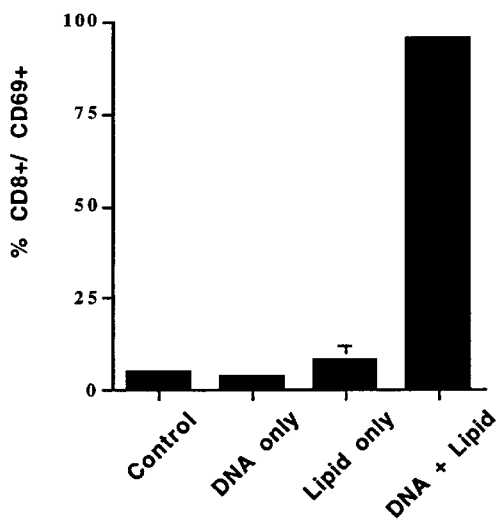
FIG. 2A is a bar graph showing that intravenous injection of CLDC, but not lipid or DNA alone, induces immune activation of CD8+ cells in vivo.
Figure 2B:
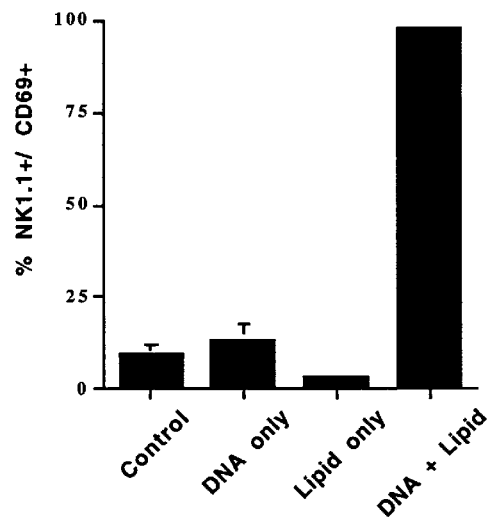
FIG. 2B is a bar graph showing that intravenous injection of CLDC, but not lipid or DNA alone, induces immune activation of NK1.1+ cells in vivo.

(a) The following experiment shows that intravenous (i.v.) injection of CLDC containing empty vector DNA induces marked activation of 5 different immune effector cell populations in vivo. In this experiment, CLDC were prepared which consisted of DOTAP and cholesterol mixed in a 1:1 molar ratio complexed with empty vector plasmid DNA (see Section A above). C57Bl/6 mice were injected intravenously with 100 μl of CLDC (10 ug empty vector DNA per mouse) in DW5 as described (Section C). 24 hours post-injection, spleen cells were harvested from control mice injected with diluent (D5W), and from mice injected with CLDC. Cells were labeled with specific antibodies to evaluate CD4+ and CD8+ T cells, NK cells, B cells, and macrophages and with an antibody to CD69 (early activation marker) and analyzed by flow cytometry (Section E). FIG. 1 shows the results from CD69/immune effector cell staining with control mice (open bars) and 3 CLDC-injected mice (black bars). Injection of CLDC (empty vector) induced pronounced upregulation of CD69 expression on all relevant immune effector cell populations, and similar results were observed as early as 6 hours postadministration (data not shown). These results indicate that systemic administration of CLDC (empty vector) induces massive and rapid immune activation.

(b) The following experiment shows that CLDC, but not lipid or DNA alone, induce immune activation in vivo. C57Bl/6 mice were injected intravenously with DNA alone (empty vector; 10 ug), lipid alone (DOTAP:cholesterol), or DNA+lipid (CLDC-empty vector) as described above (Sections A & C) and upregulation of CD69 expression (immune activation) on T cells, NK cells was evaluated 24 hours later by flow cytometry (Section E). The data presented in FIG. 2A (CD69+/CD8+ cells) and 2B (CD69+/NK1.1+ cells) clearly illustrate the synergistic immune stimulatory interaction that occurs when DNA and cationic lipids are complexed together. Similar results were also obtained for CD4+ T cells, B cells and macrophages (data not shown).

Figure 3:
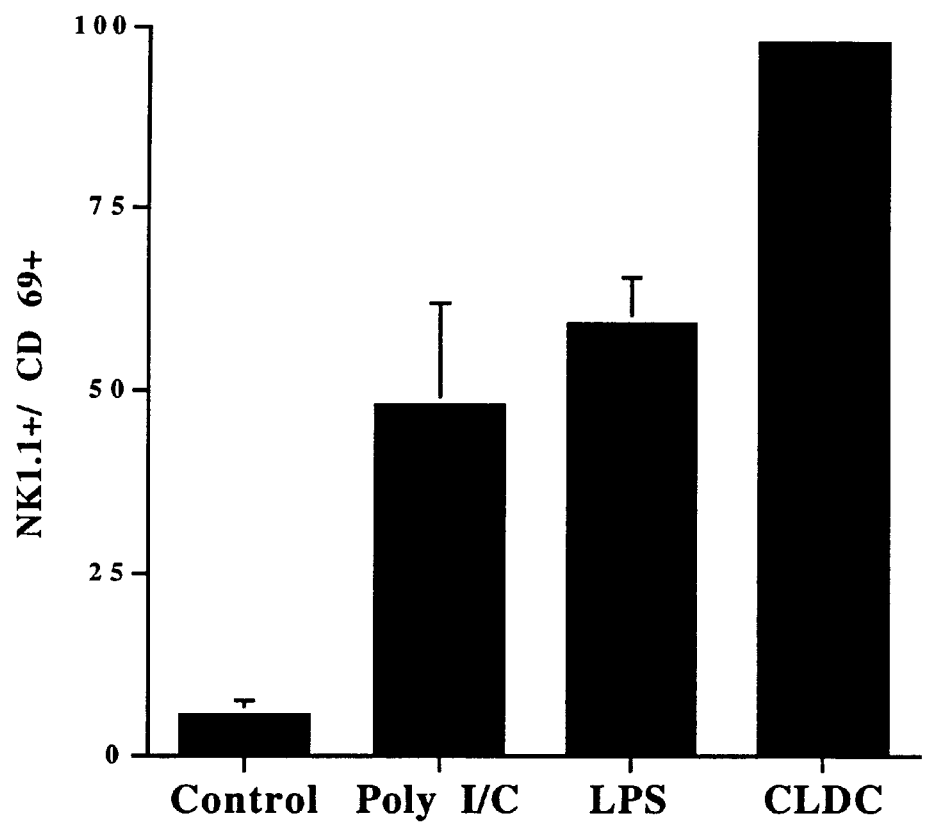
FIG. 3 is a bar graph comparing the immune activating potencies of LPS, poly I/C and CLDC in vivo.

(c) The following experiment compares the immune activating potencies of LPS, poly I/C, and CLDC (empty vector). C57Bl/6 mice were injected i.v. with 10 ug each of LPS, poly I/C, or CLDC (10 μg DNA) and spleen cells were analyzed for upregulation of CD69 by flow cytometry 24 hours later (as described in Sections A, C, E). FIG. 3 shows that injection of CLDC induced substantially greater immune activation than either of the classical immune activating stimuli, LPS or poly I/C, indicative of the extreme immune activating potency of CLDC.

Figure 4:
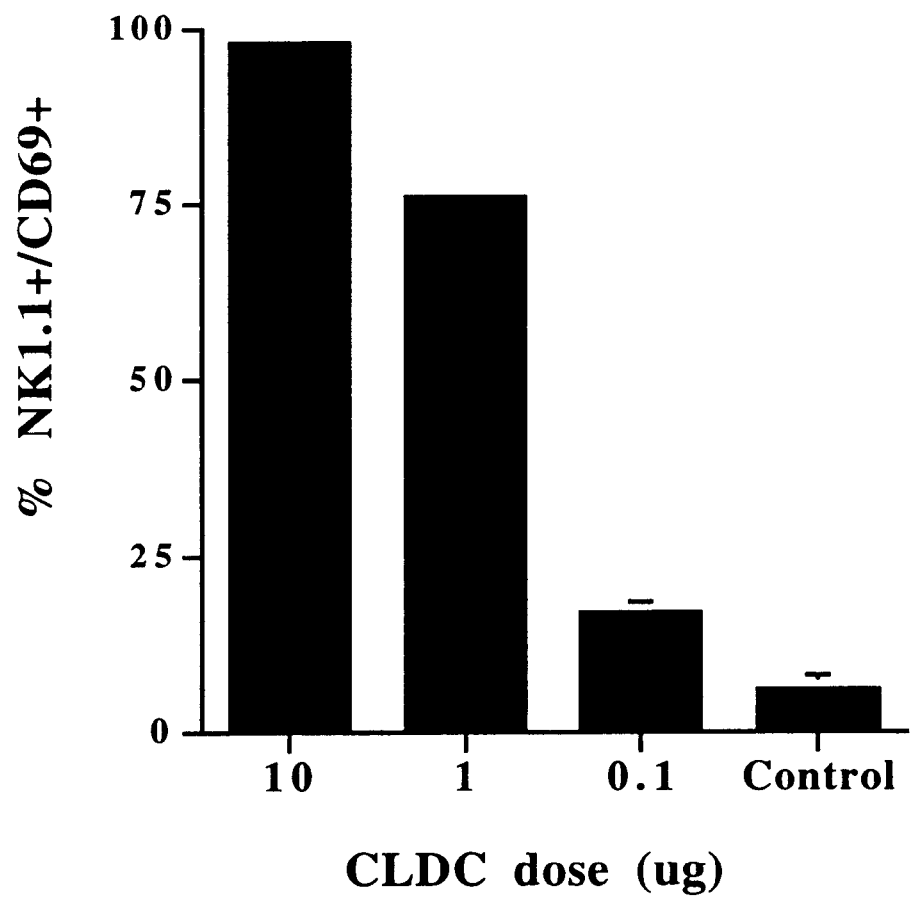
FIG. 4 is a bar graph is a bar graph showing in vivo dose responses for immune activation by CLDC.

(d) The following experiment shows that even low dose CLDC administered by the present method induces significant immune activation. C57Bl/16 mice were injected i.v. with decreasing doses of CLDC (empty vector), and immune activation (CD69 upregulation on NK cells) was assessed 24 hours later (see Sections A, C, E). FIG. 4 shows that even an extremely low dose of CLDC (100 ng) was capable of inducing significant immune activation.

Figure 5:
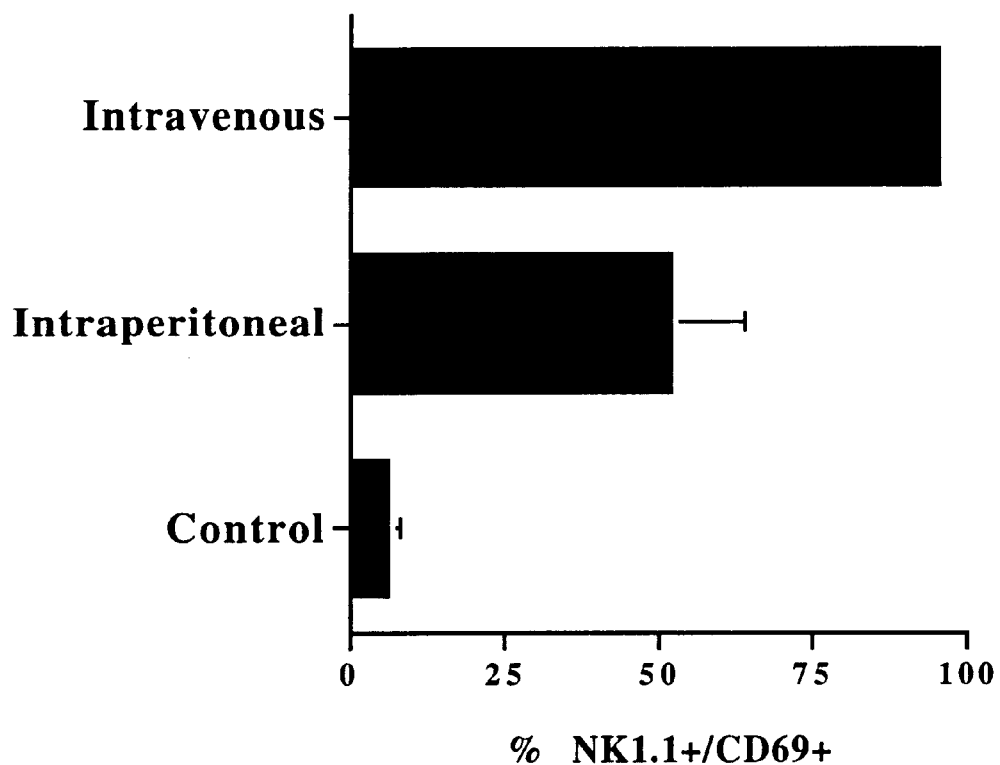
FIG. 5 is a bar graph illustrating the influence of route of administration of CLDC on immune activation.

(e) The following experiment demonstrates that both intraperitoneal and intravenous administration of CLDC induce potent immune activation. CLDC (empty vector) were administered to C57Bl/6 mice either intravenously (i.v.) or: intraperitoneally (i.p.), and immune activation (CD69 upregulation) on splenic NK cells was assessed: by flow cytometry (See Sections A, C, E). FIG. 5 shows that administration of CLDC by either route induced substantial immune activation, although the i.v. route was more potent than the i.p. route.

Figure 6:
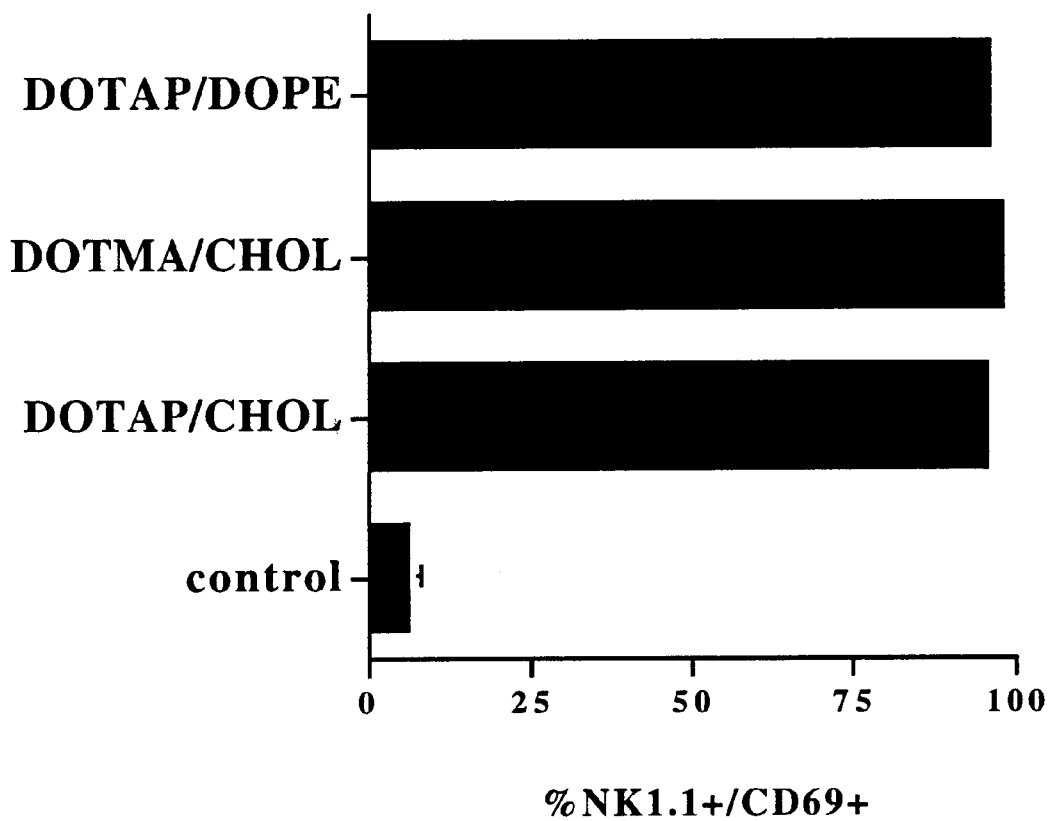
FIG. 6 is a bar graph showing that immune activation can be induced by CLDC formed with several different lipids.

(f) The following experiment shows that the immune activation elicited by administration of CLDC according to the present method can be induced by different lipid formulations. C57Bl/6 mice were injected i.v. with CLDC (empty vector) prepared using liposomes of several different lipid compositions, but all formulated as MLVs (as described in Sections A & C). At 24 hours post injection, the degree of immune activation (CD69 upregulation) on spleen cells was assessed (Section E). FIG. 6 shows that equivalent immune activation was induced by lipids having 3 different chemical compositions, indicating that the immune activating properties of CLDC is a general property and is not dependent on any one particular lipid composition.

Figure 7:
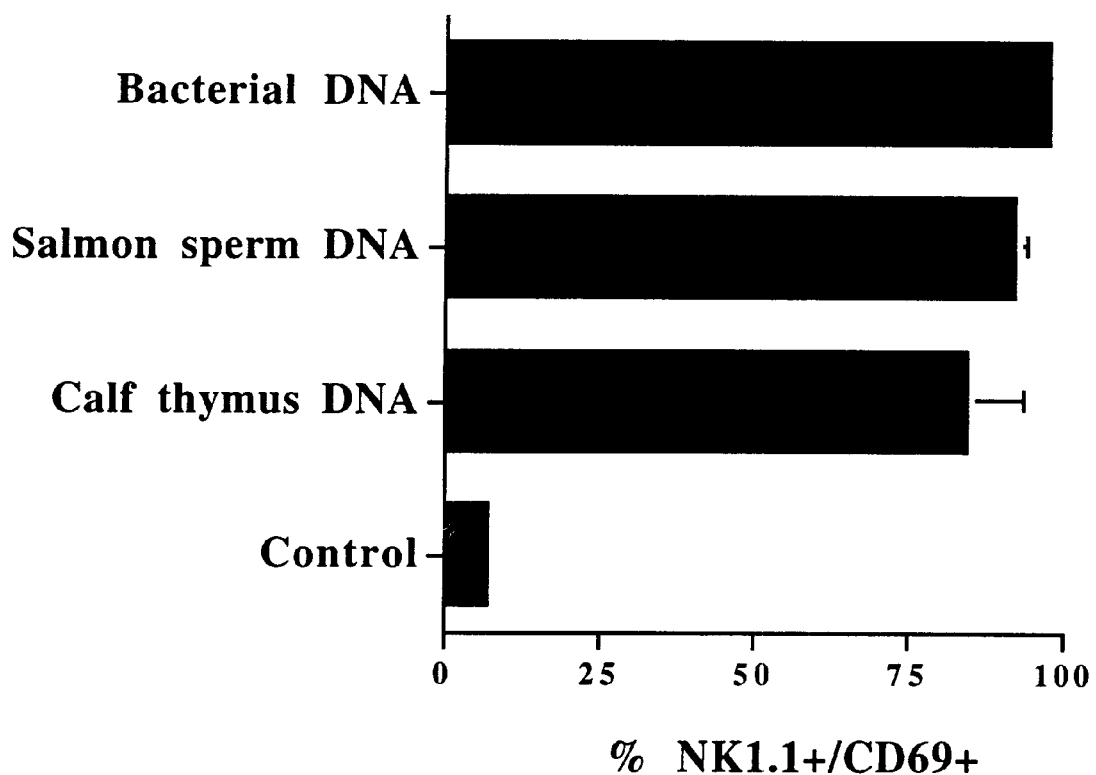
FIG. 7 is a bar graph demonstrating that immune activation by CLDC is independent of the DNA source.

(g) The following experiment demonstrates that immune activation by CLDC is independent of the DNA source. It has been previously established that bacterial DNA is immunostimulatory in mammals, whereas DNA from eukaryotic sources is not (See, for example, Pisetsky et al., 1996, supra; Pisetsky, 1996, supra; Yamamoto, et al., 1994, supra; Roman, et al., 1997, supra; Krieg, 1996, supra; Sun, et al., 1996, supra; Stacey et al., 1996, supra; Sato, et al., 1996, supra; or Ballas, 1996, supra). Therefore, the ability of CLDC formulated with either bacterial DNA (empty vector plasmid DNA) or eukaryotic DNA from 2 different sources (salmon sperm or calf thymus) was evaluated in vivo. C57Bl/6 mice were injected i.v. with CLDC containing DNA from one of these sources (each formulated to deliver 10 ug DNA per mouse) (See Section A & C). Twenty-four hours after i.v. injection of CLDC, the degree of CD69 upregulation on splenic NK cells was assessed by flow cytometry (Section E). FIG. 7 illustrates that immune activation was observed when mice were injected with CLDC comprised of either eukaryotic or bacterial DNA. Injection of salmon sperm or calf thymus DNA alone did not induce CD69 upregulation (data not shown). Thus, the immune activating properties of CLDC are surprisingly independent of the DNA source, and immune activation can also be induced by complexes of cationic lipids and RNA (see Example 7 below).

Figure 8:
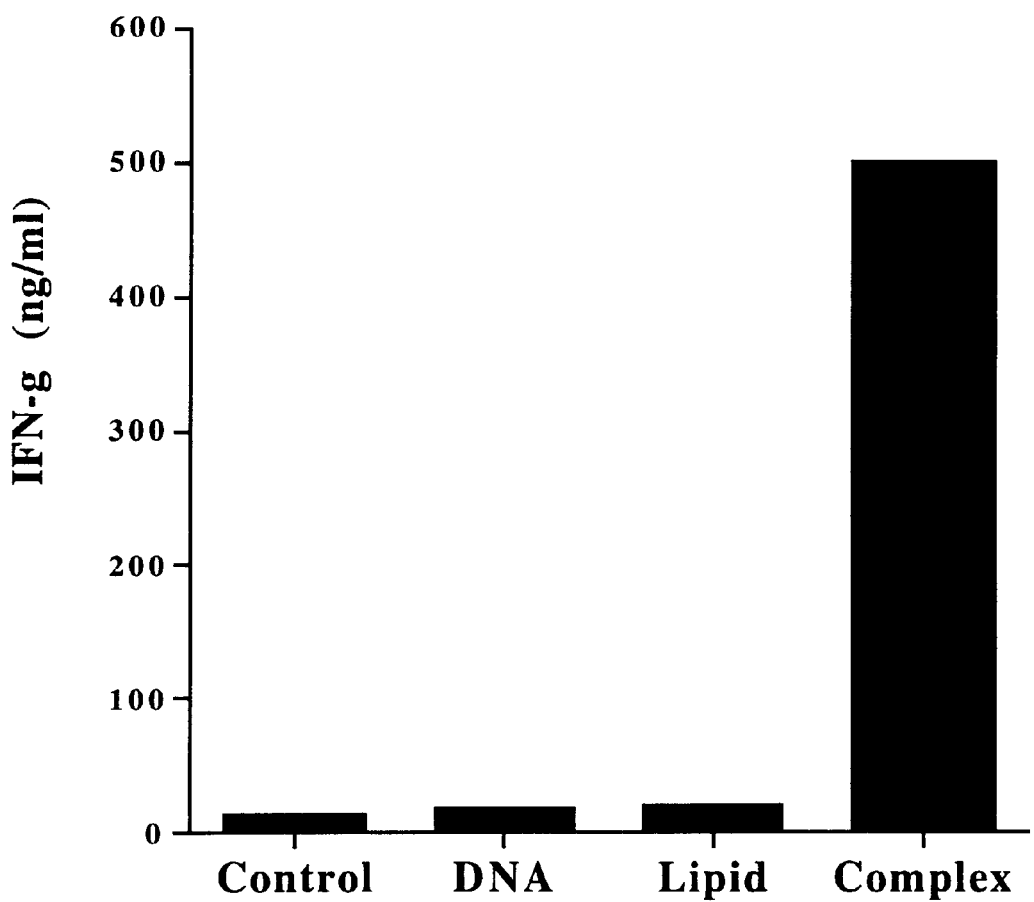
FIG. 8 is a bar graph illustrating that IFNγ release by immune cells is induced by administration of CLDC, but not lipid or DNA alone.

(h) The following experiment shows that cytokine release is induced by CLDC, but not by DNA or lipid alone. Spleen cells were incubated for 24 hours in vitro with CLDC (empty vector), DNA alone (empty vector), or lipid alone (DOTAP:cholesterol) and the supernatants were assayed for IFNγ (as well as other cytokines, data not shown) (See Sections D & H). FIG. 8 shows the results of an IFNγ ELISA. As was observed for CD69 upregulation, cytokine release is also triggered only by the CLDC and not by either component alone. Thus, formation of the DNA-lipid complex clearly markedly accentuates any immune stimulatory properties that plasmid DNA and lipid alone might possess.

Figure 9:
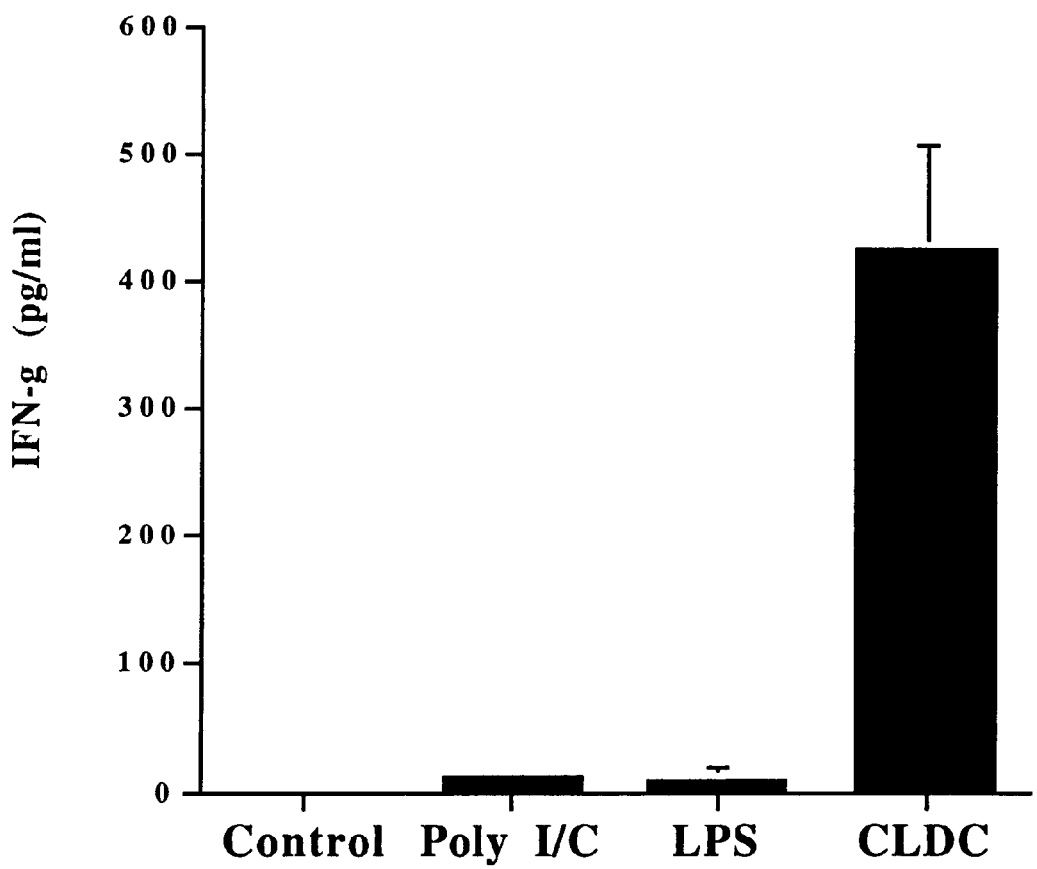
FIG. 9 is a bar graph showing that administration of CLDC, but not poly I/C or LPS, induces IFNγ production by splenocytes in vivo.

(i) The following experiment demonstrates that injection of CLDC, but not poly I/C or LPS, induces IFNγ production in vivo. C57Bl/6 mice (3 per group) were injected i.v. with 10 ug of either CLDC (empty vector), poly I/C, or LPS (as described in Sections A & C). Six hours later, spleen cells were harvested and cultured in vitro for an additional 12 hours. Then, cytokine levels in the supernatants were measured (Section H). FIG. 9 shows that the in vivo cytokine response to CLDC injection was clearly different than the response to 2 other classical immune activating stimuli (LPS, poly I/C), thereby illustrating a marked difference between CLDC and other so-called non-specific immune stimulators.

(j) The following experiment shows that NK cells are the source of IFNγ production elicited by i.v. CLDC injection. To determine the cell type producing IFNγ after injection of CLDC (empty vector), C57Bl/6 mice were depleted of NK cells using an anti-NK cell antibody (EV/aNK), or were untreated (control), or injected with CLDC and untreated (EV/−) or injected with CLDC and treated with an irrelevant antiserum (EV/NRS) (as described in Section G). The amount of IFNγ elaborated by spleen (FIG. 10A) and lung cells (FIG. 10B) 24 hours after injection of CLDC was quantitated (Section H). This experiment demonstrates that NK cells are the primary source of IFNγ induced by i.v. administration of CLDC.

(k) The following experiment shows that intravenous injection of CLDC induces high levels of NK activity in spleen cells. FIG. 11 illustrates that spleen cells harvested 24 hours after i.v. injection of CLDC (empty vector) exhibit high levels of killing of tumor target cells (tumor cell cytotoxicity) (See Section F). To identify the cell type responsible for this tumor cell killing activity, C57Bl/6 mice were depleted of NK cells 48 hours prior to injection of CLDC (asialo GM1) or were treated with an irrelevant antiserum (NRS) or were untreated (control) (as described in Section G). This experiment indicates that NK cells are the primary cell type responsible for the tumor cell killing activity elicited by injection of CLDC.

Figure 12A:
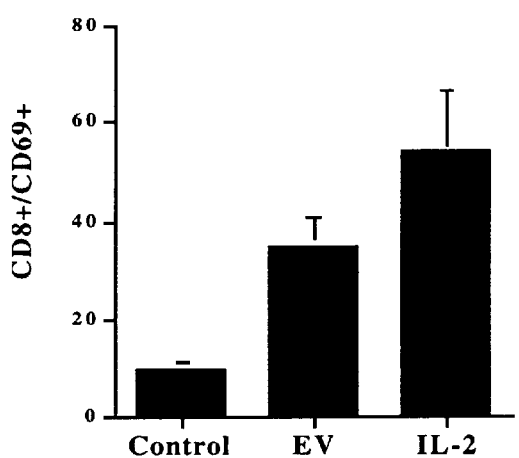
FIG. 12A is a bar graph showing that intraperitoneal administration of CLDC induces immune activation in CD8+ splenocytes in vivo.
Figure 12B:
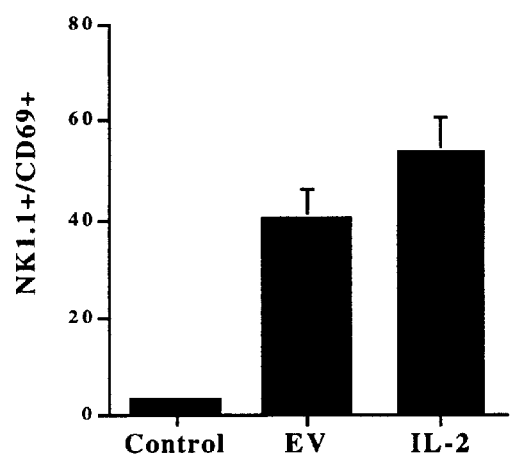
FIG. 12B is a bar graph showing that intraperitoneal administration of CLDC induces immune activation in NK1.1+ splenocytes in vivo.

(l) The following experiment demonstrates that intraperitoneal injection of CLDC induces immune activation. Spleen cells were harvested from C57Bl/6 mice 24 hours after intraperitoneal injection of 10 ug CLDC (10 μg DNA) complexes encoding either nothing (empty vector; EV) or the IL-2 gene (IL-2), and assayed for CD69 upregulation in both CD8+ and NK1.1+ cells (Sections A, B, C & E). FIG. 12A (CD8+) and FIG. 12B (NK1.1+) shows that intraperitoneal injection of CLDC with either empty vector or the IL-2 gene induced immune activation, although the effect was not as great as that induced by i.v. delivery (see FIG. 5). CLDC encoding IL-2 also demonstrated an enhanced immune activation as compared to CLDC (empty vector).

Example 2

The following experiments a–d and FIGS. 13–16 demonstrate that CLDC formed with non-coding DNA (empty vector) exert potent antitumor effects in vivo when administered according to the method of the present invention.

Figure 13A:
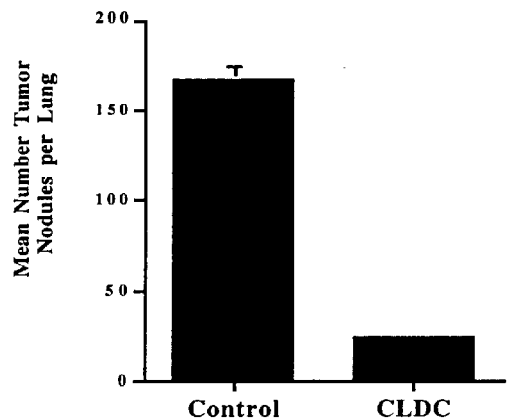
FIG. 13A is a bar graph demonstrating that CLDC exert potent antitumor effects against fibrosarcoma tumor cells in vivo.
Figure 13B:
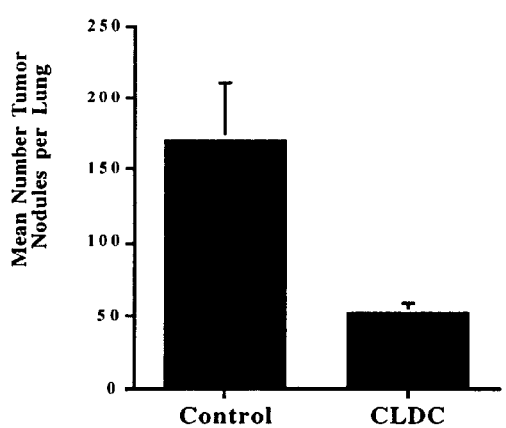
FIG. 13B is a bar graph demonstrating that CLDC exert potent antitumor effects against melanoma tumor cells in vivo.
Figure 13C:
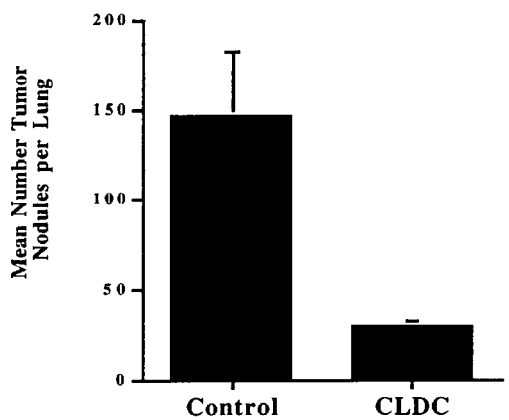
FIG. 13C is a bar graph demonstrating that CLDC exert potent antitumor effects against colon carcinoma tumor cells in vivo.
Figure 13D:
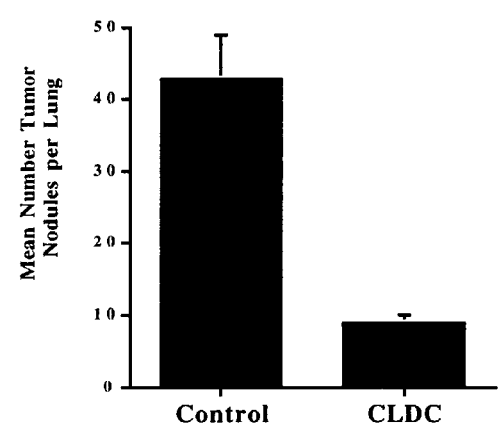
FIG. 13D is a bar graph demonstrating that CLDC exert potent antitumor effects against breast cancer tumor cells in vivo.

(a) The following experiment demonstrates that CLDC exert potent antitumor effects when administered to a mammal by the present method. The antitumor efficacy of CLDC (empty vector) was evaluated in 4 different murine models of metastatic cancer: MCA-205 (C57Bl/6; fibrosarcoma; FIG. 13A); B16 (C57Bl/6; melanoma; FIG. 13B); CT26 (BALB/c; colon carcinoma; FIG. 13C); and 4T1 (BALB/c; breast cancer; FIG. 13D). In each model, tumors were established in the lungs of mice (4 per group) by i.v. injection of $2.5 \times 10^5$ tumor cells per mouse (as described in Section I). Three days after the tumor cells were injected, treatment with i.v. administration of 100 ul CLDC was administered (10 ug empty vector DNA complexed to MLV liposomes as described in Sections A & C), and repeated once in 7 days. Control mice were injected with diluent (D5W). Seven days after the second injection (17 days after the tumor cells were first injected), the mice were sacrificed and the number of tumor nodules in the lungs determined by manual counting, as described above (Wexter et al., 1966, supra). FIGS. 13A–D illustrates the potent antitumor activity exerted by systemically administered CLDC, using 4 different tumor models and 2 different strains of mice (C57Bl/6 and BALB/c).

Figure 14:
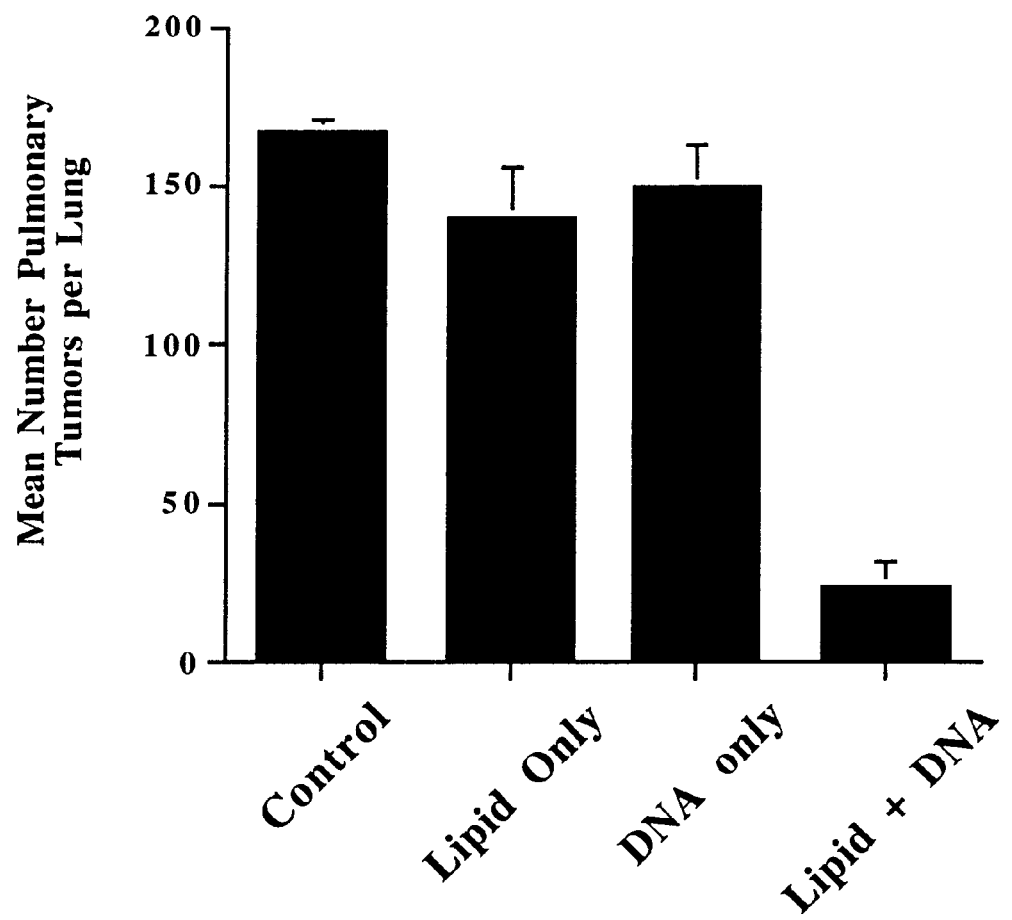
FIG. 14 is a bar graph showing that systemic administration of CLDC, but not DNA or lipid alone, induces antitumor activity in vivo.

(b) The following experiment shows that systemic administration of CLDC, but not administration of DNA or lipid alone, induces antitumor activity. C57Bl/6 mice (4 per group) with day 3 established MCA-205 tumors (Section I) were treated twice with i.v. injections of either MLV liposomes alone, empty vector DNA alone, or CLDC (empty vector) (See Sections A and I). The number of lung tumor metastases was determined on day 17 post-tumor injection and the results are shown in FIG. 14. This experiment demonstrates that the CLDC, but neither of the 2 constituents (DNA or lipid) alone, induces antitumor activity.

Figure 15:
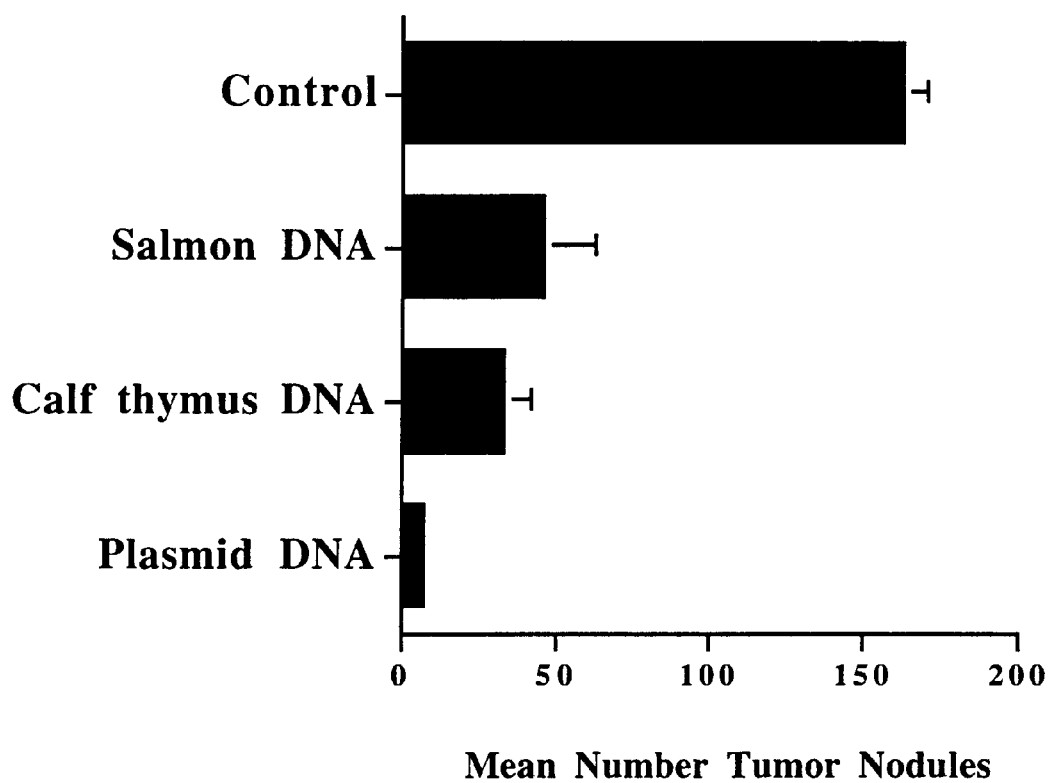
FIG. 15 is a bar graph demonstrating that the antitumor activity of CLDC is independent of the DNA source.

(c) The following experiment shows that the antitumor activity of CLDC (empty vector) is independent of the DNA source. To determine whether the antitumor activity observed with CLDC in experiments (a) and (b) above was only a property of CLDC formulated with bacterial DNA, mice with day 3 established MCA-205 lung metastases were treated with CLDC that were formed using either plasmid (bacterial) DNA, or eukaryotic DNA (from calf thymus or salmon testis). FIG. 15 shows clearly that CLDC formulated with either bacterial or eukaryotic DNA induced antitumor activity, though the bacterial DNA had slightly more potent activity.

Figure 16:
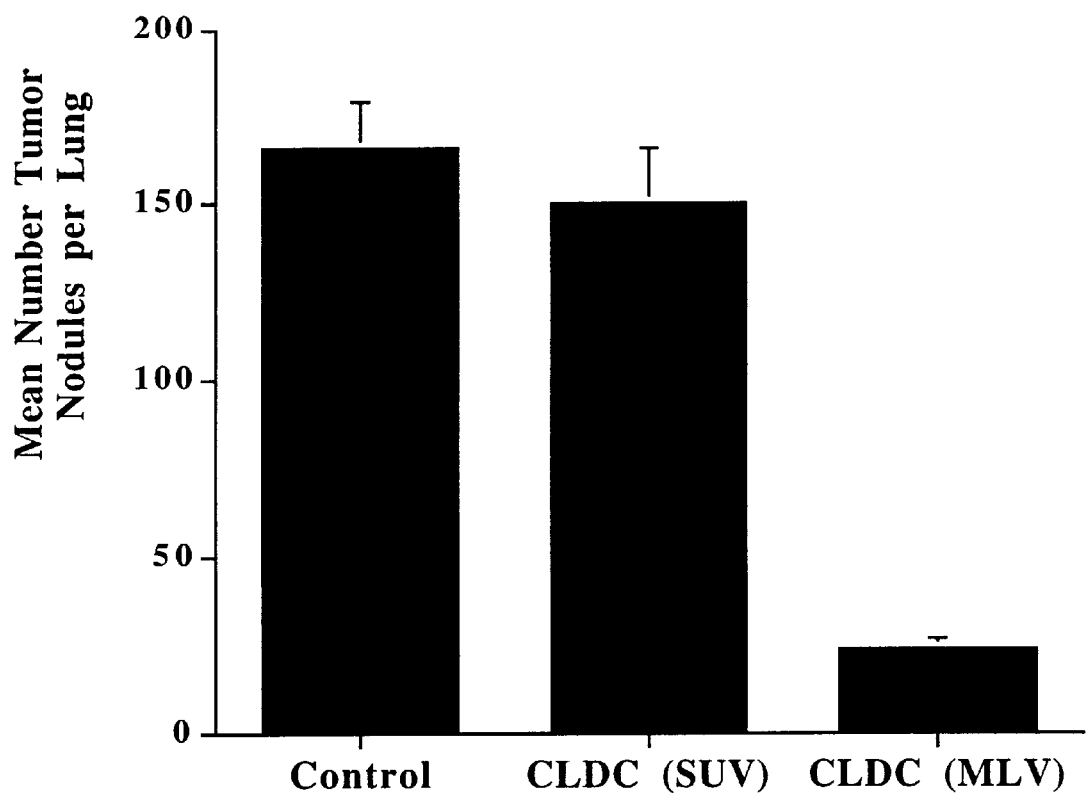
FIG. 16 is a bar graph showing that the type of CLDC administered significantly influences antitumor activity.

(d) The following experiment demonstrates that the type of CLDC administered significantly influences antitumor activity of the composition. Previous investigators have used CLDC formulated as SUV (small unilamellar vesicles) to target systemic gene transfer to the lungs. The present inventors have found that systemic administration of CLDC formulated as MLV, however, induce much greater antitumor activity, even when only empty vector DNA is administered. FIG. 16 clearly illustrates this difference. FIG. 16 shows that, where day 3 MCA-205 lung metastases were treated with 10 ug empty vector DNA administered using CLDC formulated as either SUVs or MLVs, the MLV formulations provided significantly greater antitumor effects.

Example 3

Figure 17A:
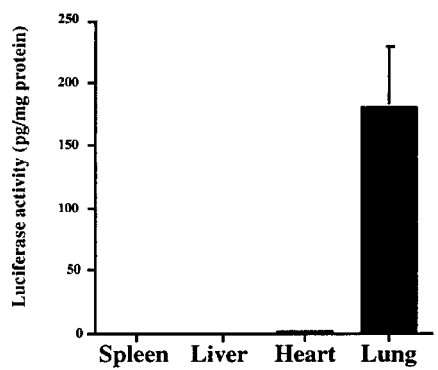
FIG. 17A is a bar graph illustrating that intravenous administration of CLDC induces selective gene expression in pulmonary tissues.
Figure 17B:
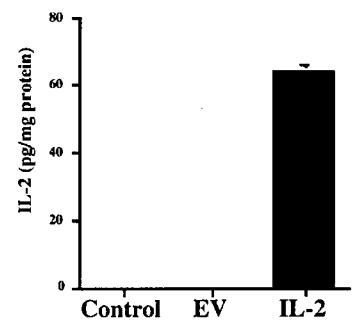
FIG. 17B is a bar graph illustrating that intravenous administration of CLDC encoding IL-2 induces intrapulmonary IL-2 expression.
Figure 17C:
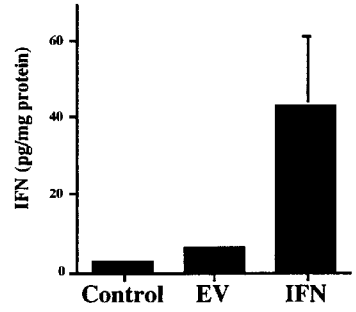
FIG. 17C is a bar graph illustrating that intravenous administration of CLDC encoding IFNγ induces intrapulmonary IFNγ expression.
Figure 18A:
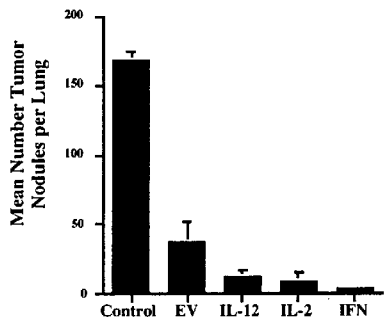
FIG. 18A is a bar graph showing that day 3 administration of CLDC encoding 3 different cytokine genes improves the antitumor activity against fibrosarcoma tumor cells in vivo over empty vector alone.
Figure 18B:
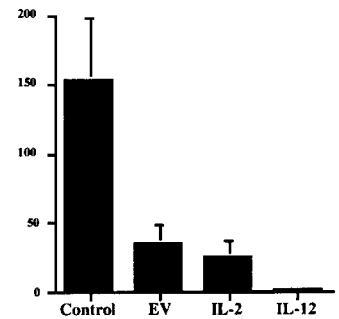
FIG. 18B is a bar graph showing that day 3 administration of CLDC encoding 3 different cytokine genes improves the antitumor activity against colon carcinoma tumor cells in vivo over empty vector alone.
Figure 18C:
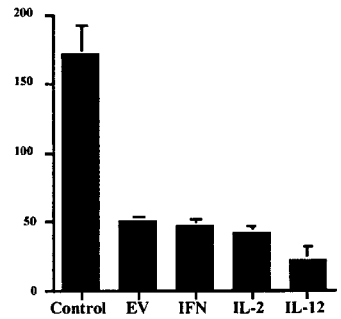
FIG. 18C is a bar graph showing that day 3 administration of CLDC encoding 3 different cytokine genes improves the antitumor activity against melanoma tumor cells in vivo over empty vector alone.
Figure 18D:
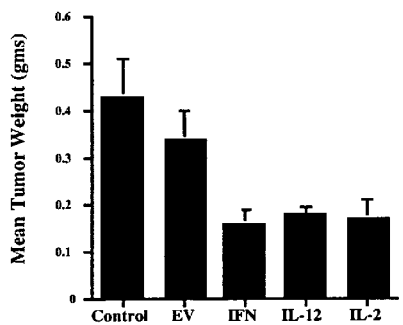
FIG. 18D is a bar graph showing that day 6 administration of CLDC encoding 3 different cytokine genes improves the antitumor activity against fibrosarcoma tumor cells in vivo over empty vector alone.
Figure 18E:
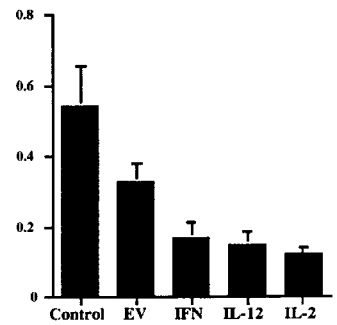
FIG. 18E is a bar graph showing that day 6 administration of CLDC encoding 3 different cytokine genes improves the antitumor activity against colon carcinoma tumor cells in vivo over empty vector alone.
Figure 18F:
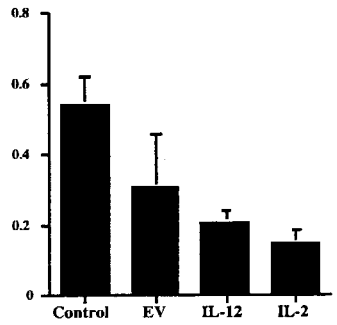
FIG. 18F is a bar graph showing that day 6 administration of CLDC encoding 3 different cytokine genes improves the antitumor activity against melanoma tumor cells in vivo over empty vector alone.

The following experiment and FIGS. 17A–C shows that intravenous injection of CLDC induces selective gene expression in pulmonary tissues. C57Bl/6 mice were injected i.v. with CLDC encoding a reporter gene, courteously provided; by Dr. Robert Debs (luciferase; panel a), and the location of gene expression in various organs was determined 24 hours later (See Sections A, B & C). As shown in FIG. 17A, luciferase gene expression was almost exclusively confined to pulmonary tissues. In FIGS. 17B and 17C, i.v. injection of CLDC encoding IL-2 or IFNγ resulted in efficient intrapulmonary expression of IL-2 and IFNγ, as demonstrated by determination of cytokine expression in lung tissues extracted from the mice. Injection of non-coding CLDC (EV) was included as an additional control.

Example 4

The following experiment and FIGS. 18A–F demonstrates that administration of cytokine genes using CLDC delivery improves the antitumor effect over empty vector alone. Using 3 different tumor models as described in Example 2 (MCA-205, FIGS. 18A and 18D; CT26, FIGS. 18B and 18E; B16, FIGS. 18C and 18F), we evaluated the antitumor effects of i.v. delivery of cytokine genes (IL-2, IFNγ, and IL-12) using CLDC containing plasmid DNA expressing these genes, and compared the antitumor effects to those induced by empty vector DNA (See Sections A, B, C, & I). In both the day 3 treatment models (FIGS. 18A, 18B and 18C) and the day 6 treatment models (FIGS. 18D, 18E and 18F), addition of a cytokine gene that stimulates NK cells induced greater antitumor activity than the empty vector DNA alone, and this additional antitumor effect was particularly pronounced in the day 6 treatment models. It is believed, that the added antitumor effect induced by the cytokine genes enhances and depends to a large degree on the initial immune activation inherent to administration of CLDC.

Example 5

Figure 19A:
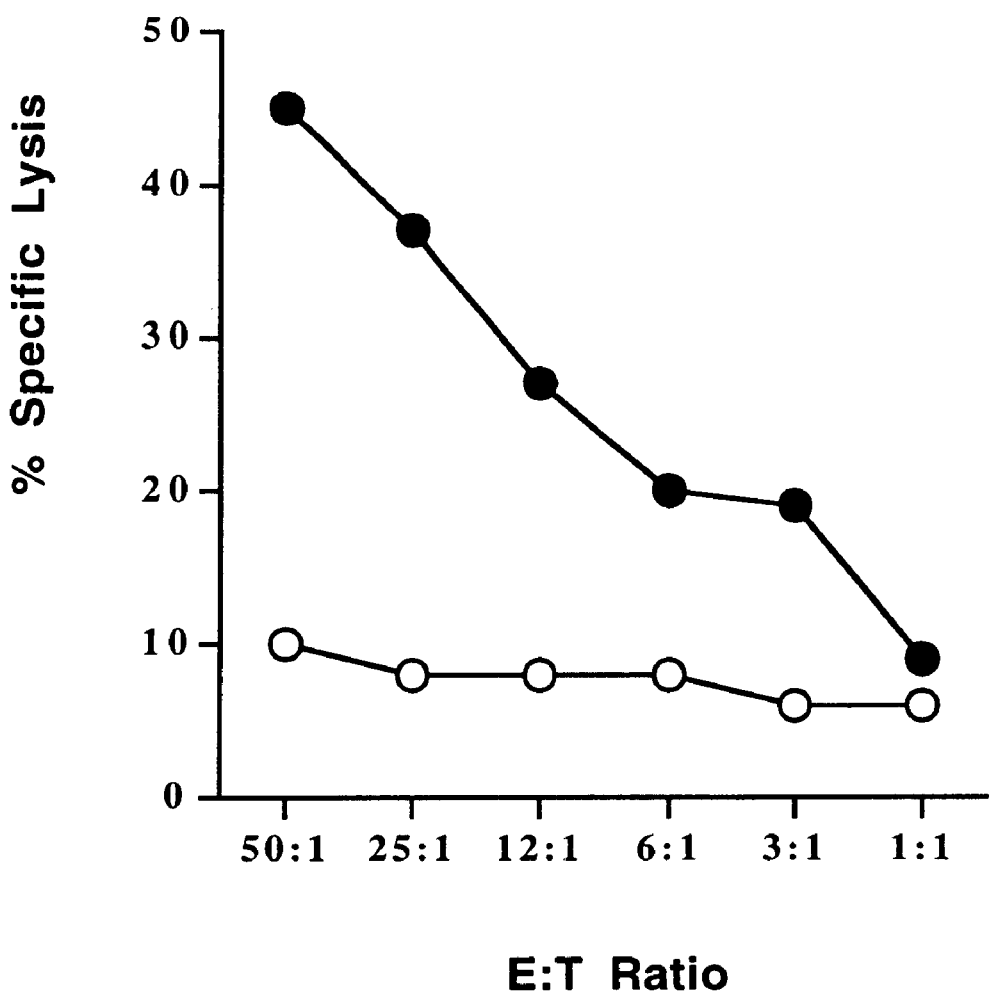
FIG. 19A is a line graph illustrating that intravenous administration of CLDC encoding ovalbumin induces strong, systemic, antigen-specific immune responses in vivo.
Figure 19B:
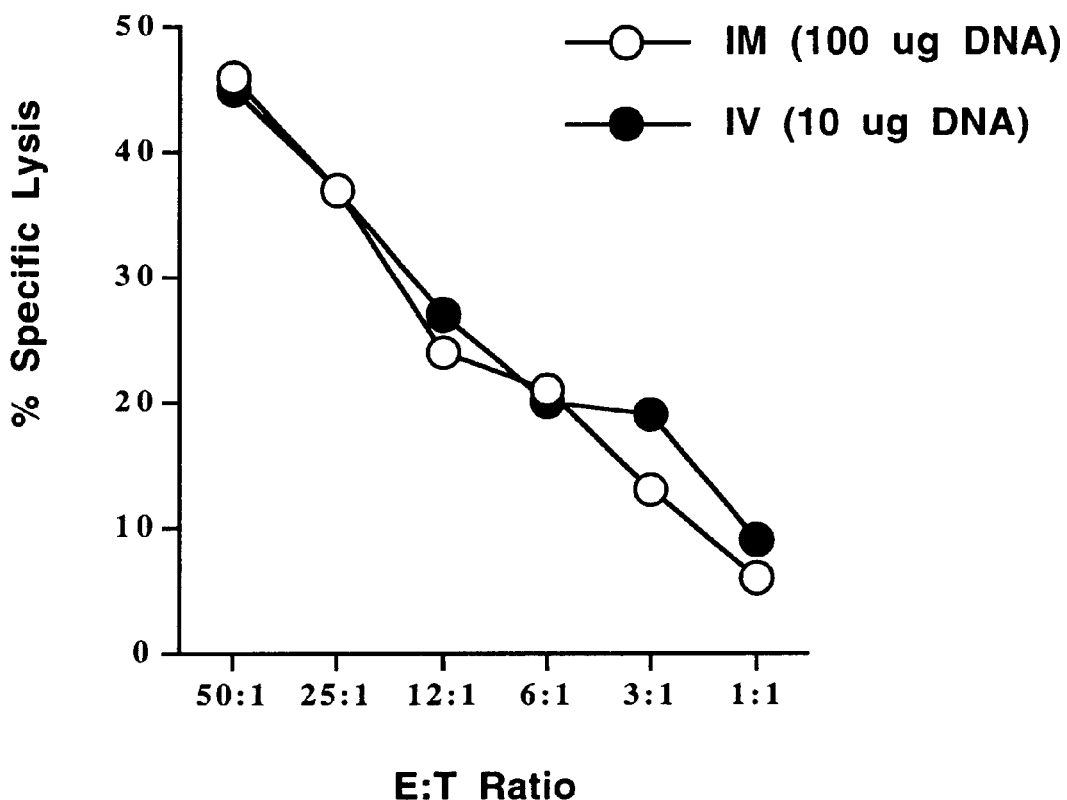
FIG. 19B is a line graph demonstrating that intravenous immunization with CLDC encoding an antigen is at least 10 times more potent immune inducer of immune activation than intramuscular injection of DNA encoding an antigen.

The following experiment and FIGS. 19A and 19B show that administration of CLDC having DNA encoding ovalbumin induces strong systemic antigen-specific immune responses.

The following experiment shows that intravenous injection of CLDC encoding an antigen gene induces strong systemic antigen-specific immune responses and that intravenous (i.v.) DNA immunization is more potent than intramuscular (i.m.) DNA immunization. C57Bl/6 mice (3 per group) were immunized either intramuscularly (IM) with 100 ug DNA encoding the ovalbumin (OVA) gene, or intravenously (IV) with 10 ug CLDC encoding the OVA gene (Sections A, B, C). Three weeks later, spleen cells were harvested and assayed for their ability (i.e., CTL activity) to lyse OVA-expressing target cells (Section F). The results are shown in FIGS. 19A and 19B. To detect OVA-specific CTL, lymphocytes from immunized mice were assayed for cytotoxic activity against a control cell line (open circles) or an OVA-expressing target cell (filled circles). FIG. 19A illustrates that there was significantly greater killing of the OVA-expressing target cells, indicating that immunization with CLDC encoding an antigen is an efficient means of inducing antigen-specific immune responses in vivo. FIG. 19B shows that administration of one-tenth of the amount of DNA using CLDC by intravenous administration induces equivalent levels of antigen-specific CTL activity observed with intramuscular injection.

Example 6

The following experiments a–d and FIGS. 20–23 demonstrate that the administration of CLDC having DNA encoding a tumor antigen induces strong anti-tumor activity and antigen-specific immune responses in vivo.

Figure 20:
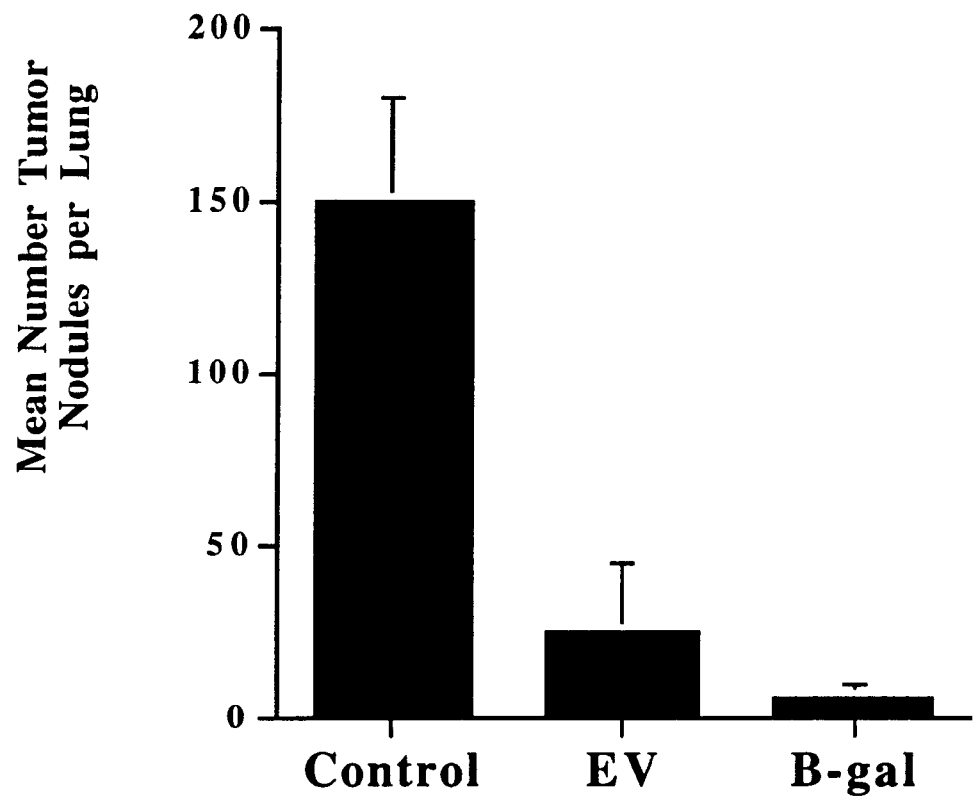
FIG. 20 is a bar graph showing that systemic immunization with CLDC encoding a tumor antigen induces strong antitumor activity.

(a) The following experiment shows that systemic immunization with CLDC encoding a tumor antigen induces strong antitumor activity in vivo. BALB/c mice (4 per group) were given $2.5 \times 10^5$ CL25 tumor cells i.v. to establish pulmonary metastases (Section I). The CL-25 tumor line is derived from the CT26 colon carcinoma cell line and has been modified to express the β-gal antigen. Three days after administration of the CL-25 tumor cells, mice were treated with 2 i.v. administrations of CLDC encoding either nothing (EV) or the β-gal gene (B-gal), one week apart (Sections A, B, C). One week after the second treatment, the mice were sacrificed and the antitumor effect was quantitated by counting the number of lung tumor nodules. FIG. 20 shows that the number of tumors was significantly reduced by administration of empty vector CLDC (EV), but was even further reduced by administration of CLDC encoding the specific tumor antigen, β-gal (B-gal). This experiment illustrates the principle that i.v. administration of CLDC encoding a tumor antigen (or antigen(s)) is an effective approach to eliciting immune responses against established tumors.

Figure 21:
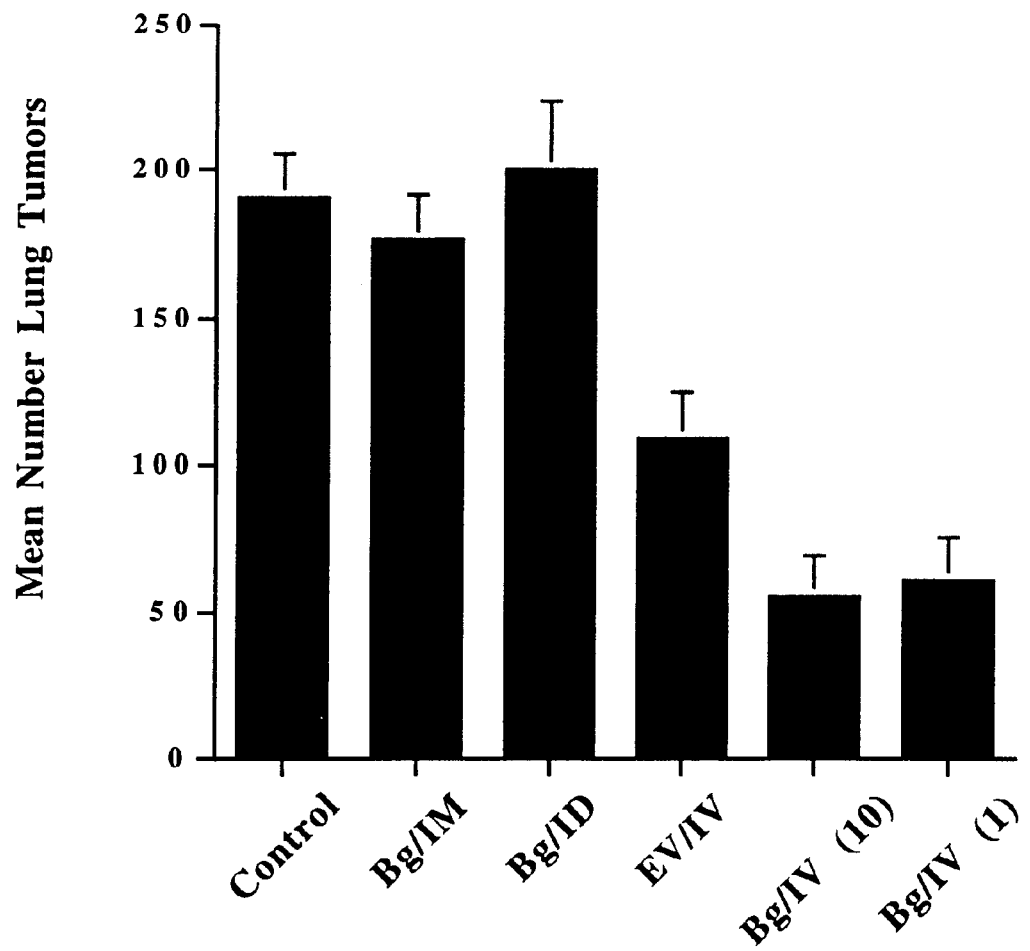
FIG. 21 is a bar graph illustrating that intravenous administration of CLDC encoding a tumor antigen induces effective antitumor immunity, whereas administration of DNA encoding a tumor antigen intramuscularly or intradermally does not.

(b) The following experiment demonstrates that i.v. administered, CLDC-mediated immunization against a tumor antigen induces effective antitumor immunity, whereas intramuscular (IM) or intradermal (ID) immunization does not. Mice (4 per treatment group) with day 3 established CL25 lung tumors were treated by intravenous DNA immunization with β-gal DNA (Sections A, B, C, I). FIG. 21 shows that mice treated with intramuscular (B-gal/IM) or intradermal (B-gal/ID) administration of 100 ug B-gal DNA showed no detectable antitumor effect as compared to control mice. By contrast, mice treated with β-gal CLDC (B-gal/IV; either 10 ug (10) or 1 ug (1) total DNA per mouse), had significantly reduced lung tumor burdens compared to control mice or to mice treated with i.v. administration of empty vector (EV/IV) CLDC, although i.v. administration of empty vector CLDC had a clear antitumor effect as compared to i.m. or i.d. administration of DNA. Thus, administration of 1/10th or 1/100th the amount of tumor antigen DNA using CLDC by i.v. administration was much more effective than conventional DNA immunization approaches.

Figure 22:
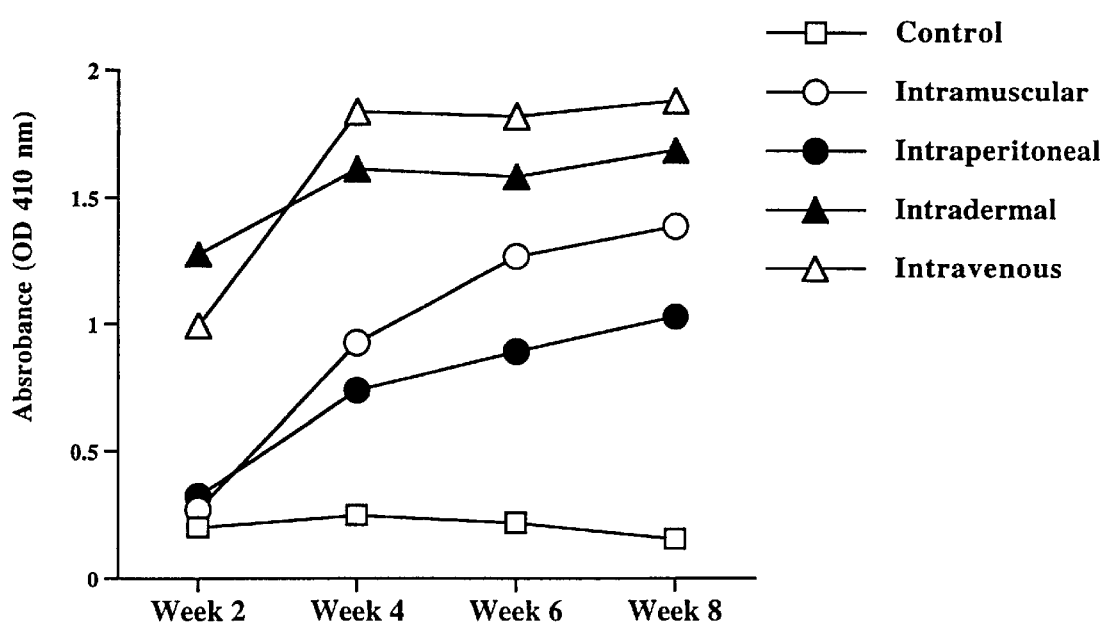
FIG. 22 is a line graph showing that intravenous administration of CLDC encoding a tumor antigen induces a potent humoral immune response against the tumor antigen in vivo.

(c) The following experiment demonstrates that CLDC-mediated intravenous immunization with a tumor antigen induces an antigen-specific humoral response in vivo. The relative efficiency of immunization via different routes of DNA administration was evaluated in BALB/c mice (4 per group) using plasmid DNA encoding the β-galactosidase gene (β-gal). At 2 week intervals, serum was collected from each mouse and assayed for antibodies against the β-gal protein, using an antibody ELISA assay. Mice immunized by the intradermal and intramuscular route were injected once with 50 μg β-gal plasmid DNA. Mice immunized once by the intravenous route and intraperitoneal routes received 10 μg DNA that was complexed to a cationic liposome (CLDC). Control animals were not treated. The mean β-gal-specific antibody level (at a 1:1000 serum dilution) was determined for each group of mice and plotted for each of 4 different time points evaluated. FIG. 22 shows that intravenous administration of CLDC containing 10 μg DNA elicited a similar antigen-specific humoral immune response to intradermal administration of 50 μg DNA, and both intravenous and intradermal administration elicited a more potent humoral immune response than either intraperitoneal or intramuscular injection of β-gal DNA.

Figure 23:
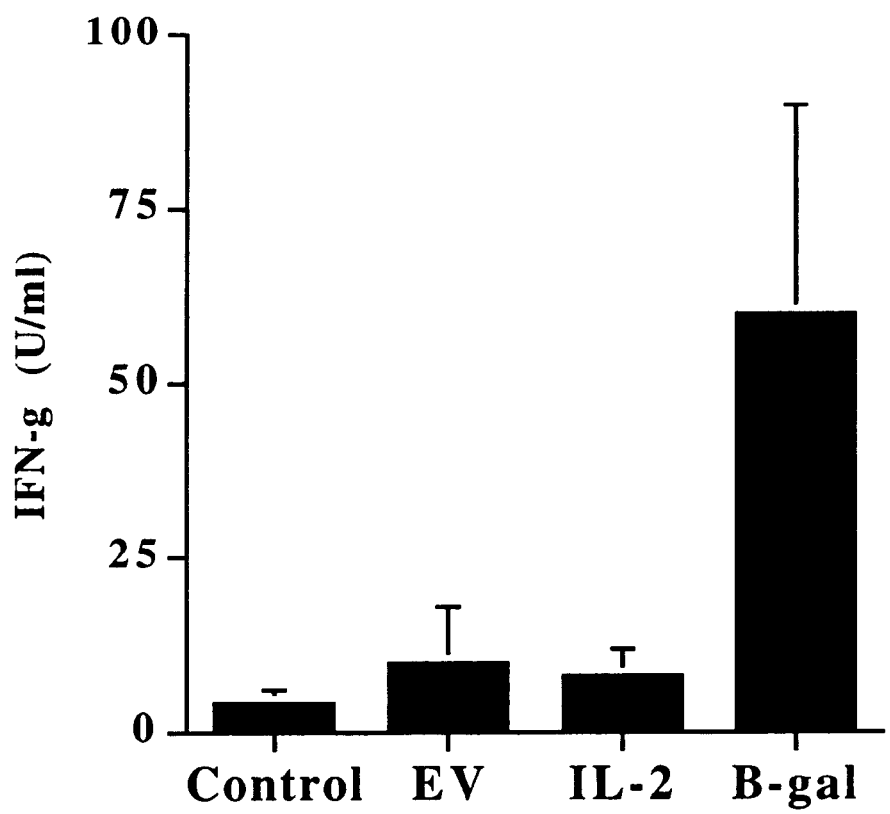
FIG. 23 is a bar graph showing that CLDC-mediated immunization with a tumor antigen induces antigen-specific production of IFNγ by splenocytes.

(d) The following experiment demonstrates that CLDC-mediated immunization with a tumor antigen induces antigen-specific production of IFNγ by spleen cells. As another means of assessing the effectiveness of CLDC-mediated immunization, the release of IFNγ (a cytokine with antitumor effects) was quantitated in spleen cells of mice that were immunized twice, one week apart, with either empty vector CLDC (EV), IL-2 CLDC (i.e., DNA encoding IL-2), or β-gal CLDC (DNA encoding β-gal) (Sections A, B, C & H). FIG. 23 demonstrates that, mice immunized with the β-gal CLDC mounted a strong antigen specific immune response when re-challenged in vitro with the CL25 (β-gal transfected) cell line, as measured by IFNγ production by splenocytes. In contrast, splenocytes from mice immunized with either empty vector CLDC (EV) or IL-2 CLDC (IL-2) produced very little IFNγ. These data further substantiate the effectiveness of antigen-specific immunization using CLDC. It is believed that this effectiveness stems in large part from the innate immune response that is triggered by systemic administration of any CLDC. This strong induction of innate immune responses undoubtedly serves as a powerful adjuvant for inducing strong immune responses to the antigen-encoding DNA.

Example 7

Figure 24:
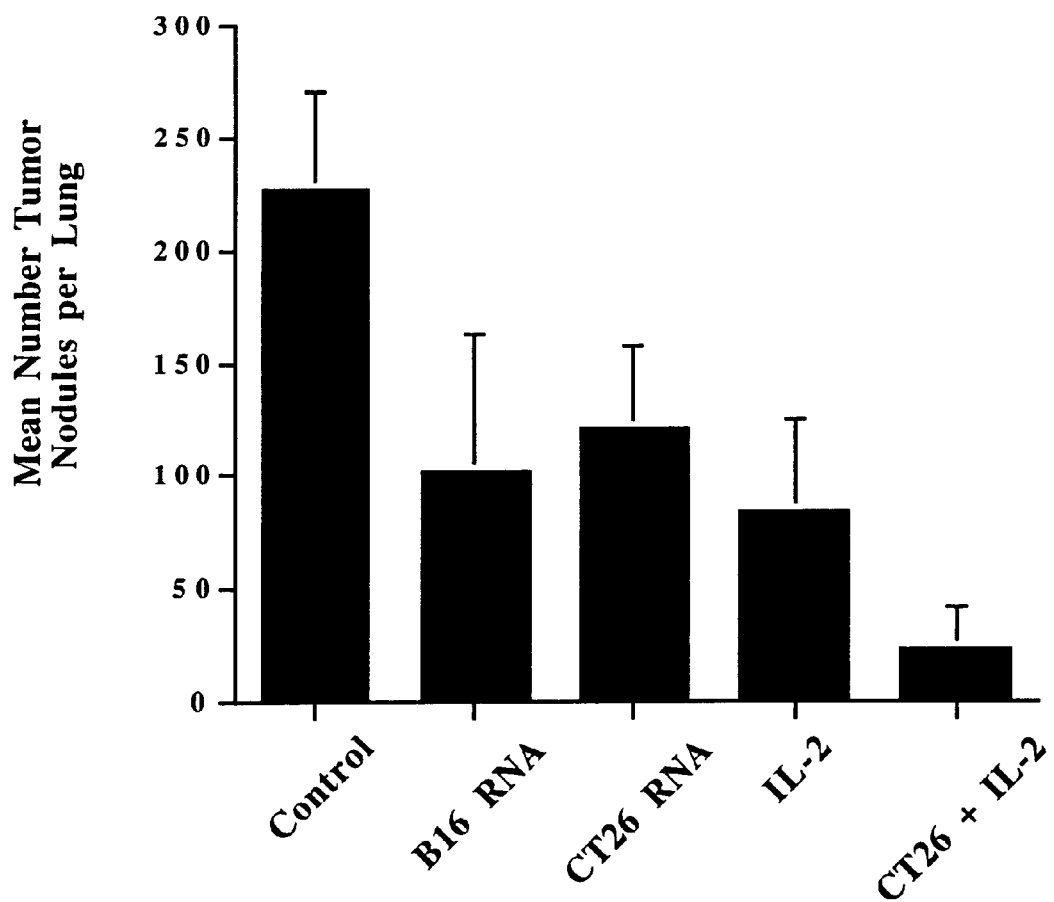
FIG. 24 is a bar graph demonstrating that CLRC-mediated immunization with tumor RNA with and without DNA encoding a cytokine induces strong antitumor activity in vivo.
Figure 25:
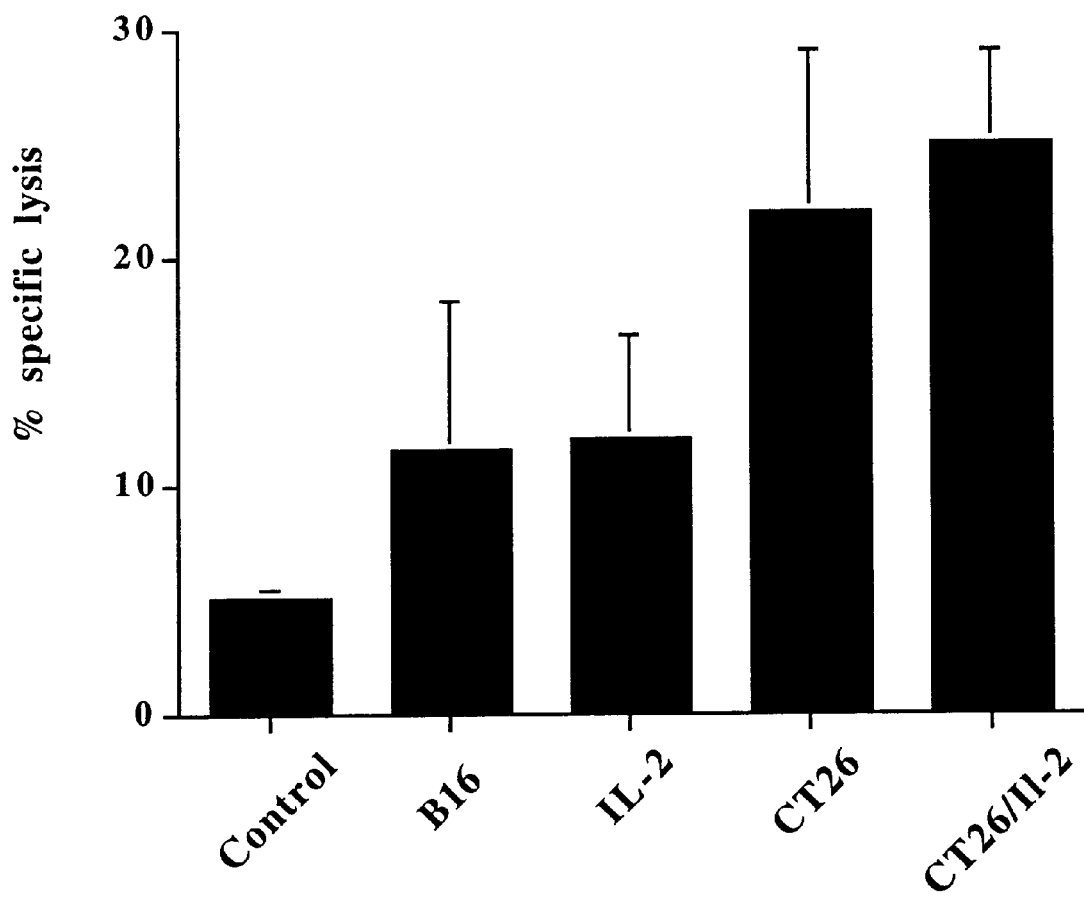
FIG. 25 is a bar graph illustrating that immunization with CLRC containing tumor-specific RNA induces tumor-specific CTL responses in vivo.

The following experiments a–b and FIGS. 24 and 25 demonstrate that administration of CLDC having RNA encoding a tumor antigen induces strong antitumor immunity and tumor-specific CTL responses in vivo.

(a) The following experiment shows that CLDC-mediated immunization with tumor RNA plus a cytokine induces strong antitumor immunity. The ability to immunize mice using polyA-enriched RNA from tumor cells was evaluated by complexing the RNA to a cationic lipid to form cationic lipid RNA complexes (CLRC) (Sections A & B). The antitumor effects were evaluated in BALB/c mice (4 per treatment group) with day 3 established CT26 lung tumor metastases (Section I). RNA was prepared from the autologous tumor cells (CT26 RNA) or from an irrelevant control tumor cell line (C57Bl/6 RNA), complexed to a cationic lipid, then injected i.v. to deliver approximately 50 ug RNA per mouse (Section C). One group of mice was treated with CLDC containing DNA encoding the IL-2 gene alone (IL-2), and a final group was treated with CLRC containing both CT26 RNA and DNA encoding the IL-2 gene (CT26+ IL-2). The lung tumor burden was quantitated 7 days after the second injection of CLDC. FIG. 24 shows that RNA can be effectively used to immunize mice against a tumor when combined into CLRC and delivered systemically, and that this antitumor effect can be enhanced by coadministering the RNA with the DNA encoding IL-2.

(b) This experiment demonstrates that immunization with tumor-specific RNA induces tumor-specific CTL responses. Mice with established CT26 tumors were immunized twice with CLRC containing either irrelevant RNA (B16), DNA encoding the IL-2 gene (IL-2), total CT26 RNA (CT26), or total CT26 RNA plus DNA encoding the IL-2 gene (CT26/IL-2) (Sections A, B, I). One week after the second immunization, spleen cells were harvested and assayed for their ability to lyse CT26 target cells in vitro (Section F). FIG. 25 shows that immunization with either CT26 RNA or CT26 RNA plus IL-2 induced the highest levels of antitumor CTL activity. Thus, CLDC-mediated immunization with a broad range (library) of unselected tumor antigens can induce tumor-specific immunity, and this immunity can be augmented by co-administration of a cytokine gene.

Example 8

Figure 26:
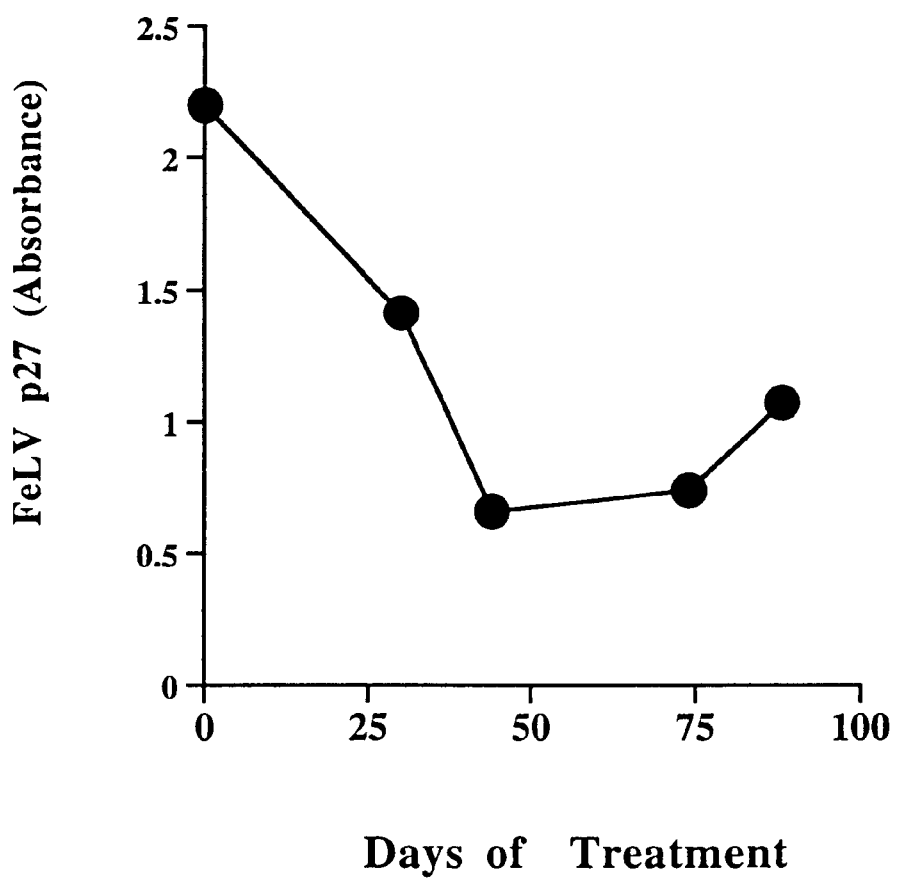
FIG. 26 is a line graph showing that intraperitoneal immunization with CLDC containing DNA encoding IL-2 induces a reduction in FeLV viral titer.

The following experiment and FIG. 26 demonstrate that intraperitoneal administration of CLDC containing DNA encoding IL-2 induces a reduction in FeLV viral titer. A cat chronically infected with the feline leukemia virus (FeLV) was treated with weekly (for 4 weeks), and then twice monthly intraperitoneal injections of 250 μg CLDC prepared (as described above) using plasmid DNA encoding the feline IL-2 gene. At various time points after treatment was initiated, blood was collected and the serum levels of; FeLV p27 determined using an ELISA (assays performed by Dr. Ed Hoover, Colorado State University). Over the course of 3 months of treatment, the FeLV p27 levels declined by 50%, and the cat's clinical signs improved (e.g., weight gain, increased hematocrit). In contrast, for 2 months prior to IL-2 CLDC treatment, the FeLV p27 levels had remained relatively constant (data not shown).

Example 9

Figure 27:
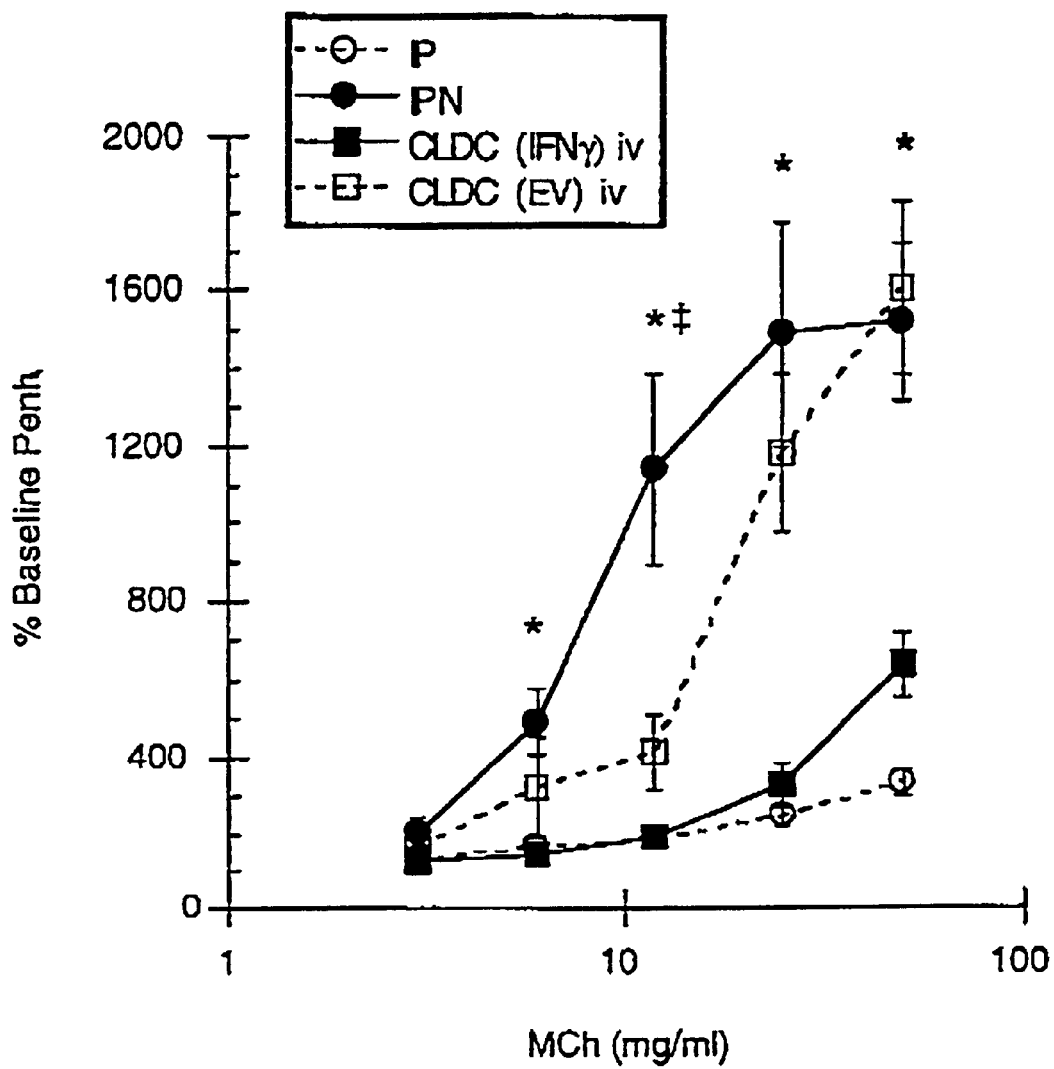
FIG. 27 is a line graph illustrating that intravenous pulmonary transfection with CLDC containing DNA encoding IFNγ inhibits the development of airway hyperresponsiveness in allergen sensitized and challenged mice.
Figure 28:
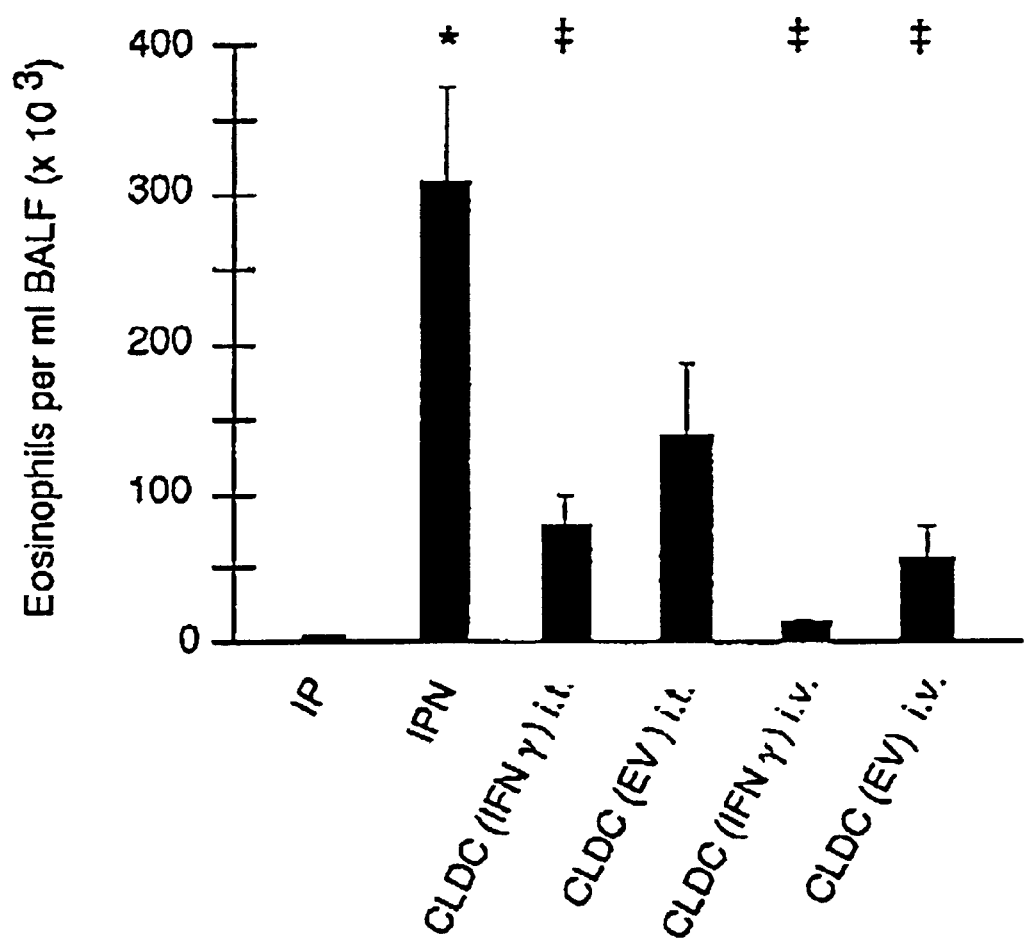
FIG. 28 is a bar graph demonstrating that intravenous pulmonary transfection with CLDC containing DNA encoding IFNγ inhibits eosinophil influx to the airways in mice sensitized and challenged with allergen.

The following experiments a–b and FIGS. 27–29 demonstrate that the composition and method of the present invention abrogates airway hyperresponsiveness and reduces airway eosinophil influx in a murine model of allergic asthma.

(a) BALB/c mice (at least 8 per treatment group) were sensitized to ovalbumin as follows. Briefly, mice were sensitized by intraperitoneal (i.p.) injection of 20 μg ovalbumin (OVA) (Grade V, Sigma Chemical Co., St. Louis, Mo.) together with 20 mg alum (Al(OH)$^3$) (Inject Alum; Pierce, Rockford, Ill.) in 100 μl PBS (phosphate-buffered saline), or with PBS alone. 72 hours before the mice were airway challenged with ovalbumin, the mice were treated with intravenous administration of IFNγ CLDC (IFN-g) or empty vector CLDC (EV). Controls included OVA-sensitized mice that were not treated (IPN) as well as untreated mice that did not receive airway sensitization (IP). Mice received subsequent OVA aerosol challenge for 20 minutes with a 1% OVA/PBS solution. Airways responsiveness (Penh) following increasing doses of methacholine was assessed using whole body plethysmography (Buxco, Troy, N.Y.) (asthma is known to increase the sensitivity of the airways to contractile agonists such as methacholine). In this system, an unrestrained spontaneously breathing mouse is placed into the main chamber of the plethysmograph, and pressure differences between this chamber and a reference chamber are recorded. The resulting box pressure signal is caused by volume and resultant pressure changes during the respiratory cycle of the animal. From these box pressure signals, the phases of the respiratory cycle, tidal volume, and the enhanced pause (Penh) can be calculated. Penh represents a function of the proportion of maximal expiratory to maximal inspiratory box pressure signals and of the timing of expiration. It correlates closely with pulmonary resistance measured by conventional two-chambered plethysmography in ventilated animals. FIG. 27 shows that allergen sensitized and challenged mice which received intravenous administration of IFNγ CLDC had significantly reduced airway hyperresponsiveness to methacholine challenge (i.e., almost equal to that of control (IP) mice), whereas airways responsiveness remained high in untreated animals (IPN). Animals treated with empty vector (CLDC) showed reduced hyperresponsiveness to methacholine at lower methacholine challenge doses. Additionally, both intravenous administration of IFNγ CLDC and empty vector CLDC reduced airway hyperresponsiveness to methacholine significantly better than administration of recombinant IFNγ protein (data not shown).

(b) In this experiment, BALB/c mice were sensitized to ovalbumin as described in section (a) above, then treated with CLDC delivered either intravenously (IV) or intratracheally (IT). The degree of eosinophil infiltration into the airways (a measure of airways allergen sensitization) was quantitated in bronchoalveolar lavage fluid (BALF). The mean number of eosinophils per ml BALF fluid was plotted for each group of mice (unsensitized control {IP}; sensitized, untreated control {IPN}; and sensitized mice treated with either intratracheal IFNγ CLDC, intratracheal EV CLDC, intravenous IFNγ CLDC, or intravenous EV CLDC). FIG. 28 demonstrates that treatment with intravenous CLDC (both EV and IFNγ CLDC) significantly reduced eosinophil infiltration compared to control (IPN) animals.

Example 10

The following example demonstrates that spleen and lung cells from mice receiving intravenous, but not intratracheal, administration of CLDC produce significant amounts of IFNγ.

Figures 29A, 29B:
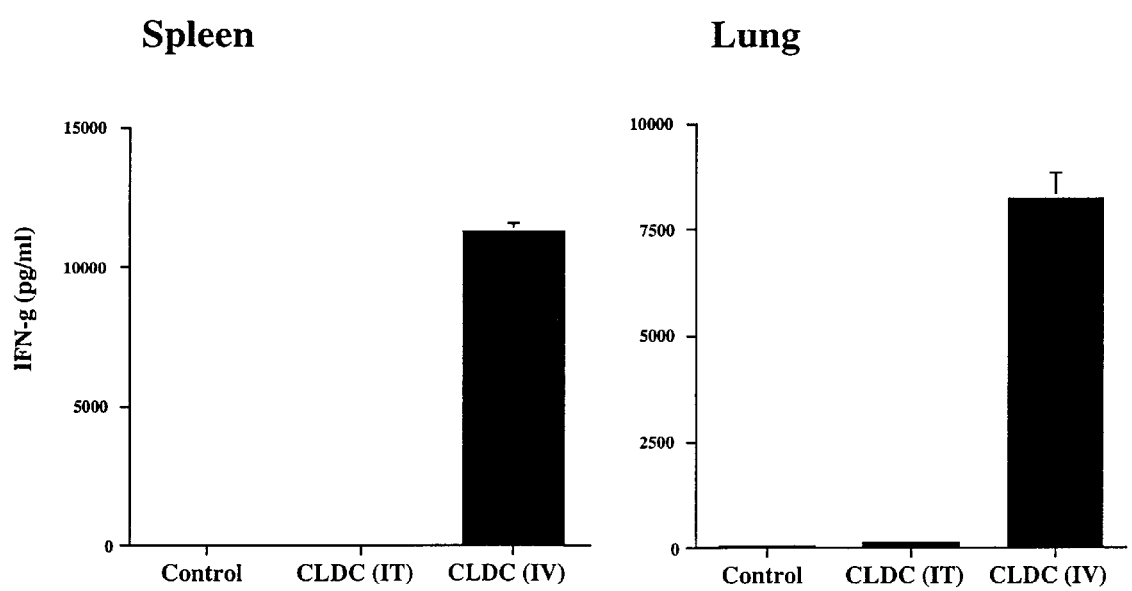
FIG. 29A is a bar graph illustrating that intravenous administration of CLDC induces IFNγ release from spleen as compared to intratracheal administration.
FIG. 29B is a bar graph illustrating that intravenous administration of CLDC induces IFNγ release from lung as compared to intratracheal administration.

BALB/c mice were administered CLDC containing 10 μg of DNA either intravenously or intratracheally as described in experiments above. 24 hours post-administration, IFNγ production was measured from isolated spleen (FIG. 29A) and lung (FIG. 29B) cells of the animals. FIG. 29 shows that mice receiving intravenous administration of CLDC produced significant amounts of IFNγ in contrast to mice receiving intratracheal administration of CLDC.

Example 11

The following example demonstrates that intravenous administration of CLDC containing DNA encoding IL-2 eradicates metastatic lung tumors in a dog.

A canine patient had a rear limb amputation for osteosarcoma, followed by adjuvant chemotherapy for prevention of tumor metastasis. Osteosarcoma is a highly malignant tumor of dogs that metastasizes readily to the lungs, even after complete removal (amputation) of the primary tumor the median survival time for dogs following amputation is 4 months, with death due to tumor metastases. Canine osteosarcoma is thus a highly relevant and useful animal model of osteosarcoma in humans.

Six months after this patient underwent amputation and adjuvant chemotherapy, the dog was re-evaluated and metastatic tumors were found in the lung on thoracic radiographs. The dog was then entered into a cancer immunotherapy trial, using intravenously administered CLDC encoding the canine IL-2 gene. The dog was treated weekly for 12 weeks with increasing doses of CLDC, up to a maximum dose of 500 μg (10 μg/kg body weight). After 6 weeks of treatment, partial tumor regression was observed on thoracic radiographs, and by 12 treatments, 90% regression of lung tumor nodules was observed. Additional treatments have been given at once monthly intervals and the dog remains in remission at 1.2 years after entering into the study.

This example demonstrates the potential efficacy of systemically administered CLDC as a cancer treatment in animals in addition to mice. Thus, efficacy was demonstrated in a large, outbred animal (dog) with a spontaneous, highly malignant metastatic tumor (osteosarcoma), with minimal toxicity at the doses employed here.

In summary, the above-described experiments have demonstrated:

1. Systemic injection of CLDC containing empty vector (non-coding) plasmid DNA induces intense immune activation, as assessed by upregulation of an early activation marker (CD69), by induction of NK cell cytotoxic activity, increase in NK cell numbers and by induction of cytokine release in vivo.

2. Immune stimulation in vitro or in vivo (at the doses evaluated here) is induced by the complex of DNA and cationic lipid (CLDC), and not by either DNA or lipid alone.

3. Immune activation induced by CLDC is quantitatively more potent than that induced by either LPS (endotoxin) or poly I/C (a classical inducer of antiviral immune responses) Furthermore, the type of immune stimulation induced (e.g., the pattern of cytokines induced) also differs qualitatively from that induced by LPS.

4. Immune activation by CLDC can be induced by eukaryotic as well as prokaryotic DNA, indicating that there is some property of the CLDC that is inherently immune activating, regardless of the source of the DNA.

5. Immune activation is induced by complexes of CLDC containing RNA.

6. Although any complex of DNA and lipid can conceivably induce some immune activation, CLDC prepared using MLV liposomes induce the maximal and optimal immune stimulation which induces effective antitumor responses.

7. Systemic administration of tumor antigen genes using CLDC is more effective than some more conventional routes of DNA immunization (e.g., intramuscular), and equivalent to others (e.g., intradermal at higher doses of DNA), for inducing antigen-specific humoral immunity. Intradermal administration, however, does not provide the anti-tumor effect observed with systemic administration.

8. Systemic administration of one-tenth of the amount of DNA using CLDC by intravenous administration induces equivalent levels of antigen-specific CTL activity observed with intramuscular injection.

9. Intravenously administered, CLDC-mediated immunization against a tumor antigen induces effective antitumor immunity, whereas intramuscular (IM) or intradermal (ID) immunization does not.

10. Combined administration of an antigen-encoding (i.e., immunogen-encoding) gene with a cytokine-encoding gene induces greater immune responsiveness to the antigen gene, and greater antitumor activity.

11. Systemic i.v. administration of CLDC prepared using MLV liposomes induces preferential transfection of pulmonary tissues. Furthermore, i.v. administration of CLDC encoding certain cytokine genes (e.g., those that stimulate NK cells) induce greater antitumor effects (against established lung tumors) than administration of empty vector DNA.

12. The primary anti-tumor effector cell induced by systemic administration of CLDC is the NK cell.

13. The cytokine response to administration of CLDC is characteristic of the response to acute viral infections, and is dominated by release of IFNγ from macrophages, NK cells, and other cell types throughout the body. This pattern of response is ideally suited for treatment of cancer, viral infections, and to serve as an adjuvant for certain types of vaccines.

14. Systemic administration of CLDC containing DNA encoding a cytokine induces a reduction in viral titer.

15. Systemic administration of CLDC containing DNA encoding a cytokine abrogates airway hyperresponsiveness and reduces airway eosinophil influx in an allergic asthma model.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A composition for the elicitation of a systemic, non-antigen specific immune response in a mammal comprising:
   a. a cationic liposome delivery vehicle; and;
   b. an isolated nucleic acid molecule selected from the group consisting of:
      i. an oligonucleotide comprising a CpG motif; and
      ii. an isolated bacterially-derived nucleic acid vector without a gene insert, or a fragment thereof;

wherein said therapeutic composition elicits a systemic, non-antigen-specific immune response in said mammal.

2. The composition of claim 1, wherein said liposome delivery vehicle comprises lipids selected from the group consisting of multilamellar vesicle lipids and extruded lipids.

3. The composition of claim 1, wherein said liposome delivery vehicle comprises multilamellar vesicle lipids.

4. The composition of claim 1, wherein said liposome delivery vehicle comprises pairs of lipids selected from the group consisting of DOTMA and cholesterol; DOTAP and cholesterol; DOTIM and cholesterol; and DDAB and cholesterol.

5. The composition of claim 1, wherein said liposome delivery vehicle comprises DOTAP and cholesterol.

6. The composition of claim 1, wherein comprising a pharmaceutically acceptable excipient.

7. The composition of claim 6, wherein said excipient comprises a non-ionic diluent.

8. The composition of claim 7, wherein said excipient is 5 percent dextrose in water.

9. The composition of claim 1, wherein said composition has a nucleic acid to lipid ratio of from about 1:1 to about 1:64.

10. A method for eliciting a systemic, non-antigen specific immune response in a mammal, comprising administering to said mammal an amount of a composition effective to elicit said immune response, wherein said composition comprises:
    a. a cationic liposome delivery vehicle; and;
    b. an isolated nucleic acid molecule selected from the group consisting of:
       i. an oligonucleotide comprising a CpG motif; and
       ii. an isolated bacterially-derived nucleic acid vector without a gene insert or a fragment thereof.

11. The method of claim 10, wherein said liposome delivery vehicle comprises lipids selected from the group consisting of multilamellar vesicle lipids and extruded lipids.

12. The method of claim 10, wherein said liposome delivery vehicle comprises multilamellar vesicle lipids.

13. The method of claim 10, wherein said liposome delivery vehicle comprises pairs of lipids selected from the group consisting of DOTMA and cholesterol; DOTAP and cholesterol; DOTIM and cholesterol, and DDAB and cholesterol.

14. The method of claim 10, wherein said liposome delivery vehicle comprises DOTAP and cholesterol.

15. The method of claim 10, wherein said composition further comprises a pharmaceutically acceptable excipient.

16. The method of claim 15, wherein said excipient comprises a non-ionic diluent.

17. The method of claim 16, wherein said excipient is 5 percent dextrose in water.

18. The method of claim 10, wherein said composition has a nucleic acid to lipid ratio of from about 1:1 to about 1:64.

* * * * *